United States Patent
Vogel

(10) Patent No.: US 10,801,038 B2
(45) Date of Patent: Oct. 13, 2020

(54) OPTO-GENETIC MODULATOR

(71) Applicant: Trustees of Boston University, Boston, MA (US)

(72) Inventor: Adam Tyler Vogel, Brookline, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/907,480

(22) Filed: Feb. 28, 2018

(65) Prior Publication Data

US 2018/0245097 A1 Aug. 30, 2018

Related U.S. Application Data

(60) Provisional application No. 62/464,859, filed on Feb. 28, 2017.

(51) Int. Cl.
*C12N 15/85* (2006.01)
*C12Q 1/6876* (2018.01)
*C12Q 1/6897* (2018.01)

(52) U.S. Cl.
CPC ........... *C12N 15/85* (2013.01); *C12Q 1/6876* (2013.01); *C12Q 1/6897* (2013.01); *C12N 2015/8527* (2013.01)

(58) Field of Classification Search
None
See application file for complete search history.

(56) References Cited

U.S. PATENT DOCUMENTS

| 2006/0223141 | A1* | 10/2006 | Carey | A01K 67/0271 435/69.1 |
| 2012/0165204 | A1* | 6/2012 | Hahn | C12N 9/16 506/2 |

FOREIGN PATENT DOCUMENTS

| WO | 2012/116621 A1 | 9/2012 |
| WO | 2014/019527 A1 | 2/2014 |
| WO | 2015/041219 A1 | 3/2015 |

OTHER PUBLICATIONS

Boyden et al., "Millisecond-timescale, genetically targeted optical control of neural activity", Nat Neurosci 8(9) 1263-1268 (2005).
Boyden et al., "Optogenetics and the future of neuroscience", Nat Neurosci 18(9) 1200-1201 (2015).
Carrion et al., "DREAM is a Ca2+-regulated transcriptional repressor", Nature 398(6722) 80-84 (1999).
Cosentino et al., "Optogenetics. Engineering of a light-gated potassium channel", Science 348(6235) 707-710 (2015).
Fields et al., "Action potential-dependent regulation of gene expression: temporal specificity in ca2+, cAMP-responsive element binding proteins, and mitogen-activated protein kinase signaling", J Neurosci 17(19) 7252-7266 (1997).
Halavaty et al., "N- and C-terminal flanking regions modulate light-induced signal transduction in the LOV2 domain of the blue light sensor phototropin 1 from Avena sativa", Biochemistry 46(49) 14001-14009 (2007).
Harper et al., "Structural basis of a phototropin light switch", Science 301(5639) 1541-1544 (2003).
Ledo et al., "The DREAM-DRE interaction: key nucleotides and dominant negative mutants", Biochim Biophys Acta 1498(2-3) 162-168 (2002).
Lungu et al., "Designing photoswitchable peptides using the AsLOV2 domain", Chem Biol 19(4) 507-517 (2012).
Marblestone et al., "Designing tools for assumption-proof brain mapping", Neuron 83(6) 1239-1241 (2014).
O'Connor et al., "Reverse engineering the mouse brain", Nature 461(7266) 923-929 (2009).
Packer et al., "Simultaneous all-optical manipulation and recording of neural circuit activity with cellular resolution in vivo", Nat Methods 12(2) 140-146 (2015).
Polstein et al., "Light-inducible spatiotemporal control of gene activation by customizable zinc finger transcription factors", J Am Chem Soc 134(40) 16480-16483 (2012).
Ramirez et al., "Creating a false memory in the hippocampus", Science 341(6144) 387-391 (2013).
Rickgauer et al., "Simultaneous cellular-resolution optical perturbation and imaging of place cell firing fields", Nature Neuroscience 17; 1816-1824 (2014).
Sheng et al., "Specific regulation of immediate early genes by patterned neuronal activity", J Neurosci Res 35(5) 459-467 (1993).
Strickland et al., "Light-activated DNA binding in a designed allosteric protein", Proc Natl Acad Sci USA 105(31) 10709-10714 (2008).
Szabo et al., "Spatially selective holographic photoactivation and functional fluorescence imaging in freely behaving mice with a fiberscope", Neuron 84(6) 1157-1169 (2014).
Wu et al., "Spatiotemporal control of small GTPases with light using the LOV domain", Methods Enzymol 497: 393-407 (2011).

* cited by examiner

*Primary Examiner* — Antonio Galisteo Gonzalez
(74) *Attorney, Agent, or Firm* — Nixon Peabody LLP; Ronald I. Eisenstein; Mark J. FitzGerald

(57) ABSTRACT

Provided herein are opto-genetic systems, cells, and methods thereof for modulating and regulating genetic expression in transiently active cells. The technologies described herein provide a transformative genetic regulatory tool for in vivo applications, which broadly spans a variety of disciplines, including behavioral, cognitive, and systems neuroscience.

23 Claims, 33 Drawing Sheets
(33 of 33 Drawing Sheet(s) Filed in Color)
Specification includes a Sequence Listing.

CLiCK in Dissociated Rat Cortical Neurons

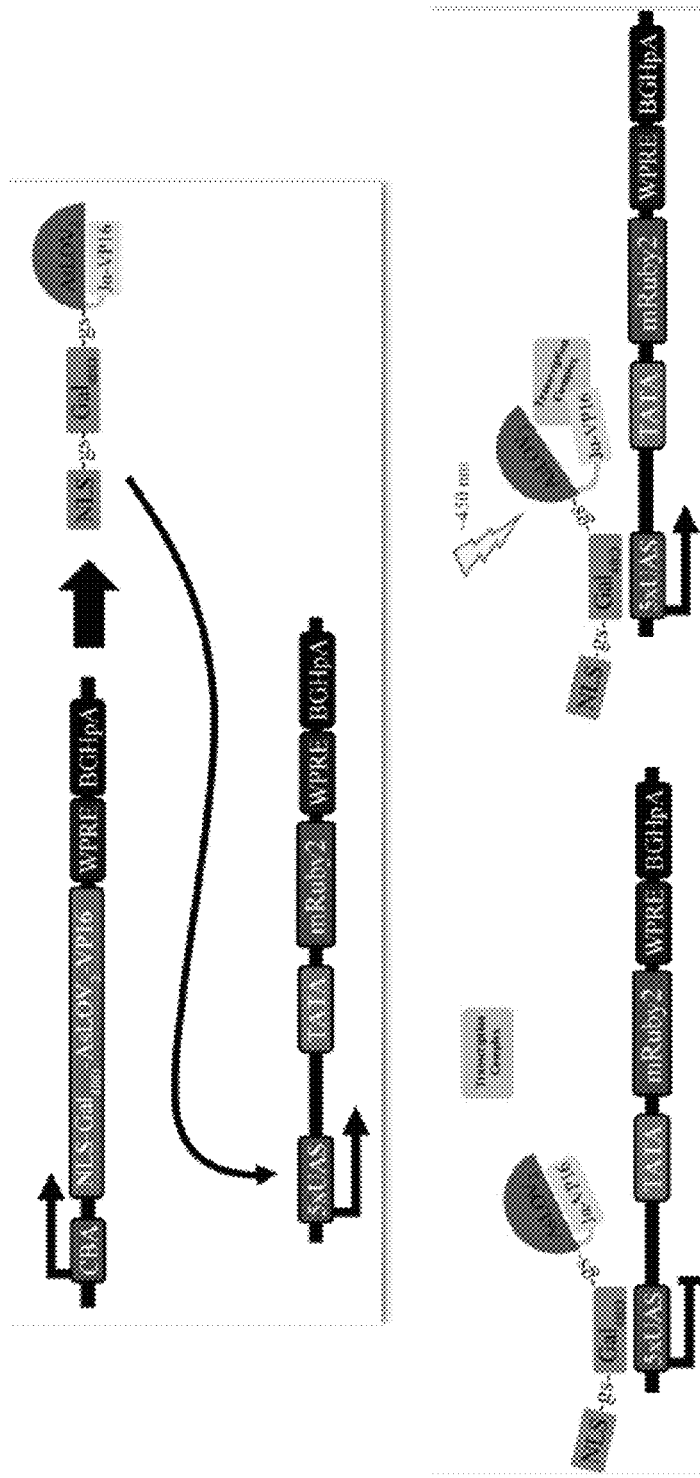
FIG. 14 (contd)

FIG. 19E

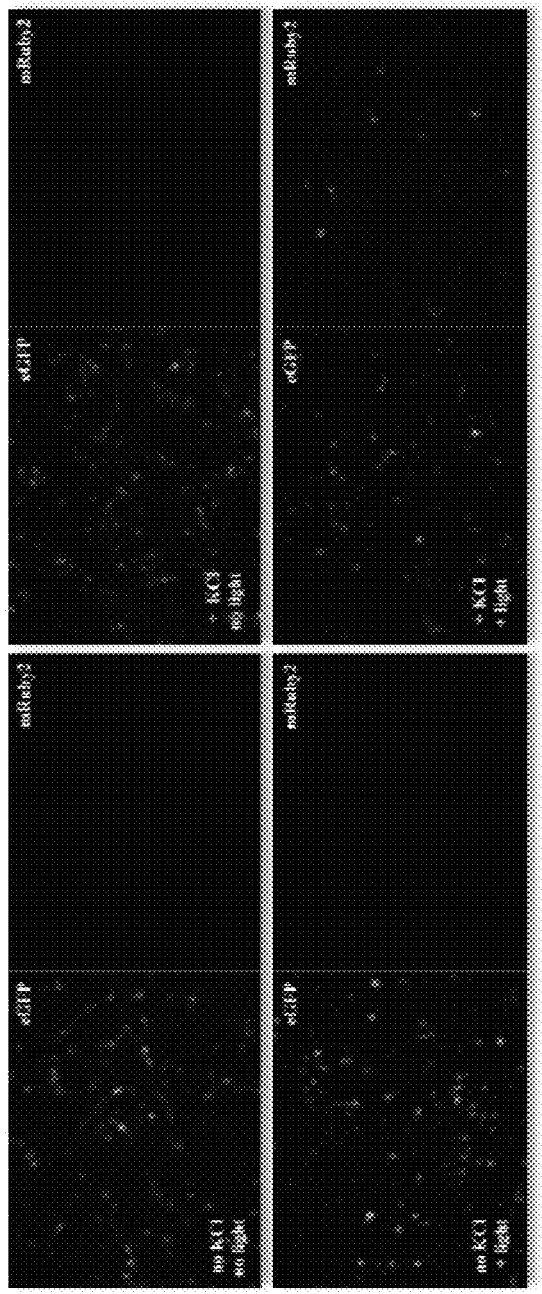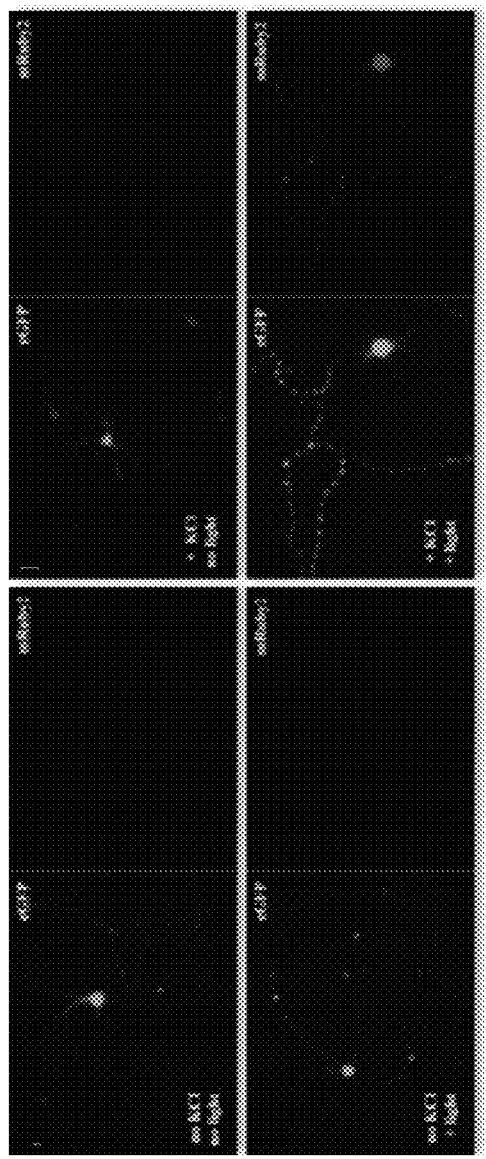
FIG. 19F

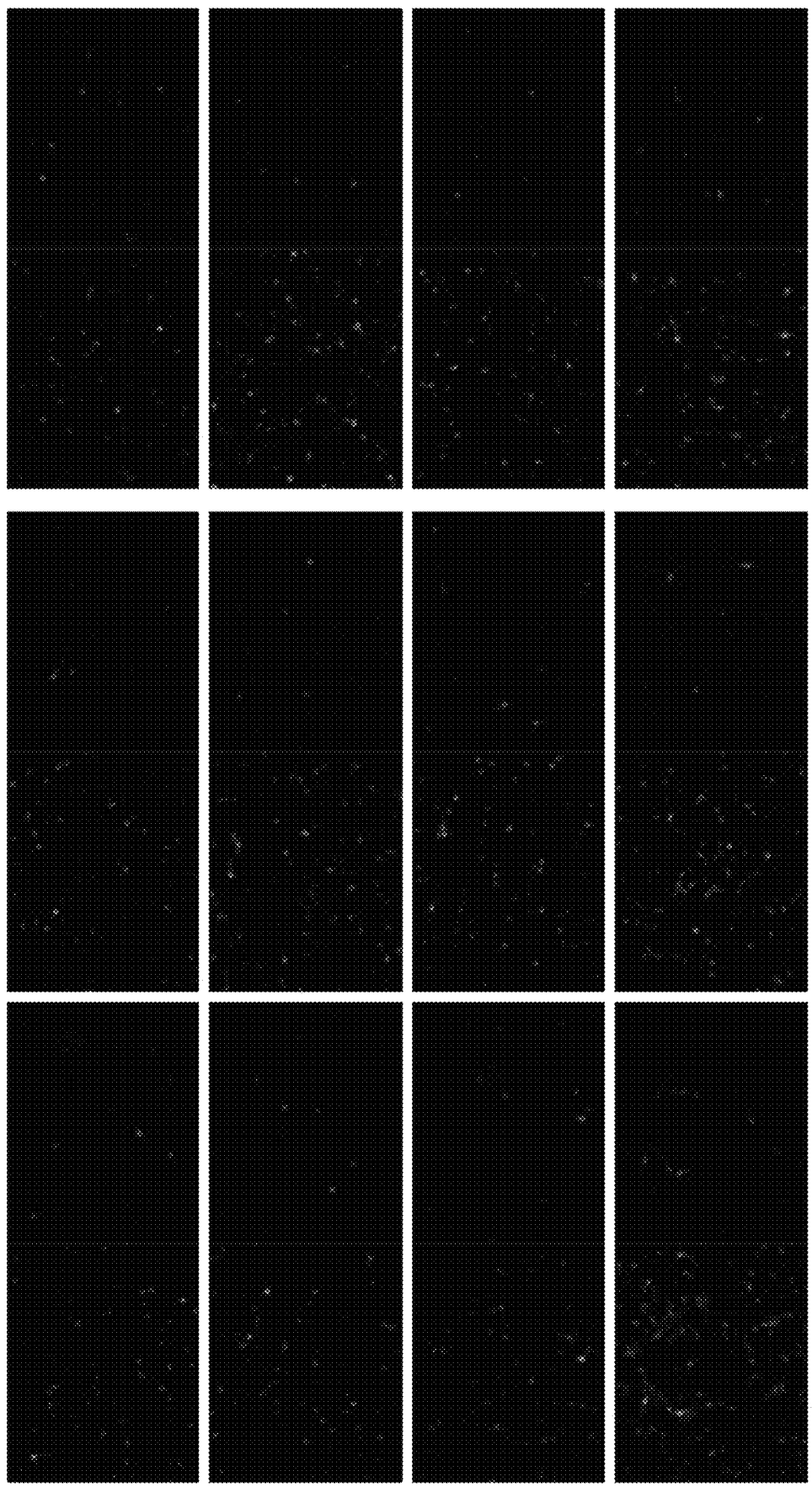
FIG. 19F (contd.)

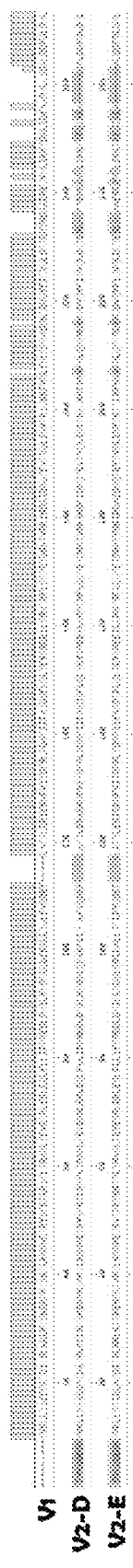

23B.

V1: 259AAs; MW = 29982.30 Da

MVKLLSSIEQACDICRLKKLKCSKEKPKCAKCLKNNWECRYSPKTKRSPLTRAHLTEVESRLERLEQLFLLIFPREDLDMILKMDSLQDIKALLTGLFVQDEFLATTLERIEKNFVITDPRLPDNPIIFA
SDSFLQLTEYSREEILGRNCRFLQGPETDRATVRKIRDAIDNQTEVTVQLINYTKSGKKFWNLFHLQPMRDQKGDVQYFIGVQLDGTEHVRDAAEREGVMLIKKTDALIDFAADMLGSDALD
DFDLDML*

V2-D: 268AAs; MW = 30868.14 Da

MDYKDDDDKMVKLLSSIEQACDICRLKKLKCSKEKPKCAKCLKNNWECRYSPKTKRSPLTRAHLTEVESRLERLEQLFLLIFPREDLDMILKMDSLQDIKALLTGLFVQDEFGGGSLATTLERIEK
NFVITDPRLPDNPIIFASDSFLQLTEYSREEILGRNCRFLQGPETDRATVRKIRDAIDNQTEVTVQLINYTKSGKKFWNVFHLQPMRDYKGDVQYFIGVQLDGTERLHGAAEREAVCLIKKTAFQI
AEAADALDDFDLDML*

V2-E: 266AAs; MW = 30681.98 Da

MDYKDDDDKMVKLLSSIEQACDICRLKKLKCSKEKPKCAKCLKNNWECRYSPKTKRSPLTRAHLTEVESRLERLEQLFLLIFPREDLDMILKMDSLQDIKALLTGLFVQDEFGGGSLATTLERIEK
NFVITDPRLPDNPIIFASDSFLQLTEYSREEILGRNCRFLQGPETDRATVRKIRDAIDNQTEVTVQLINYTKSGKKFWNVFHLQPMRDYKGDVQYFIGVQLDGTERLHGAAEREAVCLIKKTAFQI
AEAALDDFDLDML*

```
                        SEQUENCE LISTING

<160> NUMBER OF SEQ ID NOS: 15

<210> SEQ ID NO 1
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: a, c, t, g, unknown or other

<400> SEQUENCE: 1 rngtcarrg                                                             9

<210> SEQ ID NO 2
<211> LENGTH: 11
<212> TYPE: PRT
<213> ORGANISM: Herpes simplex virus

<400> SEQUENCE: 2

Asp Ala Leu Asp Asp Phe Asp Leu Asp Met Leu
1               5                   10

<210> SEQ ID NO 3
<211> LENGTH: 25
<212> TYPE: PRT
<213> ORGANISM: Avena sativa

<400> SEQUENCE: 3

Asp Ala Ala Glu Arg Glu Gly Val Met Leu Ile Lys Lys Thr Ala Glu
1               5                   10                  15

Asn Ile Asp Glu Ala Ala Lys Glu Leu
            20                  25

<210> SEQ ID NO 4
<211> LENGTH: 24
<212> TYPE: PRT
<213> ORGANISM: Herpes simplex virus

<400> SEQUENCE: 4

Asp Ala Leu Asp Asp Phe Asp Leu Asp Met Leu Gly Ser Asp Ala Leu
1               5                   10                  15

Asp Asp Phe Asp Leu Asp Met Leu
            20

<210> SEQ ID NO 5
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ala Ala Glu Arg Glu Gly Val Met Leu Ile Lys Lys Thr Asp Ala
1               5                   10                  15

Leu Ile Asp Phe Ala Ala Asp Met Leu Gly Ser Asp Ala Leu Asp Asp
```

```
                20                  25                  30

Phe Asp Leu Asp Met Leu
        35

<210> SEQ ID NO 6
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Ala Ala Glu Arg Glu Gly Val Met Leu Ile Lys Lys Thr Ala Glu
1               5                   10                  15

Asn Ile Asp Ala Ala Ala Asp Phe Asp Leu Asp Met Leu
            20                  25

<210> SEQ ID NO 7
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Asp Ala Ala Glu Arg Glu Gly Val Met Leu Ile Lys Lys Thr Ala Glu
1               5                   10                  15

Asn Ile Asp Glu Ala Ala Asp Ala Leu Asp Asp Phe Asp Leu Asp Met
            20                  25                  30

Leu

<210> SEQ ID NO 8
<211> LENGTH: 259
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Met Val Lys Leu Leu Ser Ser Ile Glu Gln Ala Cys Asp Ile Cys Arg
1               5                   10                  15

Leu Lys Lys Leu Lys Cys Ser Lys Glu Lys Pro Lys Cys Ala Lys Cys
            20                  25                  30

Leu Lys Asn Asn Trp Glu Cys Arg Tyr Ser Pro Lys Thr Lys Arg Ser
        35                  40                  45

Pro Leu Thr Arg Ala His Leu Thr Glu Val Glu Ser Arg Leu Glu Arg
    50                  55                  60

Leu Glu Gln Leu Phe Leu Leu Ile Phe Pro Arg Glu Asp Leu Asp Met
65                  70                  75                  80

Ile Leu Lys Met Asp Ser Leu Gln Asp Ile Lys Ala Leu Leu Thr Gly
                85                  90                  95

Leu Phe Val Gln Asp Glu Phe Leu Ala Thr Thr Leu Glu Arg Ile Glu
            100                 105                 110

Lys Asn Phe Val Ile Thr Asp Pro Arg Leu Pro Asp Asn Pro Ile Ile
        115                 120                 125

Phe Ala Ser Asp Ser Phe Leu Gln Leu Thr Glu Tyr Ser Arg Glu Glu
    130                 135                 140
```

```
Ile Leu Gly Arg Asn Cys Arg Phe Leu Gln Gly Pro Glu Thr Asp Arg
145                 150                 155                 160

Ala Thr Val Arg Lys Ile Arg Asp Ala Ile Asp Asn Gln Thr Glu Val
                165                 170                 175

Thr Val Gln Leu Ile Asn Tyr Thr Lys Ser Gly Lys Lys Phe Trp Asn
            180                 185                 190

Leu Phe His Leu Gln Pro Met Arg Asp Gln Lys Gly Asp Val Gln Tyr
        195                 200                 205

Phe Ile Gly Val Gln Leu Asp Gly Thr Glu His Val Arg Asp Ala Ala
    210                 215                 220

Glu Arg Glu Gly Val Met Leu Ile Lys Lys Thr Asp Ala Leu Ile Asp
225                 230                 235                 240

Phe Ala Ala Asp Met Leu Gly Ser Asp Ala Leu Asp Asp Phe Asp Leu
                245                 250                 255

Asp Met Leu

<210> SEQ ID NO 9
<211> LENGTH: 268
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Tyr Lys Asp Asp Asp Lys Met Val Lys Leu Leu Ser Ser
1               5                   10                  15

Ile Glu Gln Ala Cys Asp Ile Cys Arg Leu Lys Lys Leu Lys Cys Ser
                20                  25                  30

Lys Glu Lys Pro Lys Cys Ala Lys Cys Leu Lys Asn Asn Trp Glu Cys
            35                  40                  45

Arg Tyr Ser Pro Lys Thr Lys Arg Ser Pro Leu Thr Arg Ala His Leu
        50                  55                  60

Thr Glu Val Glu Ser Arg Leu Glu Arg Leu Glu Gln Leu Phe Leu Leu
65                  70                  75                  80

Ile Phe Pro Arg Glu Asp Leu Asp Met Ile Leu Lys Met Asp Ser Leu
                85                  90                  95

Gln Asp Ile Lys Ala Leu Leu Thr Gly Leu Phe Val Gln Asp Glu Phe
            100                 105                 110

Gly Gly Gly Gly Ser Leu Ala Thr Thr Leu Glu Arg Ile Glu Lys Asn
        115                 120                 125

Phe Val Ile Thr Asp Pro Arg Leu Pro Asp Asn Pro Ile Ile Phe Ala
    130                 135                 140

Ser Asp Ser Phe Leu Gln Leu Thr Glu Tyr Ser Arg Glu Glu Ile Leu
145                 150                 155                 160

Gly Arg Asn Cys Arg Phe Leu Gln Gly Pro Glu Thr Asp Arg Ala Thr
                165                 170                 175

Val Arg Lys Ile Arg Asp Ala Ile Asp Asn Gln Thr Glu Val Thr Val
            180                 185                 190

Gln Leu Ile Asn Tyr Thr Lys Ser Gly Lys Lys Phe Trp Asn Val Phe
        195                 200                 205

His Leu Gln Pro Met Arg Asp Tyr Lys Gly Asp Val Gln Tyr Phe Ile
    210                 215                 220

Gly Val Gln Leu Asp Gly Thr Glu Arg Leu His Gly Ala Ala Glu Arg
225                 230                 235                 240
```

```
Glu Ala Val Cys Leu Ile Lys Lys Thr Ala Phe Gln Ile Ala Glu Ala
                245                 250                 255

Ala Asp Ala Leu Asp Asp Phe Asp Leu Asp Met Leu
        260                 265
```

<210> SEQ ID NO 10
<211> LENGTH: 266
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Met Asp Tyr Lys Asp Asp Asp Lys Met Val Lys Leu Leu Ser Ser
1               5                   10                  15

Ile Glu Gln Ala Cys Asp Ile Cys Arg Leu Lys Lys Leu Lys Cys Ser
                20                  25                  30

Lys Glu Lys Pro Lys Cys Ala Lys Cys Leu Lys Asn Asn Trp Glu Cys
            35                  40                  45

Arg Tyr Ser Pro Lys Thr Lys Arg Ser Pro Leu Thr Arg Ala His Leu
    50                  55                  60

Thr Glu Val Glu Ser Arg Leu Glu Arg Leu Glu Gln Leu Phe Leu Leu
65                  70                  75                  80

Ile Phe Pro Arg Glu Asp Leu Asp Met Ile Leu Lys Met Asp Ser Leu
                85                  90                  95

Gln Asp Ile Lys Ala Leu Leu Thr Gly Leu Phe Val Gln Asp Glu Phe
                100                 105                 110

Gly Gly Gly Gly Ser Leu Ala Thr Thr Leu Glu Arg Ile Glu Lys Asn
            115                 120                 125

Phe Val Ile Thr Asp Pro Arg Leu Pro Asp Asn Pro Ile Ile Phe Ala
    130                 135                 140

Ser Asp Ser Phe Leu Gln Leu Thr Glu Tyr Ser Arg Glu Glu Ile Leu
145                 150                 155                 160

Gly Arg Asn Cys Arg Phe Leu Gln Gly Pro Glu Thr Asp Arg Ala Thr
                165                 170                 175

Val Arg Lys Ile Arg Asp Ala Ile Asp Asn Gln Thr Glu Val Thr Val
                180                 185                 190

Gln Leu Ile Asn Tyr Thr Lys Ser Gly Lys Lys Phe Trp Asn Val Phe
            195                 200                 205

His Leu Gln Pro Met Arg Asp Tyr Lys Gly Asp Val Gln Tyr Phe Ile
    210                 215                 220

Gly Val Gln Leu Asp Gly Thr Glu Arg Leu His Gly Ala Ala Glu Arg
225                 230                 235                 240

Glu Ala Val Cys Leu Ile Lys Lys Thr Ala Phe Gln Ile Ala Glu Ala
                245                 250                 255

Ala Leu Asp Asp Phe Asp Leu Asp Met Leu
            260                 265
```

<210> SEQ ID NO 11
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Gly Ala Ala Glu Arg Glu Ala Val Cys Leu Ile Lys Lys Thr Ala Phe
1               5                   10                  15

Gln Ile Ala Glu Ala Ala
            20

<210> SEQ ID NO 12
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Ala Asn Leu Phe Gln Leu Pro Gln Gln Thr Gln Gly Ala Leu Leu
1               5                   10                  15

Thr Ser Gln Pro
            20

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Ala Asp Met Leu Gly Ser Asp Ala Leu Asp Asp Phe Asp Leu Asp
1               5                   10                  15

Met Leu

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Asp Ala Leu Asp Asp Phe Asp Leu Asp Met Leu
1               5                   10

<210> SEQ ID NO 15
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Leu Asp Asp Phe Asp Leu Asp Met Leu
1               5                   10
```

OPTO-GENETIC MODULATOR

CROSS-REFERENCE TO RELATED APPLICATIONS

This application claims benefit under 35 U.S.C. § 119(e) of U.S. provisional application 62/464,859, filed Feb. 28, 2017, the content of which is incorporated herein by reference in its entirety.

GOVERNMENT SUPPORT

This invention was made with Government Support under Contract No. MH061492 and Contract No. NS051710 awarded by the National Institutes of Health (NIH). The Government has certain rights in the invention.

SEQUENCE LISTING

The instant application contains a Sequence Listing which has been submitted electronically in ASCII format and is hereby incorporated by reference in its entirety. Said ASCII copy, created on Apr. 3, 2018, is named 701586-088922-US_SL.txt and is 11,288 bytes in size.

TECHNICAL FIELD

The present invention relates generally to systems, compositions, and methods for monitoring and/or modulating gene expression.

BACKGROUND OF THE INVENTION

Currently, the precision at which identification and interaction with neural circuits driving naturalistic behaviors happens does not match the timescale at which those behaviors occur. Though progress has been made by way of observational approaches, there lacks a precise approach to experimentally interact with behaviorally distinct neural circuits in mammalian brain tissue. An ability to identify, isolate, and perturb distinct transient neural circuits in vivo would revolutionize the fundamental understanding of how neural circuits interact to encode information in the brain, bringing the field from observation to causation.

SUMMARY OF THE INVENTION

To characterize and understand the dynamics of neural circuits underlying discrete, complex behaviors, experimental tools that are highly selective in space and time while preserving the underlying network in which they exist are needed. Currently, the precision at which we can identify and interact with neural circuits driving naturalistic behaviors does not match the timescale at which those behaviors occur. Though we have made progress by way of observational approaches, there lacks a precise approach to experimentally interact with behaviorally distinct neural circuits in mammalian brain tissue. Applications of current technologies are limited by poor activity-dependent precision, superfluously evoking large networks of neurons indiscriminate of their activity during a given behavior. Advancing the precision at which transient neural circuits can be isolated and interacted with within behavioral timescales, as described herein, provides unprecedented opportunities for exploring the fundamental architecture of behavior in the brain. An ability to identify, isolate, and perturb distinct transient neural circuits in vivo can revolutionize the fundamental understanding of how neural circuits interact to encode information in the brain, bringing the field from observation to causation.

Further, to the extent that the systems, compositions and methods described herein permit the rapid optical induction of reporter or effector gene expression in a cell- or tissue-type specific manner that is also dependent upon a physiological state or response, the technology described herein can be adapted to achieve optical and cellular activity-dependent regulation of a reporter or effector in other cell types. Thus, the technology can be adapted to confer optical and activity-dependent control over expression of a reporter or effector in essentially any activatable cell type. As non-limiting examples, in addition to neurons, activity-dependent optical regulation can also be conferred upon, e.g., muscle cells, secretory cells, endocrine cells and/or immune cells.

For simplicity, and by way of example, the technology is described herein as applied in the neuronal context, but it should be understood that such description is non-limiting with regard to cell or tissue types useful with the described technology. Similarly, this disclosure refers at various places to a system involving a physiological response element and exemplifies a Ca2+ responsive element and factor DREAM/DRE. The Ca2+ responsive system is referred to at points as a "CLiCK" system. It should be understood that the Ca2+ responsive system and factor are exemplary, and that other physiological elements and factors can be readily adapted for similar use. That is, reference to the systems and methods described herein as a "CLiCK" system should not be viewed as limited to Ca2+ responsive or Ca2+ dependent, and other responsive element/factor combinations can be used, unless otherwise specified. In one embodiment, however, a CLiCK system is a Ca2+ responsive or Ca2+ dependent system.

The long-term implications of the technologies presented here are the development of a transformative genetic regulatory tool for in vivo applications, including broadly spanning behavioral, cognitive, and systems neuroscience. As used herein, "CLiCK" or "Ca2+ Light Coincidence Knock-in/out" refers to a genetic regulatory system for regulating genetic expression in transiently active neurons within behaviorally relevant windows of time (<1 sec). Bringing together techniques in genetic engineering, plant biology, and neuroscience in a novel manner, CLiCK has been designed to control the expression of a gene-of-interest (e.g., Cre, fluorophores, channelrhodopsins, shRNAs, CRISPR, TALEN, etc.) through the co-occurrence of cell activity and the uncaging of a light-switchable transcription factor. Only with the co-occurrence of light (experimentally driven) and cell activity does gene transcription occur. CLiCK overcomes the current limitation of poor temporal resolution (hours long) of activity-dependent specificity in current approaches through its incorporation of gating components that operate at the millisecond timescale. CLiCK incorporates all the attributes of genetics, such as region and cell type selectivity. The technologies described herein can be extended to any region of the central and/or peripheral nervous systems where characterization of neural circuits driving complex behaviors are of interest. Development of the systems described herein are useful for catalyzing new forms of research in the scientific exploration of brain and behavior.

The CLiCK technology described herein overcomes the critical limitation of poor experimental temporal specificity of gene expression by uniquely combining the fast gating mechanisms of a phototropin to a strong transcriptional activator and functionally localizing it to a downstream target gene. By drastically advancing the temporal resolution at which experimental windows of time can be set, naturalistic behaviors, which are typically part of a larger set of behaviors occurring within a small window of time, can be isolated. Complimentary temporal precision of signal transduction is needed to maintain temporal specificity of gene expression. Previous techniques have used immediate-early-genes (IEGs) to turn on a gene by cellular activity, however, this take minutes to hours and therefore does not provide the level of temporal sensitivity needed. While optical applications of Ca2+ indicators have benefited from the fast, direct transduction of neural activity by Ca2+ transients, Ca2+ transients have not been capitalized on in driving activity-dependent gene expression. As demonstrated herein, CLiCK incorporates the first ever application of a gene regulatory system that is directly driven by Ca2+ transients. CLiCK, forgoing all intermediate signaling molecules involved in IEGs and employing direct Ca2+ regulation of gene expression, in combination with the high temporal control of experimental windowing, can bring forth a new wave of research in neuroscience and other disciplines.

As demonstrated herein, CLiCK has a temporal precision of activity-dependent gene expression that is orders of magnitude finer than what is currently available. The current state of the field offers temporal precision of 16 hours. At this resolution, even simple behaviors cannot be isolated experimentally. CLiCK offers sub-second temporal precision which allows for the isolation and study of neural circuits underlying naturally occurring complex behaviors. The modular components of the CLiCK system are small enough to be packaged in either adeno-associated virus or lentivirus, making it flexible for use in a range of animal models. Additionally, CLiCK can be easily tailored to drive specific genes-of-interest in a cell-specific manner, making it a versatile tool for applications across a broad range of disciplines.

Variations of the CLiCK system described herein can be defined, in some embodiments, by the gene-of-interest that is being driven. For example, in some embodiments of the aspects described herein, a CLiCK-Labeler system is provided that only labels active neurons by using CLiCK-Label to drive the expression of a fluorescent protein like mRuby or eGFP. In some embodiments of the aspects described herein, a CLiCK-Reversible system is provided such that gene expression under CLiCK is reversible. In some embodiments of the aspects described herein, a CLiCK-Persistent system is provided such that a gene-of-interest is knocked-in a gene indefinitely using, for example, Cre and combining or breeding with any Cre-dependent models. In some embodiments of the aspects described herein, a CLiCK-Apoptosis system is provided that causes activity-dependent programmed cell death by driving a gene that activates the caspase 3 pathway. In some embodiments of the aspects described herein, a CLiCK-Therapeutics system is provided that delivers activity-dependent gene therapy.

Accordingly, in some aspects, provided herein are engineered systems comprising: (a) a control module comprising a nucleic acid sequence encoding a chimeric photosensitive transcription factor operably linked to a promoter, where the photosensitive transcription factor comprises: (i) a transcription activation domain; (ii) a sequence-specific DNA binding domain; and (iii) a photo-sensitive actuator domain which is activated by photoirradiation in a defined range of wavelengths; and (b) a physiologically responsive module comprising a nucleic acid sequence encoding a gene of interest operably linked to an inducible promoter comprising: i. a sequence element that binds the sequence-specific DNA binding domain of the photosensitive transcription factor, and ii. a physiological response element comprising a binding site for a physiological response factor, the binding of which factor is directly regulated by a physiological agent or condition; where expression of the gene of interest in a cell comprising the system requires the presence of both the physiological agent or condition and photoirradiation within the defined range of wavelengths.

In some embodiments of these aspects and all such aspects described herein, the physiological response element comprises a binding site for an activity-dependent or hormone-dependent physiological transcription factor.

In some embodiments of these aspects and all such aspects described herein, the activity-dependent or hormone-dependent physiological transcription factor comprises a transcriptional repressor.

In some embodiments of these aspects and all such aspects described herein, the control module and the physiologically responsive module are encoded on a single nucleic acid molecule.

In some embodiments of these aspects and all such aspects described herein, the transcription activation domain of the photosensitive transcription factor comprises a transcription activation domain of a transcription factor selected from the group consisting of Herpes Virus VP16, HIV TAT, yeast GAL4, GCN4 or HAP1, glucocorticoid receptor transcription activation domain, B-cell POU homeodomain protein Oct2, and plant Ap2.

In some embodiments of these aspects and all such aspects described herein, the sequence-specific DNA binding domain comprises a DNA binding domain of a transcription factor, restriction endonuclease or an engineered DNA binding domain that binds a desired DNA sequence.

In some embodiments of these aspects and all such aspects described herein, the sequence-specific DNA binding domain comprises one or more zinc finger domains.

In some embodiments of these aspects and all such aspects described herein, the sequence-specific DNA binding domain comprises the DNA-binding domain of a transcription factor selected from the group consisting of GAL4, GCN4, Thy1, Syn1, NSE/RU5', Agrp, Calb2, Camk2a, CcK, Chat, dlx6a and Emx1.

In some embodiments of these aspects and all such aspects described herein, the sequence-specific DNA binding domain is engineered to bind a desired sequence.

In some embodiments of these aspects and all such aspects described herein, the photosensitive actuator domain comprises a photoreceptor domain selected from the group consisting of a Light-Oxygen-Voltage (LOV) photoreceptor domain, an $LOV_2$ photoreceptor domain, a Cryptochrome (CRY) photoreceptor domain, Blue-light-using FAD (BLUF) photoreceptor domain, a Phytochrome (PHY) photoreceptor domain, and a UVR8 photoreceptor domain.

In some embodiments of these aspects and all such aspects described herein, the LOV photoreceptor domain comprises the *Avena sativa* phototropin $LOV_2$ photoreceptor domain.

In some embodiments of these aspects and all such aspects described herein, the physiological response element comprises a binding site for an activity-dependent transcriptional repressor.

In some embodiments of these aspects and all such aspects described herein, the activity-dependent transcriptional repressor comprises the downstream responsive element antagonist modulator (DREAM) repressor and the physiological response element comprises the DREAM response element (DRE).

In some embodiments of these aspects and all such aspects described herein, the physiological agent or condition comprises intranuclear calcium, and intranuclear calcium binds the DREAM repressor and causes dissociation of the repressor from the DRE.

In some embodiments of these aspects and all such aspects described herein, the system further comprises a nucleic acid construct encoding the DREAM repressor.

In some embodiments of these aspects and all such aspects described herein, the system transduces photoirradiation within the defined range of wavelengths with a temporal resolution of less than ten minutes.

In some embodiments of these aspects and all such aspects described herein, the system transduces photoirradiation within the defined range of wavelengths with a temporal resolution of less than one minute.

In some embodiments of these aspects and all such aspects described herein, where the system is in a cell in the presence of the intracellular marker of cellular activity, the system transduces photoirradiation within the defined range of wavelengths with a temporal resolution of less than one second.

In some embodiments of these aspects and all such aspects described herein, the system transduces photoirradiation within the defined range of wavelengths with a temporal resolution of less than 100 ms.

In some embodiments of these aspects and all such aspects described herein, the system transduces photoirradiation within the defined range of wavelengths with a temporal resolution of less than 10 ms.

In some embodiments of these aspects and all such aspects described herein, the photosensitive transcription factor is expressed and bound to the inducible promoter of the physiologically responsive module before photoirradiation within the defined range of wavelengths is provided.

In some embodiments of these aspects and all such aspects described herein, the expression of the control module is constitutive.

In some embodiments of these aspects and all such aspects described herein, the expression of the control module is under the control of a tissue- or cell-type specific promoter.

In some embodiments of these aspects and all such aspects described herein, the expression of the control module is under the control of an inducible promoter.

In some embodiments of these aspects and all such aspects described herein, the gene of interest encodes a reporter polypeptide, a toxin or a therapeutic polypeptide.

In some embodiments of these aspects and all such aspects described herein, the gene of interest encodes an endonuclease or an shRNA.

In some embodiments of these aspects and all such aspects described herein, the endonuclease comprises a sequence-specific endonuclease.

In some embodiments of these aspects and all such aspects described herein, the sequence-specific endonuclease comprises an RNA-guided endonuclease or a TALEN.

In some embodiments of these aspects and all such aspects described herein, the reporter polypeptide comprises an enzyme or a fluorescent polypeptide.

In some embodiments of these aspects and all such aspects described herein, the reporter polypeptide is engineered to comprise an element that destabilizes the reporter polypeptide.

In some embodiments of these aspects and all such aspects described herein, the reporter polypeptide is engineered to comprise a protease cleavage site that destabilizes the reporter polypeptide.

In some aspects, provided herein are nucleic acid constructs encoding a control module and a physiologically responsive module as described herein.

In some embodiments of these aspects and all such aspects described herein, the nucleic acid construct further comprises nucleic acid sequence encoding a repressor that binds the physiological response element and is directly inhibited by a physiological agent or condition.

In some embodiments of these aspects and all such aspects described herein, the physiological response element binds a physiological response factor that is directly regulated by a hormone or an activity-dependent agent.

In some embodiments of these aspects and all such aspects described herein, the physiological response factor binds intranuclear calcium.

In some aspects, provided herein are vectors comprising any of the nucleic acid constructs described herein.

In some embodiments of these aspects and all such aspects described herein, the vector comprises a plasmid, a cosmid, or a virus.

In some aspects, provided herein are cells comprising any of the vectors described herein.

In some embodiments of these aspects and all such aspects described herein, the cell is a neuron or a stem cell.

In some embodiments of these aspects and all such aspects described herein, the cell is in vitro.

In some embodiments of these aspects and all such aspects described herein, the cell is in vivo.

In some embodiments of these aspects and all such aspects described herein, the system further comprises a light source that delivers light within the defined range of wavelengths.

In some aspects, provided herein are transgenic non-human organisms comprising any of the systems described herein.

In some aspects, provided herein are nucleic acid molecules comprising: a module comprising nucleic acid sequence encoding a chimeric photosensitive transcription factor operably linked to a promoter, where the photosensitive transcription factor comprises: a transcription activation domain; a sequence-specific DNA binding domain; and a photo-sensitive actuator domain which is activated by photoirradiation in a defined range of wavelengths; and a module comprising nucleic acid sequence encoding a physiologically responsive module comprising a nucleic acid sequence encoding a gene of interest operably linked to an inducible promoter comprising: a sequence element that binds the sequence-specific DNA binding domain of the photosensitive transcription factor, and a physiological response element comprising a binding site for a physiological response factor, the binding of which factor is directly regulated by a physiological agent or condition; wherein, when the nucleic acid molecule is introduced to a cell, expression of the gene of interest in the cell requires the presence of both the physiological agent of condition and photoirradiation within the defined range of wavelengths.

In some embodiments of these aspects and all such aspects described herein, the nucleic acid molecules are comprised by a single nucleic acid construct.

In some embodiments of these aspects and all such aspects described herein, the physiological response element comprises a binding site for an activity-dependent or hormone-dependent physiological transcription factor.

In some embodiments of these aspects and all such aspects described herein, the activity-dependent or hormone-dependent physiological transcription factor comprises a transcriptional repressor and the physiological response element comprises a repressor binding element that binds the repressor.

In some embodiments of these aspects and all such aspects described herein, ehe nucleic acid molecule further comprises nucleic acid sequence encoding a repressor protein that binds the repressor binding element in a manner that is directly inhibited by the physiological agent or condition.

In some aspects, provided herein are nucleic acid molecules comprising: a nucleic acid sequence encoding a chimeric photosensitive transcription factor operably linked to a promoter, wherein the photosensitive transcription factor comprises a Herpes Virus VP-16 transactivation domain, a GAL4 DNA binding domain, and an *A. sativa* LOV photosensitive actuator domain; and a nucleic acid sequence encoding a gene of interest operably linked to an inducible promoter comprising at least one copy of a GAL4 UAS sequence and a DRE repressor binding element, wherein expression of the gene of interest in a cell comprising the system requires the presence of both intracellular calcium in the range of about 0.1 μM to about 5 μM and light in the range that activates the *A. sativa* photosensitive actuator domain.

In some embodiments of these aspects and all such aspects described herein, the nucleic acid molecules are comprised by a single nucleic acid construct.

In some embodiments of these aspects and all such aspects described herein, the inducible promoter comprises at least two copies of the DRE repressor binding element, e.g., at least three copies, at least four copies, at least five copies, at least six copies, or more.

In some aspects, provided herein are vectors comprising any of the nucleic acid molecules described herein.

In some embodiments of these aspects and all such aspects described herein, the vector comprises a plasmid, a cosmid, or a virus.

In some aspects, provided herein are cells comprising any of the vectors described herein.

In some embodiments of these aspects and all such aspects described herein, the cell is a neuron or a stem cell.

In some embodiments of these aspects and all such aspects described herein, the cell is in vitro. In some embodiments of these aspects and all such aspects described herein, the cell is in vivo.

In some aspects, provided herein are methods of monitoring or detecting cellular activity, such as neuronal activity, the method comprising: irradiating a cell, such as a neuron, comprising any of the systems described herein with photoirradiation within the defined range of wavelengths; and detecting expression of the gene of interest, wherein detection of the expression of the gene of interest indicates activity of the cell, such as a neuron.

In some embodiments of these aspects and all such aspects described herein, the method further comprises the step, before the step of irradiating the cell, such as a neuron, of introducing any of the systems described herein to the cell. In some embodiments of these aspects and all such aspects described herein, the system is introduced using a viral vector. In some embodiments of these aspects and all such aspects described herein, the cell, such as a neuron, is in culture.

In some embodiments of these aspects and all such aspects described herein, the cell, such as a neuron, is in vivo.

In some embodiments of these aspects and all such aspects described herein, the step of irradiating the cell comprises irradiation of the cell via an optical fiber.

In some embodiments of these aspects and all such aspects described herein, the physiological agent or condition comprises intranuclear calcium.

In some embodiments of these aspects and all such aspects described herein, the physiological response element comprises a downstream responsive element (DRE) that binds the downstream responsive element antagonist modulator (DREAM) repressor, and wherein intranuclear calcium binds the DREAM repressor and causes dissociation of the repressor from the DRE.

In some embodiments of these aspects and all such aspects described herein, the gene of interest comprises a fluorescent protein and detecting expression of the gene of interest comprises detecting fluorescence in the cell, such as a neuron.

In some aspects, provided herein are methods of expressing a gene of interest in a neuron in an activation-specific manner, the method comprising: introducing any of the systems described herein to a neuron, wherein the physiological response element comprises a downstream responsive element (DRE) that binds the downstream responsive element antagonist modulator (DREAM) repressor, and wherein intranuclear calcium binds the DREAM repressor and causes dissociation of the repressor from the DRE; and irradiating the neuron with light within the defined range of wavelengths, wherein the gene of interest is expressed in a neuronal activation-specific or activity-dependent manner.

In some embodiments of these aspects and all such aspects described herein, the gene of interest encodes a reporter polypeptide, a toxin or a therapeutic polypeptide.

In some embodiments of these aspects and all such aspects described herein, the gene of interest encodes an endonuclease or an shRNA. In some embodiments of these aspects and all such aspects described herein, the endonuclease comprises a sequence-specific endonuclease. In some embodiments of these aspects and all such aspects described herein, the sequence-specific endonuclease comprises an RNA-guided endonuclease or a TALEN.

Provided herein, in some aspects, are kits comprising any of the nucleic acids described herein, or any of the vectors described herein, or any of the cells described herein; and packaging and instruction materials therefor.

In some embodiments of these aspects and all such aspects described herein, the kits further comprise a cell. In some embodiments of these aspects and all such aspects described herein, the cell is a neuron or a stem cell.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 6, bottom, shows an embodiment of a persistent CLiCK system that is driving Cre which is targeted to inverted loxP sites which would flip the GOI (in this embodiment, mRuby) causing it to be expressed indefinitely.

FIG. 7C. Incorporating CLiCK into a dual-independent promoter vector optimizes the co-dependencies of the two expression cassettes. sMAP8: synthetic matrix attachment region insulator, TKpA: tymidine kinase polyA, 2A: 2A selfcleaving peptide, 3×HA-NLS-Gal4BD-AsLOV2-VP16: fusion protein defining CLiCK$_{TF}$, CMV: cytomegalovirus promoter, cHS4: insulator sequence from chicken hypersensitive site 4, Tactb: G-rich pause sequence from beta-actin gene, SPA+S: synthetic polyA plus spacer sequence, mRuby2: fluorophore, DRE: downstream regulator element binding sequence, TATA: TATA box, 5×UAS: 5× repeat of Gal4 upstream activation sequence.

FIG. 14 discloses SEQ ID NOs. 3-5, 3, 2, 6, 3, 2, and 7, respectively, in order of appearance.

Figure 19E:
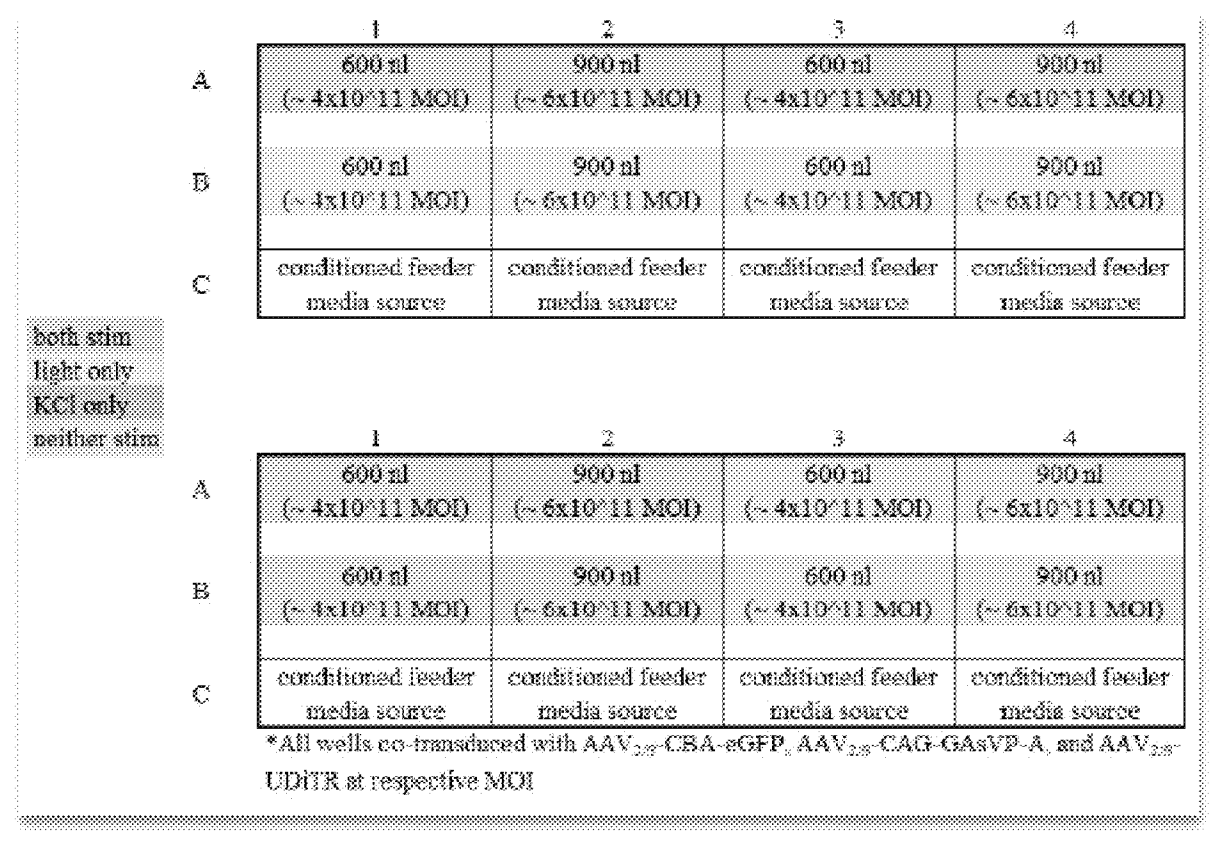

FIGS. 19A-19F show results from an in vitro neuron assay using an embodiment of the CLiCK optogenetic system. 19A-19D. Schematics of an embodiment of the CLiCK optogenetic system. 19E-19F. 0 DIV dissociated primary cortical neurons from E15 mice. 3 DIV neurons triple transduce AAV2/9-CBA-CLiCKTF, AAV2/9-CLiCK-Act, and AAV2/9-CAG-eGFP (Cells were kept in light-tight containers immediately following transfection and handled under red light. 7 DIV neurons assayed under conditions of: 1. Light only: 1 μM TTX 45 mins prior exposure to light to block spontaneous spiking. Brief (~5 sec) exposure to blue light. 2. KCl only: 40 mMKCl applied to well media. Quickly exchanged with previously conditioned media (+1 μM TTX). 3. Neither: 1 μM TTX 45 mins prior exposure to light to block spontaneous spiking. 4. KCl & Light: Incubated for 4 hrs. Imaging was performed using a Nikon inverted microscope Acquisition settings calibrated to control condition and kept constant across all conditions.

FIGS. 23A-23B show amino acid alignments and sequences. FIG. 23A. Amino acid alignments of optimized versions or embodiments of light-gated transcription factors (SEQ ID NOs. 8-10, respectively, in order of appearance). Top row indicates points of alignment of the proteins where a solid bar is an aligned AA and a gap indicates mutations. The original (V1) AA sequence is used as the template for which optimized versions (V2-D and V2-E) are aligned to.

Points of mutations are highlighted. AAs are coded by RasMol scheme. Numbers along the axis indicate AA count. FIG. 23B. Amino acid sequences for light-gated transcription versions V1, V2-D, and V2-E (SEQ ID NOs. 8-10, respectively, in order of appearance). Number of amino acids and molecular weight provided for each protein.

FIG. 24A. Functional schematic of CLiCK. FIG. 24B. Protein assay showing no difference between the amount of protein made between positive controls [JVA, JVD, and NE] and experimental proteins [VA, VD, and VE] indicating differences in read-outs are not due to differences in protein expression level. FIG. 24C. Amino acid sequences of negative control [Jα] and four light-gated activation domains [iOA, iVA, iVD, and iVE] (SEQ ID NOS. 11-15, respectively, in order of appearance). FIG. 24D. Exemplary fluorescent read-out of embodiment—VE in rat primary culture E18 dissociated cortical neurons 21 DIV. Left column shows differential interference contrast images of the cultures, middle column shows transfection marker (eGFP), and right column shows expression of reporter (mRuby). Neurons do not express the mRuby by activity or light alone. The neuron must be activity while exposed to light for the mRuby to be expressed. 20 mM+KCl was used to induce neural spiking. A brief LED blue light pulse was used for light exposure (~5 mW, 1 second). FIG. 24E. Percent of neurons co-expression the transfection marker (eGFP) and the functional reporter mRuby at pre-stimulus, +KCl only, light only, simultaneous +KCl and light, and positive control. Each graph corresponds to the activation domain denoted above the graph.

DETAILED DESCRIPTION

Figure 1:
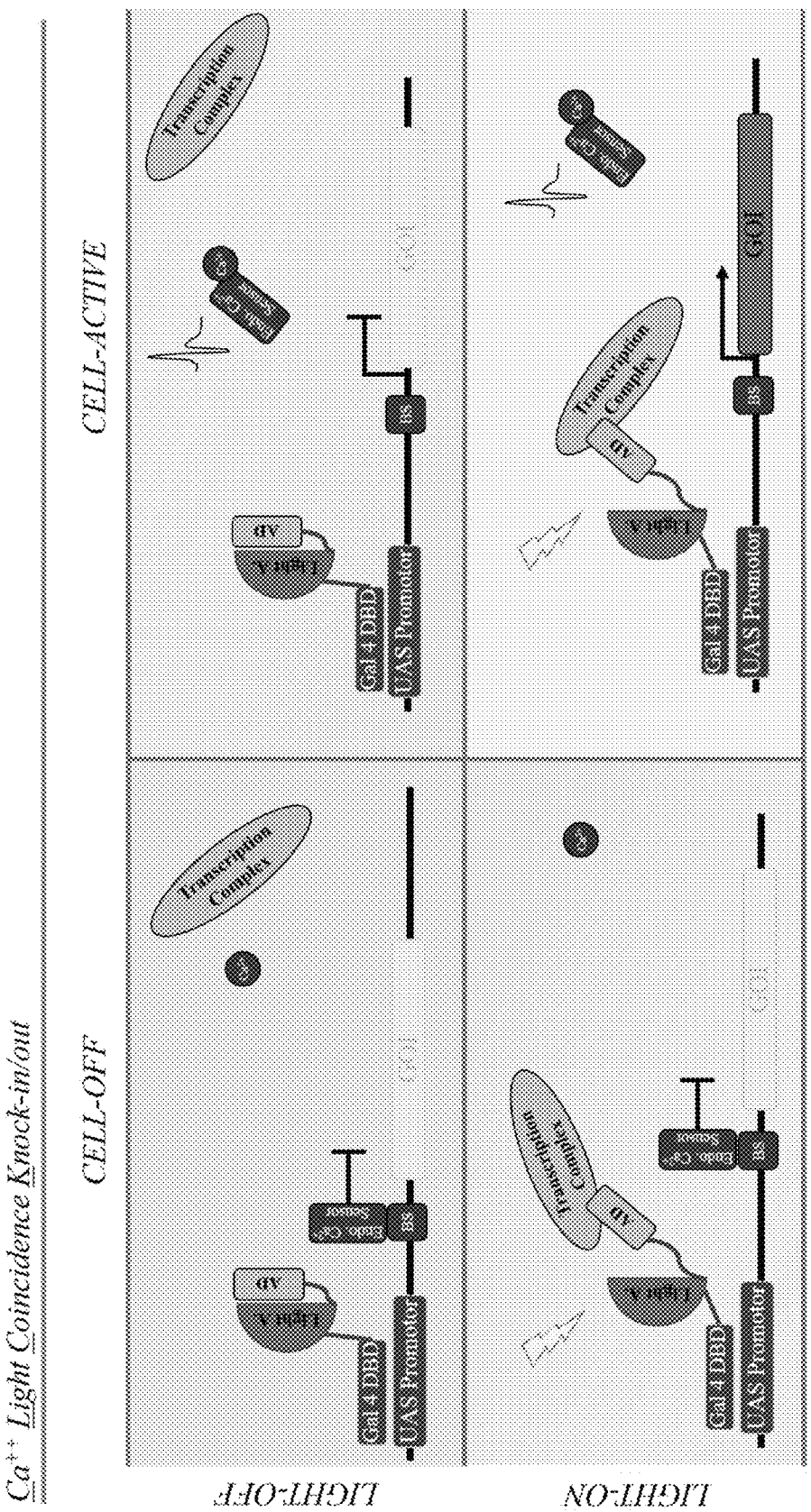
FIG. 1 depicts a schematic of an embodiment of the CLiCK optogenetic system described herein.
Figures 2A, 2B, 2C, 2D, 2E:
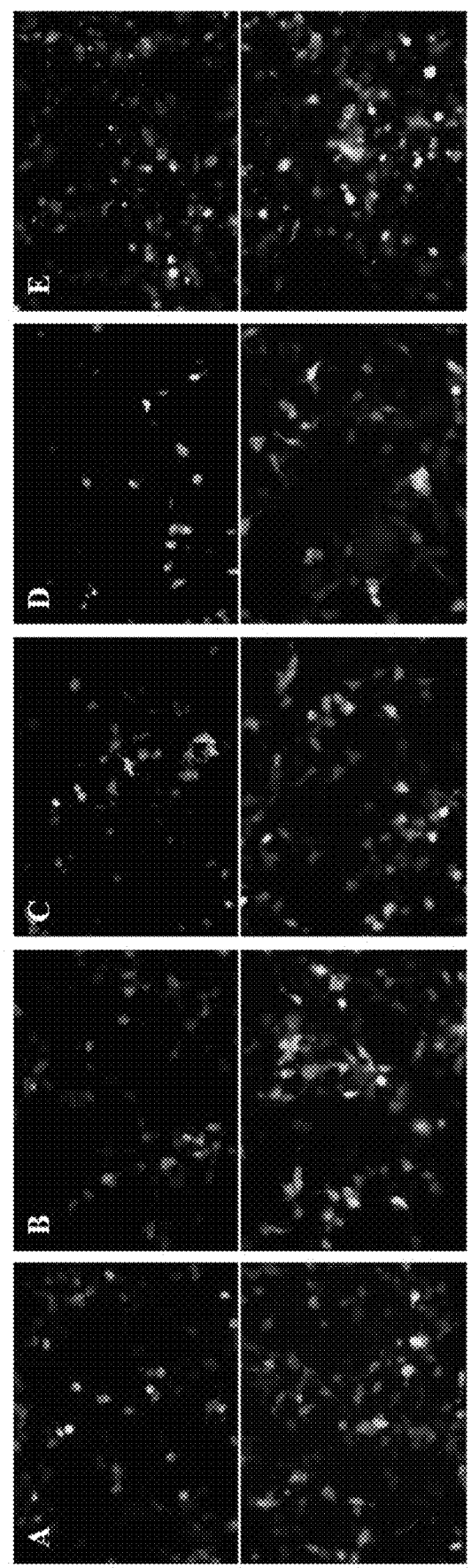
FIGS. 2A-2E shows photo-activation of CLiCK in HEK cells. HEK lack the endogenous Ca2+ inhibitory molecule DREAM and therefore express the GOI (mRuby) with light stimulation only. HEK cells were transfected with a transfection reporter gene (yellow) and either CLiCK (top row) or a positive control set of plasmids. Positive controls consisted of two plasmids, a non-light sensitive transactivator and its downstream target, mRuby. Following 2×1 second stimulation with 450 nm wavelength light, mRuby was observed for up to 8 hours in CLiCK transfected cells (2A-2D, top). After 48 hours, mRuby was no longer observable demonstrating the reversibility of CLiCK (2E, top). All conditions contained a constitutive transfection reporter (yellow).
Figure 3:
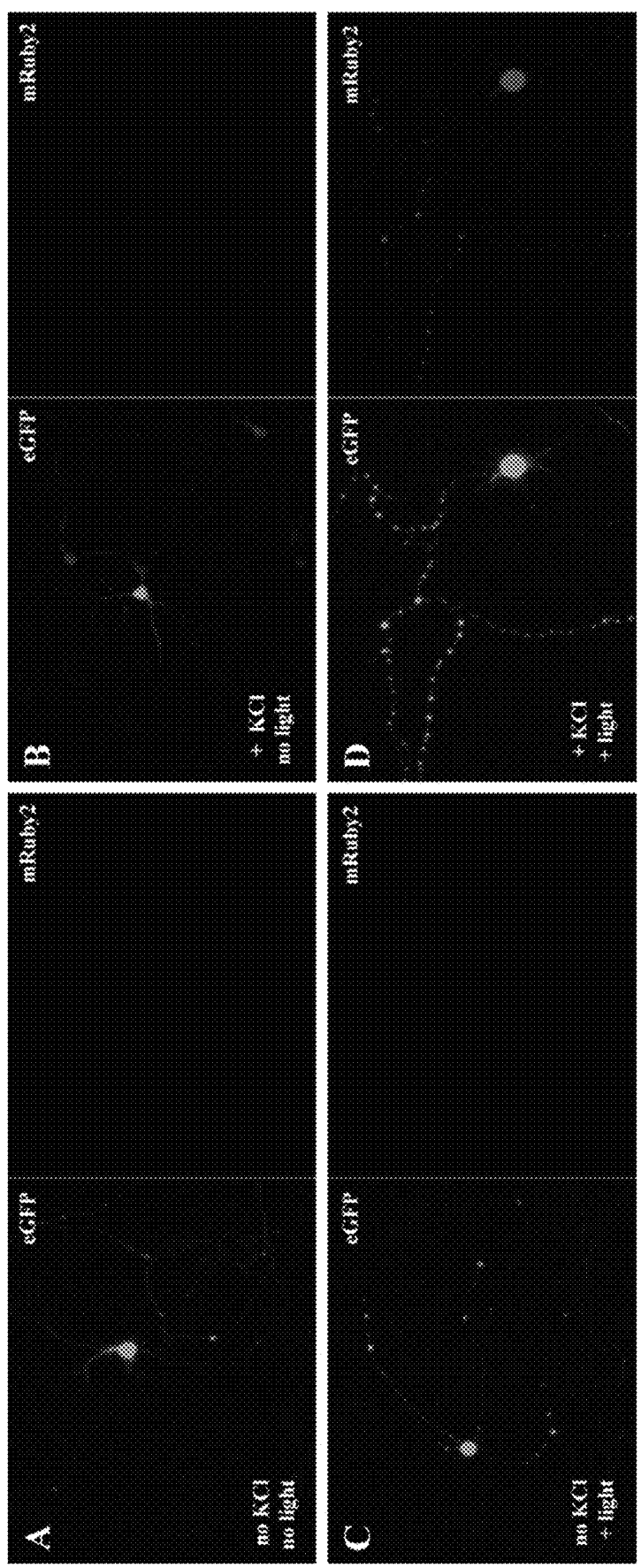
FIG. 3 shows CLiCK in Dissociated Rat Cortical Neurons. Dissociated E18 rat cortical cells were transfected at 9 DIV with a transfection marker (yellow) and CLiCK. Cells were assayed 48 hours following transfection (11 DIV). CLiCK was used to drive the expression of mRuby (red) following co-occurrence of spiking and light stimulus. Spiking was induced through quick bath application of 90 mM KCl. A 450 peak nm light was used for light stimulus. Spontaneous spiking in neurons was blocked using 1 uM TTX. Cells were kept in light tight containers and stored in an incubator following transfection and for 4 hours following an assay, after which point they were imaged. mRuby was only observed in neurons that simultaneously received KCl and light stimulation (bottom right panel). This selective expression of mRuby was observed up to 48 hours post-stim (FIG. 5).
Figure 4:
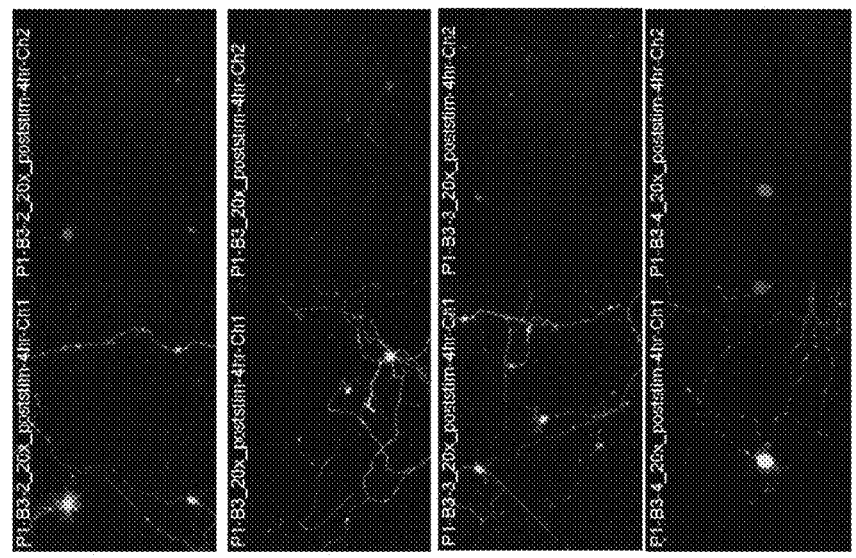
FIG. 4 shows additional examples of mRuby2 expression in E18 dissociated rat cortex primary neurons following co-light-KCl induced spiking assay (left). (Right) Assay design.
Figure 5:
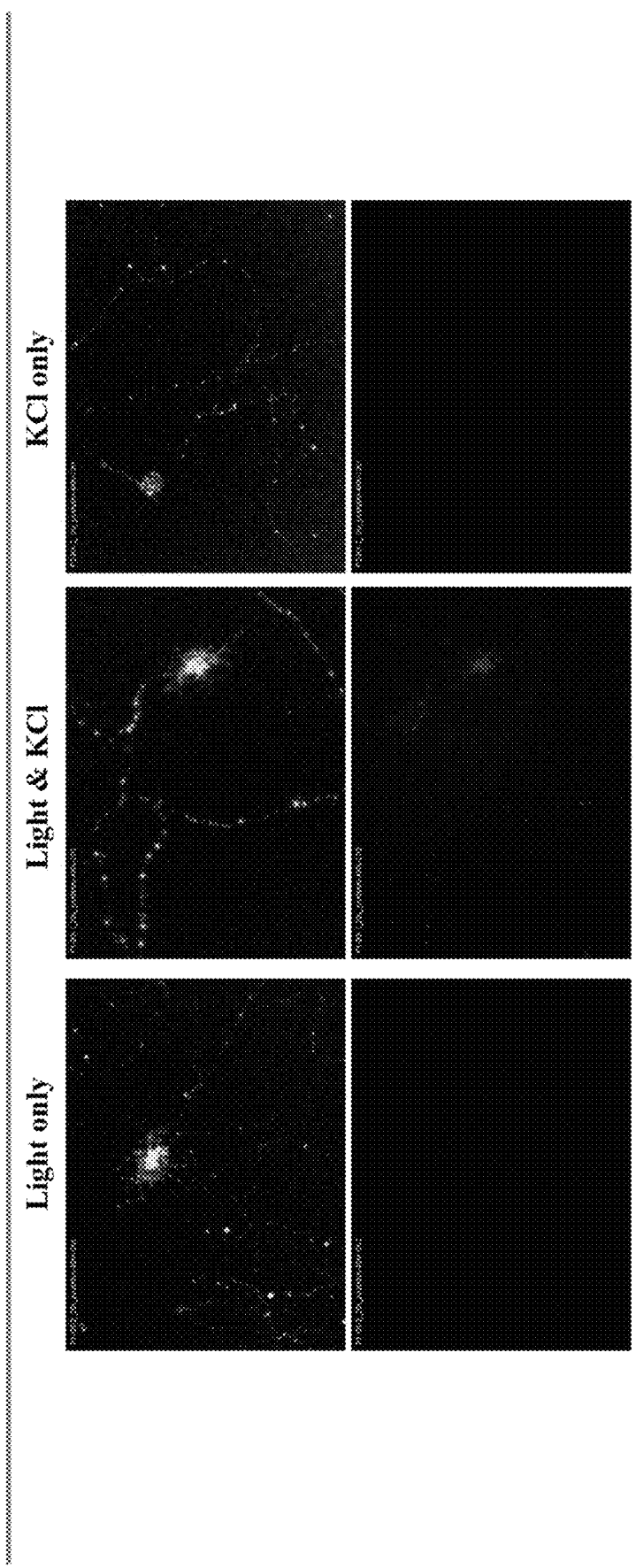
FIG. 5 shows CLiCK in Dissociated Rat Cortical Neurons after 48 hours post-stimuli. Only under co-light and –KCl induced spiking is mRuby2 expressed (middle).
Figure 6:
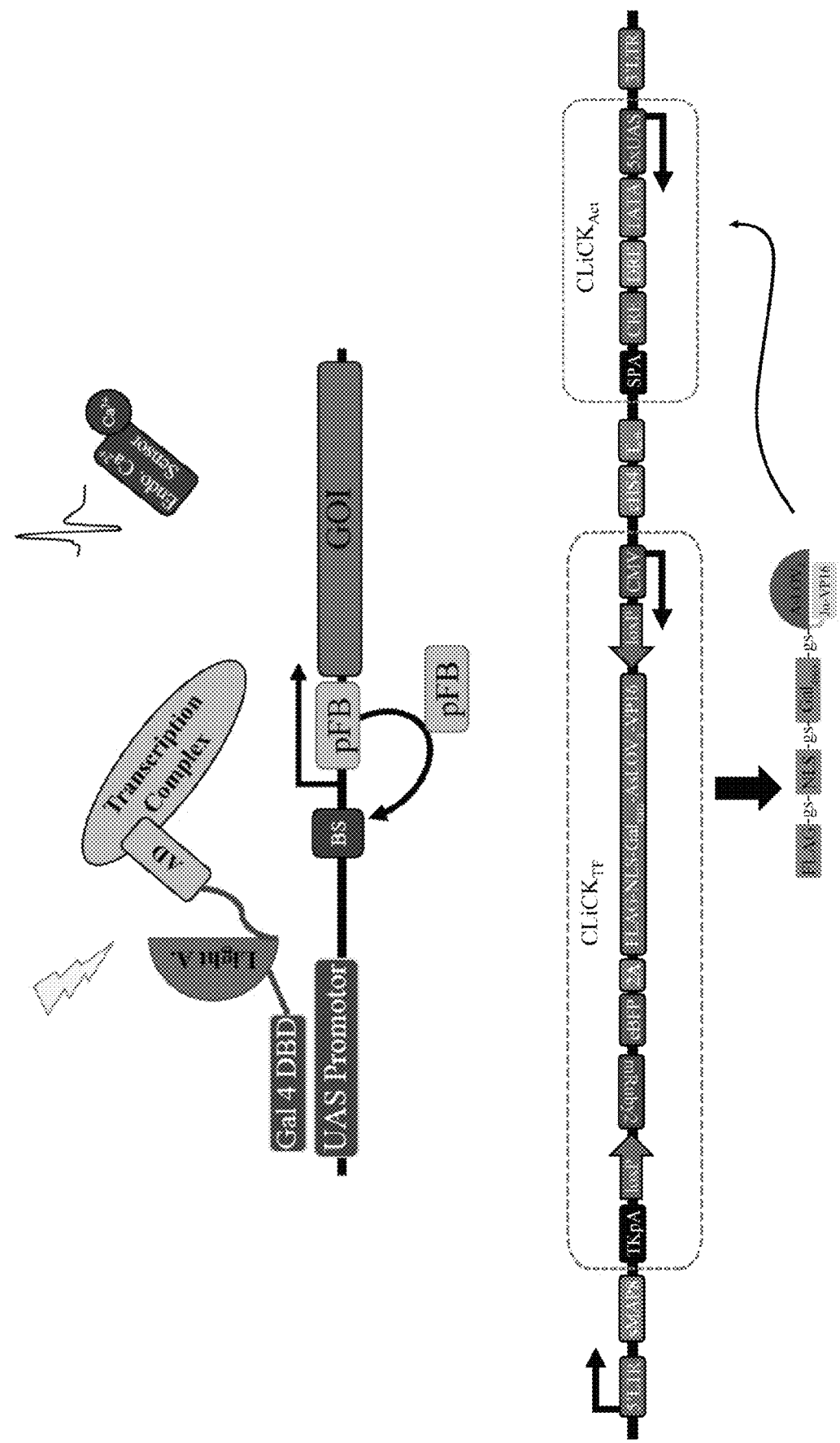
FIG. 6, top, shows an embodiment that includes a positive feedback component (pFB) that amplifies signal.

Provided herein are opto-genetic systems, cells, and methods thereof for modulating and regulating genetic expression in transiently active cells, such as neurons. The long-term implications of the technologies presented here are the development of a transformative genetic regulatory tool for in vivo applications, which broadly spans behavioral, cognitive, and systems neuroscience, among other disciplines. As used herein, "CLiCK" or "Ca2+ Light Coincidence Knock-in/out" refers to a genetic regulatory system for regulating genetic expression in transiently active cells within behaviorally relevant windows of time (<1 sec). Bringing together techniques in genetic engineering, plant biology, and neuroscience in a novel manner, CLiCK has been designed to control the expression of a gene-of-interest (GOI), such as, Cre, fluorophores, channelrhodopsins, shRNAs, CRISPR, TALEN, etc., through the co-occurrence of cell activity and the uncaging of a light-switchable transcription factor. Only with the co-occurrence of light (exogenously or experimentally driven) and inherent cellular activity does gene transcription occur. CLiCK overcomes the current limitation of poor temporal resolution (hours long) of activity-dependent specificity in current approaches through its incorporation of gating components that operate at the millisecond timescale. CLiCK incorporates all the attributes of genetics, such as region and cell type selectivity. The technologies described herein can be extended, in some embodiments, to any region of the central and/or peripheral nervous systems where characterization of neural circuits driving complex behaviors are of interest. Development of the CLiCK opto-genetic systems described herein is useful for catalyzing new forms of research in the scientific exploration of a variety of disciplines, including studies of the brain and behavior.

The human brain is made up of billions of neurons which communicate through electrical impulses. These neurons form networks that act to coordinate the electrical impulses into neural activity patterns which modulate gene expression and drive our behaviors.

In neurological disorders, these activity patterns become abnormal and produce changes in behavior and gene expression. For example, in epilepsy, neural activity becomes hyper-coordinated, such that clusters of neurons fire electrical impulses simultaneously which leads to seizures, memory lost, and brain damage.

A critical barrier in isolating epileptogenic neurons is simply identifying them from non-epileptogenic cells. These neurons exist in a richly complex cellular matrix which are buried in specific regions of the brain. In order to overcome this barrier, the CLiCK opto-genetic systems described herein can be used to permanently mark active neurons at precise windows of time. CLiCK is a genetic platform that comprises two gating components. First is an activity sensor that works to inhibit gene expression in the absence of neural activity. The second is a light sensor that inhibits gene expression in the absence of light giving researchers the ability to control exactly when an activity neuron should be marked. As shown herein, using neural cultures, neurons containing CLiCK opto-genetic systems' genetic code do not express the marker by activity or light alone. The neuron must be active while exposed to light for the marker to be expressed.

The technologies described herein can be implemented for drug discovery purposes. For example, using a Suzsey mouse model, which is a model of temporal lobe focal point seizures, the genetic code for a CLiCK opto-genetic system is introduced into the brain via, for example, viral injection, followed by a period of incubation allowing the new genetic material to be taken up by the neurons. To pair light to epileptic neural activity, a dual implant containing a fiber optic for the passage of light and an electrode for monitoring neural activity can be used. This allows a light pulse to be triggered by epileptic events, thereby marking the neurons actively driving the event and allowing isolation from within the cellular matrix. With the neurons marked, tissue samples are collected and the phenotype tagged neurons isolated. These neurons, which contain abnormal activity-dependent gene expression, can be studied at the genomic, transcriptomic, and proteomic level, unlike previously, where the data would be too subtle to detect in larger heterogeneous tissue samples. These data can then be used, for example, in drug discovery to develop key gene assays and identify cellular phenotypes from which chemical screens and key compounds can be developed and tested as candidate therapies for preclinical trails. Accordingly, the technologies described herein can serve as a powerful new research and development platform across an array of neuropsychiatric disorders to advance understanding of these disorders and to develop new therapeutic approaches.

Accordingly, provided herein in some aspects are CLiCK systems comprising:
a. a control module comprising a nucleic acid sequence encoding a chimeric photosensitive transcription factor operably linked to a promoter, where the photosensitive transcription factor comprises: (i) a transcription activation domain; (ii) a sequence-specific DNA binding domain; and (iii) a photo-sensitive actuator domain that is activated by photoirradiation in a defined range of wavelengths; and
b. a physiologically responsive module comprising a nucleic acid sequence encoding a gene of interest operably linked to an inducible promoter comprising
  i. a sequence element that binds the sequence-specific DNA binding domain of the photosensitive transcription factor, and
  ii. a physiological response element comprising a binding site for a physiological response factor, the binding of which factor is directly regulated by a physiological agent or condition; where expression of the gene of interest in a cell comprising the system requires the presence of both the physiological agent or condition and photo irradiation within the defined range of wavelengths.

As used herein, a CLiCK system comprises two modular components, a control module and a physiologically responsive module. The "control module" encodes a chimeric photosensitive transcription factor, also referred to herein as a "CLiCK$_{TF}$," such that the chimeric photosensitive transcription factor comprises a transcription activation domain, a sequence specific binding domain that interacts with the physiologically responsive module, and a photosensitive domain that is activated by photoirradiation within a defined range of wavelengths. The "physiologically responsive module" encodes a gene of interest operably linked to a promoter comprising a sequence element that can be bound, in part, by the photosensitive transcription factor of the control module, and a physiological response element comprising a binding site for a physiological response factor. The physiologically responsive module is also referred to herein as "CLiCK$_{ACT}$."

In regard to the chimeric photosensitive transcription factor encoded by the control module, as used herein, a "transcription activation domain" refers to the domain of a transcription factor that interacts with transcriptional control elements and/or transcriptional regulatory proteins (i.e., transcription factors, RNA polymerases, etc.) to increase and/or activate transcription of one or more genes. Non-limiting examples of transcriptional activation domains include: a herpes simplex virus VP16 activation domain, VP64 (which is a tetrameric derivative of VP16), HIV TAT, a NFκB p65 activation domain, p53 activation domains 1 and 2, a CREB (cAMP response element binding protein) activation domain, an E2A activation domain, NFAT (nuclear factor of activated T-cells) activation domain, yeast GAL4, yeast GCN4, yeast HAP1, MLL, RTG3, GLN3, OAF1, PIP2, PDR1, PDR3, PHO4, LEU3 glucocorticoid receptor transcription activation domain, B-cell POU homeodomain protein Oct2, plant Ap2, or any others known to one or ordinary skill in the art. A transcriptional activation domain can comprise a wild-type or naturally occurring sequence, or it can be a modified, mutant, or derivative version of the original transcriptional activation domain that has the desired ability to increase and/or activate transcription of one or more genes.

The chimeric photosensitive transcription factor further comprises a sequence-specific DNA binding domain that binds the sequence element of the physiologically responsive modules. As used herein, a "sequence-specific DNA binding domain" refers to a protein domain portion of the chimeric photosensitive transcription factor that has the ability to selectively bind DNA having a specific, predetermined sequence. A sequence-specific DNA binding domain can comprise a wild-type or naturally occurring sequence, or it can be a modified, mutant, or derivative version of the original domain that has the desired ability to bind to a desired sequence. In some embodiments, the sequence-specific DNA binding domain is engineered to bind a desired sequence. Non-limiting examples of proteins having sequence-specific DNA binding domains that can be used in the control modules described herein include GAL4, GCN4, THY1, SYN1, NSE/RU5', AGRP, CALB2, CAMK2A, CCK, CHAT, DLX6A, EMX1, zinc finger proteins or domains thereof, CRISPR/Cas proteins, such as Cas9, Cas3, Cas4, Cas5, Cas5e (or CasD), Cash, Cas6e, Cas6f, Cas7, Cas8a1, Cas8a2, Cas8b, Cas8c, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu196, and TALES.

In those embodiments where a CRISPR/Cas-like protein is used, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the functions of the systems described herein. In some embodiments of the engineered systems, methods, and compositions thereof disclosed herein, a CRISPR enzyme that is used as a DNA binding protein or domain thereof is mutated with respect to a corresponding wild-type enzyme such that the mutated CRISPR or domain thereof lacks the ability to cleave a nucleic acid sequence containing a DNA binding domain target site. For example, in some embodiments, a D10A mutation is combined with one or more of H840A, N854A, or N863A mutations to produce a Cas9 enzyme substantially lacking all DNA cleavage activity.

The photosensitive actuator domain of a photosensitive transcription factor is a domain that allows the transcription factor to be activated upon photoirradiation within a defined range of wavelengths. In some embodiments, the defined range of wavelengths encompasses the far red spectrum in order to increase light penetration in vivo, for example, between 710 and 850 nm wavelength. In some embodiments, where an AsLOV2 photoreceptor domain is used, the defined range of wavelengths encompasses about 425-490 nm wavelength, with peak absorbance at 450 nm. Non-limiting examples of photosensitive actuator domains that can be used with the CLiCK systems described herein include a Light-Oxygen-Voltage (LOV) photoreceptor domain, an LOV2 photoreceptor domain, a Cryptochrome (CRY) photoreceptor domain, Blue-light-using FAD (BLUF) photoreceptor domain, a Phytochrome (PHY) photoreceptor domain, and a UVR8 photoreceptor domain. In some embodiments of the CLiCK systems described herein, the LOV photoreceptor domain comprises the *Avena sativa* phototropin LOV2 photoreceptor domain.

Photosensitive actuator domains as described herein provide rapid transduction of an optical stimulus to a shift in transcriptional activation activity. Factors useful in the systems, methods and compositions described herein have optical response times on the order of minutes to milliseconds. Response times include, for example, 10 minutes or less to about 1 millisecond, and ranges therebetween, e.g., about 5 minutes to about 1 minute, about 5 minutes to about 30 seconds, about 5 minutes to about 10 seconds, about 5 minutes to about 1 second, about 5 minutes to about 500 ms, about 5 minutes to about 400 ms, about 5 minutes to about 300 ms, about 5 minutes to about 200 ms, about 5 minutes to about 100 ms, about 5 minutes to about 10 ms, about 5 minutes to about 1 ms, about 1 minute to about 30 seconds, about 1 minute to about 10 seconds, about 1 minute to about 1 second, about 1 minute to about 500 ms, about 1 minute to about 400 ms, about 1 minute to about 300 ms, about 1 minute to about 200 ms, about 1 minute to about 100 ms, about 1 minute to about 10 ms, about 1 minute to about 1 ms, about 30 seconds to about 10 seconds, about 30 seconds to about 1 second, about 30 seconds to about 500 ms, about 30 seconds to about 400 ms, about 30 seconds to about 300 ms, about 30 seconds to about 200 ms, about 30 seconds to about 100 ms, about 30 seconds to about 10 ms, about 30 seconds to about 1 ms, about 10 seconds to about 1 second, about 10 seconds to about 500 ms, about 10 seconds to about 400 ms, about 10 seconds to about 300 ms, about 10 seconds to about 200 ms, about 10 seconds to about 100 ms, about 10 seconds to about 10 ms, about 10 seconds to about 1 ms, about 1 second to about 500 ms, about 1 second to about 400 ms, about 1 second to about 300 ms, about 1 second to about 200 ms, about 1 second to about 100 ms, about 1 second to about 10 ms, or about 1 second to about 1 ms.

In some embodiments of the CLiCK systems described herein, the control module and the physiologically responsive module are encoded on a single nucleic acid molecule.

In some embodiments of the CLiCK systems described herein, the physiological response element comprises a binding site for an activity-dependent or hormone-dependent physiological transcription factor. For example, the system can be adapted to use a light-gated knock-down protein. Instead of having light gating or optical dependency of a transcription factor, the system can be designed to gate binding domains such that under non-light conditions an endogenous positive regulatory element of interest is able to bind to its binding site. Upon light stimulation the binding domain of the element is blocked by the light-gated or optically dependence knock-down protein. This would be a reversible knock-down embodiment of a CLiCK system that would recover once light stimulation ended.

In some embodiments of the CLiCK systems described herein, the activity-dependent or hormone-dependent physiological transcription factor comprises a transcriptional repressor. A "transcriptional repressor," as used herein, refers to a polypeptide or domain thereof, which when bound at or near a promoter sequence, blocks formation of transcriptional preinitiation complexes and/or decreases transcription of an RNA comprising the operably-linked coding sequence. In some embodiments, the transcriptional repressor blocks recruitment of the RNA polymerase to the promoter or blocks the RNA polymerase's movement along the promoter. A transcriptional repressor domain can comprise a wild-type or naturally occurring sequence, or it can be a modified, mutant, or derivative version of the original transcriptional repressor domain that has the desired ability to decrease and/or inactivate transcription of one or more genes.

Non-limiting examples of transcriptional repressors, or functionally active domains thereof, contemplated for use in the systems and methods described herein, include tetracycline repressor or domains thereof, AMP early repressor (ICER) or functionally active domain thereof, a Kruppel-associated box A (KRAB-A) repressor or functionally active domain thereof, a YY1 glycine rich repressor or functionally active domain thereof, a Sp 1-like repressor or functionally active domain thereof, an E(spI) repressor or functionally active domain thereof, an IκB repressor or functionally active domain thereof, or MeCP2.

As used herein, a "gene of interest" under the control of the promoter of the physiologically responsive module refers to any gene that encodes an output product that can be used to mark the state of the cell upon both a photooptical stimulus and a physiological stimulus. Representative output products encoded by a gene of interest described herein include, without limitation, reporter proteins, therapeutic agents or proteins, transcriptional repressors, transcriptional activators, selection markers, enzymes, ligand proteins, RNAs, riboswitches, short-hairpin RNAs and recombinases. Sequences encoding such output products that can be used in conjunction with the systems described herein are known in the art.

In some embodiments of the aspects described herein, the output product encoded by a gene of interest is a "reporter" or "reporter molecule." As used herein, a reporter refers to a protein that can be used to measure gene expression and generally produce a measurable signal such as fluorescence, luminescence or color. The presence of a reporter in a cell or organism is readily observed. For example, fluorescent proteins (e.g., green fluorescent protein (GFP), red fluorescent protein such as mCherry) cause a cell to fluoresce when excited with light of a particular wavelength, luciferases cause a cell to catalyze a reaction that produces light, and enzymes such as β-galactosidase convert a substrate to a colored product. Reporters for use in accordance with the systems described herein include any reporter described herein or known to one of ordinary skill in the art and sequences encoding the same.

Examples of sequences and genes encoding fluorescent proteins that can be used in accordance with the invention include, without limitation, those proteins provided in U.S. Patent Application No. 2012/0003630 (see Table 59), incorporated herein by reference in its entirety.

Examples of UV fluorescent proteins useful as reporter proteins include, but are not limited to, Sirius. Examples of blue fluorescent proteins include, but are not limited to, Azurite, EBFP2, mKalamal, mTagBFP2, and tagBFP. Examples of cyan fluorescent proteins include, but are not limited to, ECFP, Cerulean, mCerulean3, SCFP3A, CyPet, mTurquoise, mTurquoise2, TagCFP, Mtfp1, monomeric Midoriishi-Cyan, and Aquamarine. Examples of green fluorescent proteins include, but are not limited to, TurboGFP, TagGFP2, mUKG, Superfolder GFP, Emerald, EGFP, Monomeric Azami Green, mWasabi, Clover, and mNeon-Green. Examples of yellow fluorescent proteins include, but are not limited to, TagYFP, EYFP, Topaz, Venus, SYFP2, Citrine, Ypet, IanRFP-ΔS83, and mPapaya1. Examples of orange fluorescent proteins include, but are not limited to, Monomeric Kusabira-Orange, mOrange, mOrange2, mKOK, and Mko2. Examples of red fluorescent proteins include, but are not limited to, TagRFP, TagRFP-T, mRuby, mRuby2, mTangerine, mApple, mStrawberry, FusionRed, mCherry, and mNectarine. Examples of far red fluorescent proteins include, but are not limited to, mKate2, HcRed-Tandem, mPlum, mRaspberry, mNeptune, NirFP, TagRFP657, TagRFP675, and mCardinal. Examples of near IR fluorescent proteins include, but are not limited to, iFP1.4, iRFP713 (iRFP), iRFP670, iRFP682, iRFP702, iRFP720, and iFP2.0. Examples of sapphire-type fluorescent proteins include, but are not limited to, Sapphire, T-Sapphire, and mAmetrine. Examples of long Stokes shift fluorescent proteins include, but are not limited to, mKeima Red, mBeRFP, LSS-mKate2, LSS-mKate1, and LSSmOrange.

Luciferases can also be used as reporter molecules, as cells tend to have little to no background luminescence in the absence of a luciferase. Luminescence can be readily quantified using a plate reader or luminescence counter. Examples of genes encoding luciferases that can be used in the systems described herein include, without limitation, dmMyD88-linker-Rluc, dmMyD88-linker-Rluc-linker-PEST191, *Renilla* luciferase, and firefly luciferase (from *Photinus pyralis*).

Enzymes that produce colored substrates ("colorimetric enzymes") can also be used as reporter molecules. Enzymatic products can be quantified using spectrophotometers or other instruments that can take absorbance measurements including plate readers. Like luciferases, enzymes such as β-galactosidase can be used for measuring low levels of gene expression because they tend to amplify low signals. Examples of genes encoding colorimetric enzymes that can be used in accordance with the systems described herein include, without limitation, lacZ alpha fragment, lacZ (encoding β-galactosidase, full-length), and xylE.

The promoter operably linked to a gene of interest in the physiologically responsive module comprises a sequence element that can be bound, in part, by the sequence-specific DNA binding domain of the photosensitive transcription factor of the control module. As used herein, a "sequence element" refers to a target sequence to which the sequence-specific DNA binding domain of the photosensitive transcription factor selectively binds. For example, where the sequence-specific DNA binding domain comprises three zinc-finger domains, for example, the sequence element comprises at least a 9 base pair region. In other embodiments, where the sequence-specific DNA binding domain comprises a Cas protein or DNA binding domain thereof, the sequence element is a CRISPR (Clustered Regularly Interspaced Short Palindromic Repeats) DNA sequence that can be bound by a Cas protein or DNA binding domain.

The promoter operably linked to a gene of interest in the physiologically responsive module also comprises a physiological response element comprising a binding site for a physiological response factor. Such a physiological response element refers to a sequence that is responsive to one or more physiological conditions, such as changes in pH, temperature, radiation, osmotic pressure, saline gradients, cell surface binding, and the concentration of one or more extrinsic or intrinsic inducing agents. The extrinsic inducer or inducing agent can comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. One non-limiting example of such a physiological response element is a DRE/DREAM regulatory element.

As used herein, the term "activity dependent" or "activation specific" refers to the property of a response or marker of cellular activity or activation. As but one example, when activity of a cell, e.g., firing of a neuron, contraction of a muscle cell, or activation of an immune cell, results in or from a change, e.g., in an ion concentration or metabolite, as non-limiting examples, that change is "activity dependent." Similarly, the binding of a transcription factor or repressor that responds to such a change is also "activity dependent" as the term is used herein.

Figure 7A:
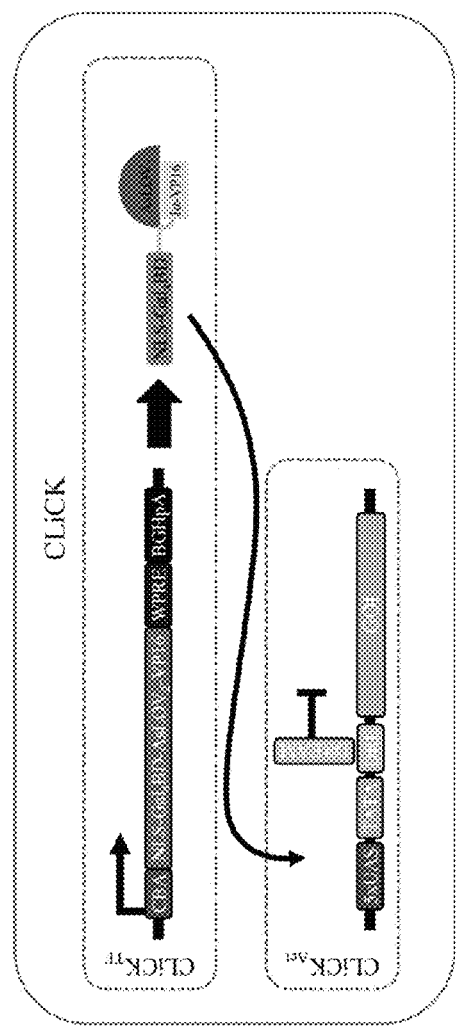
FIGS. 7A-7C depict an overview of an embodiment of a CLiCK. System. 7A. CLiCK comprises two functional components, a light-switchable transcription factor (CLiCK$_{TF}$) which is used to experimentally define periods of time for which expression of an GOI in CLiCK$_{Act}$ can be driven by neural activity. Upon exposure to blue light, the activation domain (Jα-VP16) of the CLiCK$_{TF}$ abducts from the β-sheet of AsLOV$_2$ allowing it to form transcription complexes (FIG. 7Bc-7Bd). In dark, the activation domain is caged preventing formation of transcriptional complexes (FIG. 7Ba, FIG. 7b). Activity-induced nuclear Ca2+ transients act to dissociate the repressive element DREAM from its binding domain, DRE (FIG. 7Bb and FIG. 7Bd). During nonactive periods DREAM represses gene expression (FIG. 7Ba and FIG. 7Bc). Simultaneous derepression of DREAM and photostimulation drives gene expression (FIG. 7Bd).
Figure 7B:
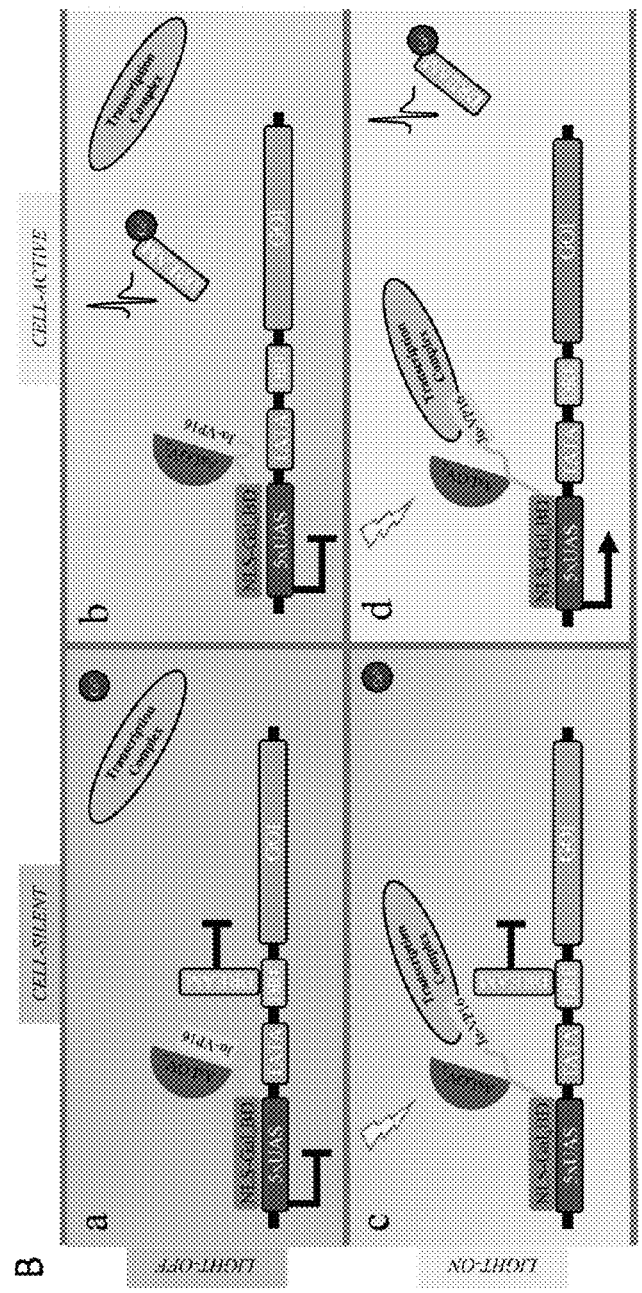

FIG. 7A provides an exemplary CLiCK system comprising the two modular components: a light-switchable transcription factor, termed herein as "CLiCK$_{TF}$," and a downtarget activity-dependent vector, CLiCK$_{Act}$. The gene encoding CLiCK$_{TF}$ gene is placed under a constitutive promoter (e.g., CAG, Syp1, CMV), creating a readily available supply of a light-switchable transcription factor. The promoter can also be cell specific, in some embodiments. The CLiCK$_{TF}$ protein comprises a DNA binding domain, such as a Gal4 binding domain that is used to target to a downstream promoter of the CLiCK$_{Act}$ module, such as a downstream 5×UAS promoter. Within the promoter region of CLiCK$_{Act}$ there is an activity-dependent repression element which acts to repress expression of a gene-of-interest (GOI). As shown in FIG. 7B, there are four states of CLiCK. As shown in panels a-c in FIG. 7B, gene expression does not take place outside of simultaneous engagement of both gating mechanisms. For example, FIG. 7Bc illustrates the state of CLiCK when only the light-switchable component, CLiCK$_{TF}$, is engaged. In this state the transcriptional activation domain, such as VP16, is relieved from its allosteric block exposing it to allow formation of transcriptional complexes. However, gene expression remains repressed through the activity-dependent regulatory element, such as a DRE/DREAM regulatory element. For gene expression to occur both CLiCK$_{TF}$ and CLiCK$_{Act}$ must be engaged (FIG. 7Bd).

Figures 9A, 9B, 9C, 9D, 9E, 9F:
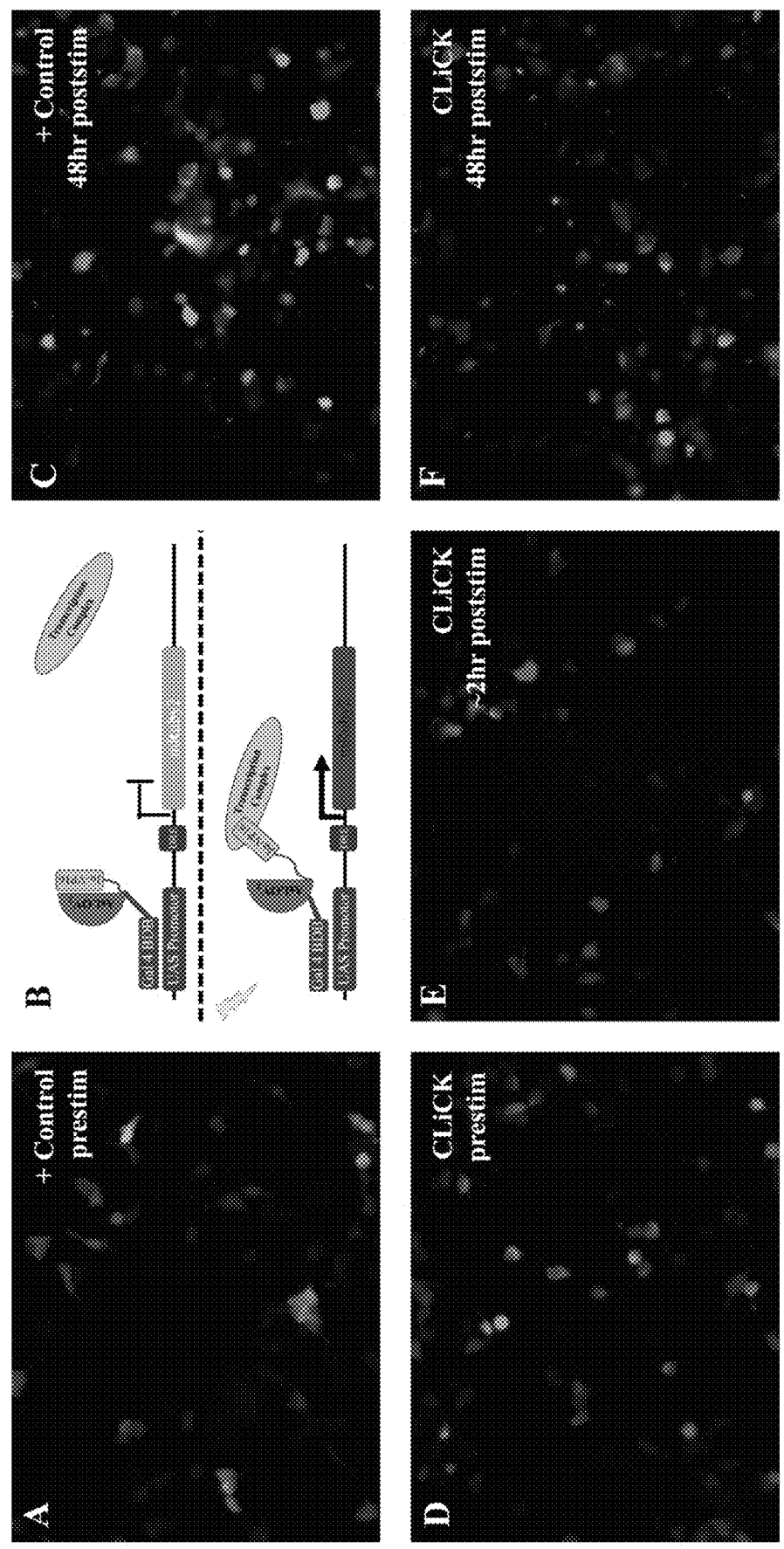
FIGS. 9A-9F show in vitro assay of CLiCK$_{TF}$. HEK cells co-transfected with a two-plasmid version of CLiCK driving mRuby2 expression (red) and an eGFP transfection marker (green). HEK cells do not endogenously express the DREAM protein, therefore, the presence of the DREAM binding sequence, DRE, does not repress mRuby2 expression (9B). mRuby2 expression, prestimulus (9A) and 48 hr poststimulus (9C), in positive control consisting of a light-independent transactivator (Gal4 binding domain directly linked to VP16 activation domain) and the downstream target CLiCK$_{Act}$. In the absence of DREAM, mRuby2 can be expressed using a light-independent transactivator (9A and 9C). (9D) Expression of mRuby2 is not observed prior to light stimulus. (9E) mRuby2 expression is observed 2 hrs following 2×1 second exposures (3 second interval) to blue light (450 nM peak, 14 mW). (9F) 48 hours poststimulus indicating mRuby2 expression is reversible.

In some designs, a two plasmid system was used to deliver each vector. However, random variations in transfection efficiencies and copy numbers are in contrast to the co-dependency of these two vectors. Accordingly, in preferred embodiments of the aspects described herein, a dual-independent promoter design is used (FIG. 9C). Accordingly, as shown herein, through the unique design of each component and their co-dependency in driving gene expression, CLiCK is a powerful new tool for experimentally isolating precise windows of time in which genetic manipulations can be exclusively triggered in populations of active neurons in awake and behaving animals.

As shown herein, examining the properties of activity-induced Ca2+ transients in the neuron provides a compelling argument for its use as a marker of neural activity. Voltage-sensitive gating of plasma membrane Ca2+ channels provides the mechanistic basis for a direct coupling between depolarization and triggering of action potentials with a rise in cytosolic Ca2+ that propagates into the nucleus. Ca2+ freely enters and exits the nucleus through nuclear pore complexes distributed along the nuclear envelope, making the nuclear envelope a non-measurable diffusion barrier to Ca2+. Given that cytosolic Ca2+ levels cannot be controlled through its synthesis or destruction and its role across the brain in regulating large sets of genes of virtually every aspect of cellular function, such as synaptic transmission, structural plasticity, energy metabolism, and survival, activity-induced nuclear Ca2+ transients are likely highly controlled and conserved across the brain, providing an invariable reporter of neuronal activity across cell types. To allow for the diversity of meaningful functional roles of Ca2+ in cells, its concentration and spread in response to stimuli is tightly regulated, such that nuclear Ca2+ transients offer a low noise indicator of neural activity. For example, sarcoendoplasmic reticulum Ca2+ ATPase (SERCA) pumps localized in the endoplasmic reticulum shield the nucleus from ambiguous Ca2+ invasions by facilitating Ca2+ cytosolic clearance. Forgoing the need for any intermediate enzymatic reaction, activity-induced Ca2+ transients bridge distances of 100s of microns with milliseconds to their transduction site, the nucleus.

Ideally, for use with the systems and methods described herein, the transducer of activity-driven Ca2+ transients interacts directly with Ca2+ in the nucleus, thereby avoiding any temporal and causal effects of intermediate molecules or reactions. One known mechanism for direct Ca2+-induced gene expression uses the transcriptional repressor DREAM. As used herein, "DREAM" or "downstream responsive element antagonist modulator" refers to a multi-functional EF-hand protein of the KChIP (potassium channel interacting protein) subfamily (KChIP1-4). Endogenously expressed throughout the brain, DREAM is involved in an array of Ca2+-dependent responses and can be found in the plasma membrane, cytosol, and nucleus of a cell. In the nucleus, DREAM acts as a transcriptional repressor for several genes, e.g., immediate-early gene c-fos, prodynorphin, NCX3 (Na+/Ca2+ exchanger), and CREB-mediated genes. DREAM represses gene expression by binding as homo- or hetero-tetramers of EF-hands to specific DRE sites upstream of gene translation start sites. Derepression of DREAM occurs by direct Ca2+ binding at micromolar concentrations, causing dissociation of DREAM from its DRE binding site. Mutation of any of the Ca2+ binding EF-hand motifs causes DREAM to become insensitive to Ca2+ leading to loss of gene expression, indicating DREAM binding is driven by direct intranuclear Ca2+.

Incorporating DRE/DREAM or a Ca2+-responsive functional fragment thereof into the promoter region of the gene can be ideally suited for regulating expression in an activity-dependent manner. Genome-wide analysis has shown DRE sequences contain a conserved core sequence GTCA. Though the conserved core is orientation-independent, it is ubiquitously found+40 bp downstream of the TATA box and can appear multiple times throughout this region. The binding affinity of DREAM to individual DRE sequences varies. For example, relative to the human dynophrine (hDynDRE) DRE sequence, DREAM bins with a 166% affinity to the ICERDRE sequence and 157% to the DRE sequence found in the c-fos promoter. As it is not known how the affinity of these sequences change when incorporated into novel promoter regions, a range of DRE sequences and their consensus sequence, PuNGTCAPuPuG (SEQ ID NO: 1) can be tested, as understood by one of ordinary skill in the art.

Engineered versions of $CLiCK_{Act}$ can be cloned into dual-independent promoter backbones using standard cloning techniques. Previously untested DRE sequences can be custom designed with unique restriction sites, in some embodiments, and buffer bases flanking the 5' and 3' ends to allow for simple digestion and ligation into backbones can also be used, in some embodiments. DRE sequences, typically comprising 18 bp, can be ordered from oligonucleotide service providers, such as IDT. For non-neuronal cells or cells that do not naturally express DREAM, the factor can be delivered by expression from an appropriate expression cassette (on the same or different vector as the other CLiCK components), or expression vector. In this manner, expression of a reporter or effector gene can be placed under Ca2+ control in other cell types.

Clones can be digested with specific restriction enzymes and screened for correct sizes using, for example, southern blots. Sequencing of clones can be used to verify absence of mutations or erroneous sequences.

To allow for precise temporal control over periods of activity-dependent gene expression a light-driven actuator is purposed. The blue-light sensitive LOV (light, oxygen, voltage) photoreceptors are becoming widely used in optogenetic and biotechnology applications, providing high spatial resolution and temporal precision. LOV undergoes photoinducible (450 nm) structural changes by the formation of a covalent adduct between flavin mononucleotide (FMN), abundant in all eukaryotic cells, and a conserved cysteine residue within the LOV photosensor. LOV light response kinetics have been shown to be tunable through mutations along certain AAs making them malleable to specific applications. The LOV2 domain from *Avena sativa* ($AsLOV_2$) phototropin 1 has the fastest known photocycle kinetics of the LOV phototropins. A LOV transcription factor system was designed by linking the nuclear protein GI (*Gigantea*) to Gal4 and LOV to the activation domain VP16. Upon illumination, LOV forms a covalent bond with the nuclear protein GI that is sitting at a 5×UASG binding domain upstream of the TATA box, thereby bringing VP16 into the transcription start site and inducing expression of the gene. Embodiments of this can use customizable zinc fingers to target diverse DNA sequences. A rate limiting step in this design stems from the need of the LOV-VP16 to translocate to the binding domain factor, Gal4-GI, requiring several minutes of light stimulation.

The temporal resolution of a LOV-based transcription factor can be greatly increased by simply starting with the transcription factor already at the transcription start site, thereby foregoing the time needed for translocation of the TF following photostimulation. Using NMR, conformational dynamics in the phototropin domain $AsLOV_2$ has been observed to occur at the µm-ms timescale.

Novel designs described herein directly link $AsLOV_2$ to a Gal4 binding domain, and fusing the activation domain VP16 into the J-helix of $AsLOV_2$ preserves the temporal sensitivity of AsLOV2 by limiting the number and complexity of functional interactions required between photostimulation and formation of transcriptional complexes (FIG. 7A-7B). By linking $AsLOV_2$ directly to a binding domain the time needed to translocate to its target gene after photostimulation is forgone. The choice of VP16 was due to the combination of its short yet strong activation region. VP16 has a minimal activation motif DALDDFDLDML (SEQ ID NO: 2) with a critical AA F442. This small motif and presence of a critical AA lends well to the allosteric gating of AsLOV2's J-helix segment. When fused into the J-helix of AsLOV2 the critical AA of VP16, promoting formation of transcriptional complexes, is sterically blocked under dark conditions. Upon photostimulation, the critical AA is exposed and transcriptional complexes are able to form.

It is contemplated herein that other actuator domains could be adapted to provide faster activation kinetics, albeit in response to a different stimulus. For example, the activation domain of phosphodiesterase 4,5, e.g., *Homo sapiens*, has activation kinetics in response to cAMP/cGMP on the order of 100s to 10s of milliseconds.

Figure 7C:
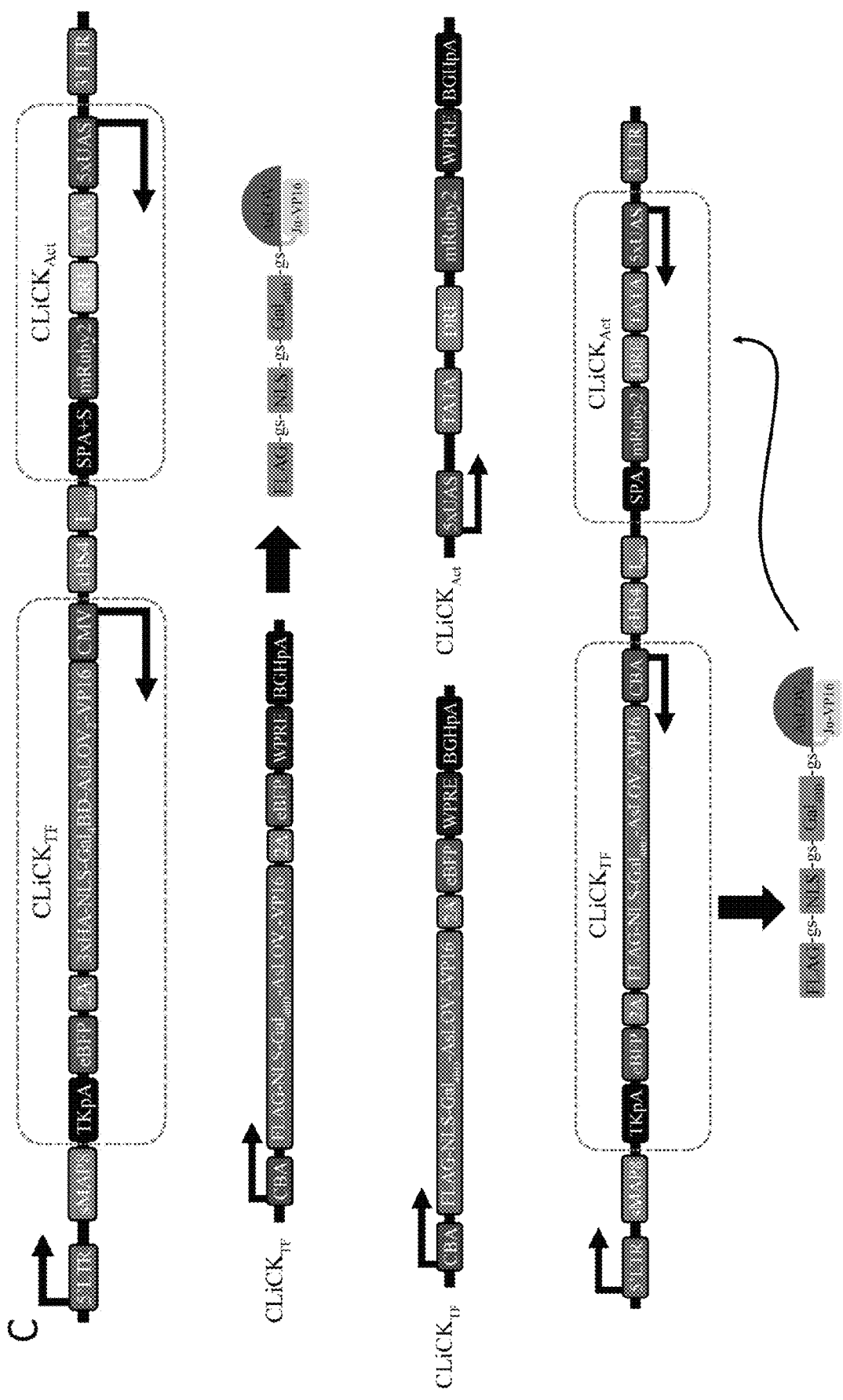

Initial designs of $CLiCK_{TF}$ placed its expression vector in a separate plasmid from $CLiCK_{Act}$. As it is crucial that both expression vectors are present in the cell for CLiCK to be functional, a two plasmid design is less then ideal, and a single dual-independent promoter design containing both expression cassettes is preferred, therein eliminating chances of failure through incomplete transfection/transduction of CLiCK or variations in copy numbers (FIG. 7C).

Previously engineered versions of $CLiCK_{TF}$ can be cloned into dual-independent promoter backbones using standard cloning techniques. Clones can be examined for correct size using, for example, single cut restriction enzymes and screened on southern blots. Clones of correct size are sequenced for correct alignment of fusion sequences and screened for mutations.

In some embodiments, for in vitro assays, the gene encoding the fluorophore mRuby2 can be used as the functional reporter GOI. Transfections can be confirmed using an eBFP transfection marker (FIG. 7C). Functional assays can be carried out, for example, in dissociated HEK and E18 mouse primary cortical neuron culture as summarized in FIG. 8

Due to the absence of DREAM in HEK cells, derepression of DREAM by Ca2+ is not required for gene expression. Therefore, gating of gene expression by light can be independently tested in HEK cells without the need to block or knock-out endogenous DREAM. Dissociated HEK cells can be transfected at 60% confluency using magnetic transfection (NEUROMAG). Following transfection, cells can be kept in light-tight containers and incubated at 37° C. for two days.

After incubation, cells can be assayed in light-controlled environments. Activity-dependency and co-dependency of light and neural activity can be evaluated in E18 rat primary cortical culture. Rat primary cortical neurons can be plated at $0.5 \times 10^5$ density in 500 L plating media. 50% media changes can be performed every 3 days with fresh feeder media. Conditioned media drawn off during media changes can be kept at −20° C. so that it can be later used for media exchanges during assaying. At 10 DIV, cells can be transfected with appropriate CLiCK plasmids using magnetic transfection (NEUROMAG). Transfected cells can be kept in light-tight containers and incubated at 37° C. for two days to allow for expression of $CLiCK_{TF}$. Following incubation, cells can be assayed under light-controlled environments.

Three general assays can be used to evaluate CLiCK: light-, activity-, and co-dependent assays. Light-dependent assays can use blue light (450 nm, 12 mW) at 1, 5, and 10 second exposures to characterize the light responsiveness of $CLiCK_{TF}$ over different lengths of photostimulation in dissociated HEK cells. In Activity-dependent assays 60 mM of KCl can be briefly applied to culture media, then replaced with fresh conditioned media containing 1 μM TTX to create brief periods of induced spiking in E18 rat dissociated primary cortical neuron cultures. Media exchange can be performed manually by pipette or automated with a media exchanger. To suppress spontaneous spiking in negative controls 1 μM of TTX can be added to culture media 1.5 hrs prior to assaying. Co-dependent assays can comprise simultaneous application of light- and activity-dependent assays in E18 rat dissociated primary cortical neuron cultures. Assays evaluating the light-activatable transcription factor, $CLiCK_{TF}$, can be carried out in light-controlled environments to avoid unintended uncaging of $CLiCK_{TF}$. Following stimulation by light or KCl, cells can be incubated at 37° C. (in light-tight containers where appropriate) for a period of 4-24 hrs to allow for gene expression. Following incubation, expression of the gene of interest, such as Ruby2 can be imaged under fluorescent microscopy at 2 hr intervals over a period of 8 hrs and once again at 48 hrs to evaluate the time course and reversibility of mRuby2 expression.

Figure 8:
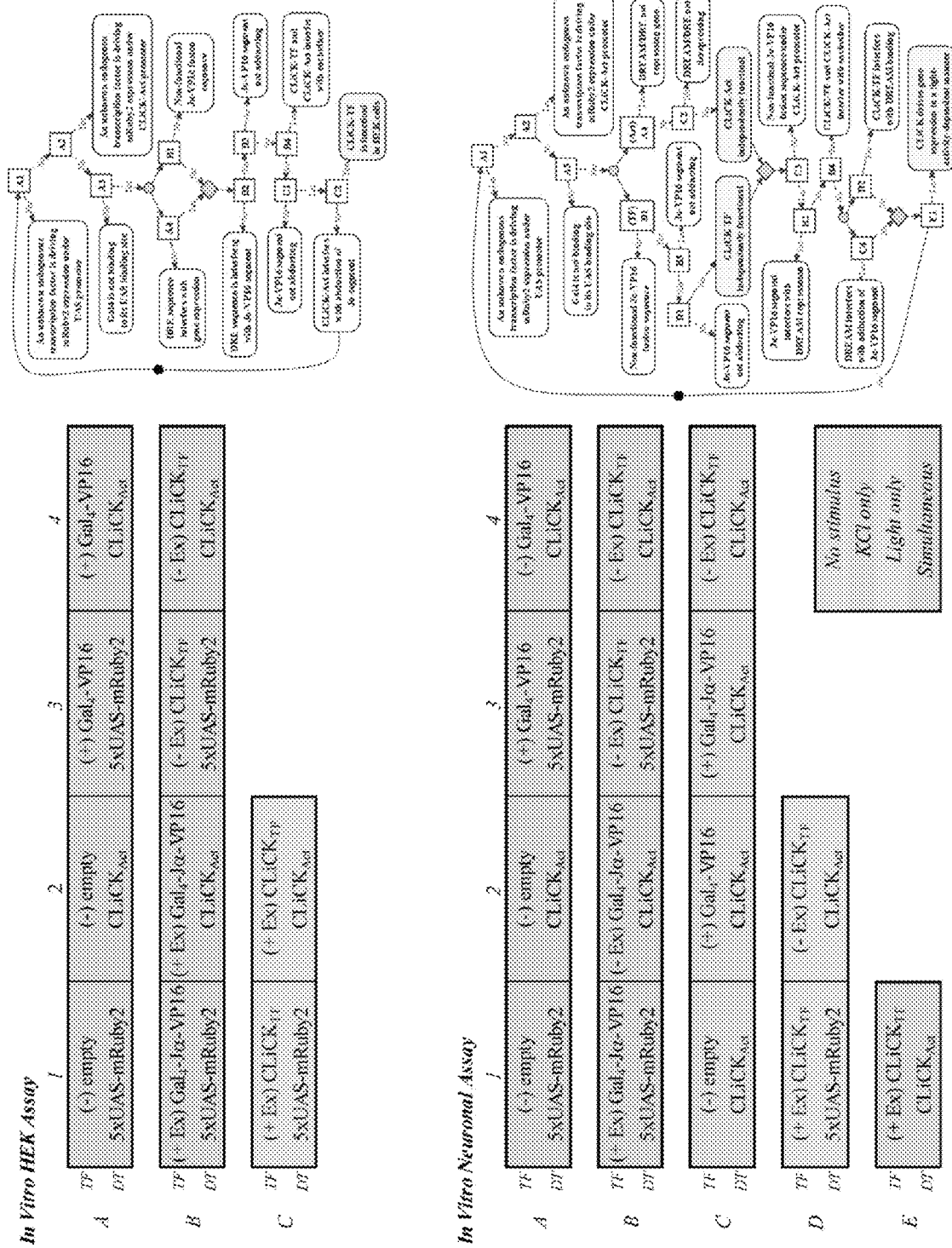
FIG. 8 depicts in vitro assay design. (Top) Dissociated HEK cells are used to verify the ability to drive gene expression by photostimulation. (Bottom) Dissociated E18 mouse primary cortical neuron cultures are used to test co-dependency of light and KCl-induced spiking to drive gene expression. Each condition indicates the transcription factor (TF) and downstream target (DT) used while background color indicates stimulus used. Negative (–) and positive (+) controls are designed to complement the negative/positive experimental conditions (–/+Ex) providing an assay design for easy identification of point of failure as determined by each assays flowchart (right). For example, if CLiCK was faulty such that the Jα-VP16 segment of CLiCK$_{TF}$ is preventing DREAM from repressing expression this would be captured at node B2 in the neuron flowchart (bottom-right).

To determine if there is unanticipated expression of the mRuby2 independent of $CLiCK_{TF}$ (identifiable in FIG. 8 at nodes HEK(A1,A2)/Neu.(A1, B2), cells can be transfected with CLiCK vectors containing only the downstream target (5×UAS-mRbuy2 or CLiCKAct), rendering expression of mRuby2 non-functional. Experiments can be carried out in both HEK and cultured primary neurons. Negative results would indicate expression of mRuby2 is not endogenously driven. Positive results would indicate the existence of an unknown endogenous transcriptional process that is able to drive expression of the GOI, thereby shortcutting the intended function of $CLiCK_{TF}$.

To determine whether $CLiCK_{TF}$ is light-gated, three points are addressed in the evaluation of the light-gating properties of $CLiCK_{TF}$: (i) does light-induced gene expression occur (identifiable in FIG. 8 at nodes HEK(C2)/Neu. (D1)), (ii) does $CLiCK_{TF}$ leak in the absence of light (identifiable in FIG. 8 at nodes HEK(B3,B4)/Neu.(B3,B4, C4)), and (iii) is $CLiCK_{TF}$ reversible (identifiable in FIG. 8 at nodes 48 hr reversal at HEK(C2)/Neu.(D1).

To isolate evaluation of $CLiCK_{TF}$ from possible failures through $CLiCK_{Act}$ light-dependent assays can be carried out in HEK cells, which lack the DREAM protein by which $CLiCK_{Act}$ represses gene expression. Initially evaluating $CLiCK_{TF}$ in HEK cells shortens the time and expense needed to identify and address failure points. Functional $CLiCK_{TF}$, can be verified in primary culture neurons for possible differences between cell types. Following light-dependent assays, cells can be monitored for over a period of 48 hours which allows evaluation of both light-inducible transcription and reversible expression. Taken together, these results exclusively test the light-gating properties of CLiCK and allow identification along any specific possible points of failure for later trouble shooting. Based on this, expression of mRuby2 is light-dependent. Post-stimulation, mRNA is no longer transcribed and mRuby2 is broken-down through intracellular mechanisms within a period of 48 hrs, in those embodiments where the CLiCK system is reversible.

To determine whether $CLiCK_{Act}$ is activity-gated (Identifiable in FIG. 8 at nodes Neu.(A4,C2) in FIG. 8), the photo-gating mechanism of $CLiCK_{TF}$ is removed, leaving a constitutive version of $CLiCK_{TF}$ that only has a binding domain and an activation domain (confirmed by positive controls), to isolate evaluation of $CLiCK_{Act}$ from possible failures in $CLiCK_{TF}$. Activity-dependent assays can be carried out in E18 rat primary cortical neuron culture. Taken together, the activity-dependent expression of $CLiCK_{Act}$ and identification of possible points of failure can be evaluated. Based on this, mRuby2 expression is driven by KCl-induced spiking in an activity-dependent manner.

Co-dependency of CLiCK on light and neural activity can be evaluated by simultaneous application of light- and activity-dependent assays in rat E18 primary cortical cultures. Functional gating of mRuby2 expression by coincident-detection can be assessed together with complementary experimental and negative controls. mRuby2 expression following simultaneous light and KCl stimuli would indicate co-dependency of gene expression in CLiCK. These experiments can be used to provide a matrix of results designed to evaluate the co-dependency of CLiCK and allow for direct identification of possible points of failure both at the level of its individual gating components, $CLiCK_{Act}$ and $CLiCK_{TF}$, and their interactions. This approach greatly facilitates trouble shooting and therein mitigates the time needed to develop a fully functional version of CLiCK. In functional versions of CLiCK, mRuby2 expression should only be observed under simultaneous conditions of photostimulation and induced spiking.

While DREAM is endogenously expressed in neurons, HEK cells do not endogenously express DREAM. Using HEK cells allows evaluation of the light-gating component, $CLiCK_{TF}$, in completed versions of CLiCK but in an activity-independent manner. This approach prevents losing time developing versions of $CLiCK_{TF}$'s that may themselves be functional, but are non-functional with the promoter design of $CLiCK_{Act}$. Running activity-dependent assays in dissociated primary neuron culture is advantageous over alternatives like slice as multiple experiments can be run relatively quickly and simultaneously over multi-well plates. Stimulus that reliably produces spiking in neuron culture is essential for evaluating activity-dependency of CLiCK. Previous studies of DRE/DREAM dynamics have shown bath application of KCl at 60 mM strongly induces spiking in cultured neurons. The temporal resolution at which $CLiCK_{TF}$ can be controlled ultimately defines the breadth of its application. Therefore, characterizing it at multiple exposure lengths is essential to understanding its full potential. In order to prevent unintended uncaging of $CLiCK_{TF}$ during imaging mRuby2, which excites outside the AsLOV2 spectrum, is used. While the adduction of the Jα-helix of AsLOV2 in $CLiCK_{TF}$ occurs at 425-490 nm, mRuby2 excites at 560 nm, allowing for fluorescent imaging while avoiding photostimulation of $CLiCK_{TF}$ over the course of imaging.

Cell counts of mRuby2 and eBFP can be used to analyze the outcomes of the functional assays. ANOVA can be used to test for differences in mRuby2 expression between conditions while accounting for variances in transfection rate (eBFP transfection marker counts). Derepression of DREAM may occur spontaneously outside of activity induced Ca2+-transients leading to leaky expression of the GOI. One possible approach to address expression leaks via spontaneous dissociation of DREAM is to incorporate additional DRE binding sites into the promoter region of $CLiCK_{Act}$. Since DREAM/DRE repression is modular, adding multiple DREAM/DRE units, in some embodiments, would greatly decrease the probability of expression leaks from spontaneous derepression. It is possible that fusion of activation domain of VP16 into the J-helix of AsLOV2 is suboptimal and leads to leaky expression in the absence of light. Since it is an allosteric mechanism and its structure has been characterized using crystallography, adduction can be modeled. Using protein folding software like ROSETTA can aid in identifying viable versions of fusion proteins with stable light-dark-properties.

Additionally, alternative transcriptional activation domains can be identified using BLAST algorithms (blastp, Psi-, Phi-, Delta-BLAST) developed by the National Center for Biotechnology Information. This can lead to identification of activation domains which tightly confer with the packing of AsLOV2's Jα-helix.

As shown herein, an embodiment of a CLiCK system was tested in HEK cells (FIGS. 9A-9F). Since HEK cells do not endogenously express the repression element DREAM, only the light-dependent component, $CLiCK_{TF}$, is validated in this assay (FIG. 9B). Dissociated HEK cells were triple transfected with the two plasmid CLiCK system (FIG. 7A) driving mRuby2 and a separate eGFP transfection marker plasmid (green). Following transfection, cells can be kept in light-tight containers and incubated at 37° C. for two days. After incubation, cells can be assayed in light-controlled environments.

Positive controls containing a constitutive light-independent version of CLiCK (FIGS. 9A and 9C) were used to confirm mRuby2 (red) can be expressed under the unique design of the $CLiCK_{Act}$ promoter. HEK cells transfected with CLiCK showed no expression of mRuby2 prior to exposure to blue light (FIG. 9D). Following brief exposure to blue light, mRuby2 is seen to be present in a subset of cells (FIG. 9E) proportional to positive controls (FIG. A). 48 hours after exposure mRuby2 appears to have been degraded and is no longer observed in the cells (FIG. 9F) indicating that expression of mRuby2 is reversible under CLiCK. These results indicate the ability to carve out windows of time as small as a second for regulated gene expression. Interestingly, only a subset of eGFP expressing cells appear to co-express mRuby2 both in positive controls and following photostimulation. Without wishing to be limited by theory, this is likely due to two reasons. (1) Consistent with what is observed in the controls (FIGS. 9A and 9C), only a certain amount of the transfection complexes may have contained all three plasmids. Since mRuby2 expression is dependent on the transfection of two individual plasmids, the probability of transfection and expression of eGFP under a single plasmid is greater than that of mRuby2. This is seen in the higher number of cells expressing eGFP than mRuby in controls and experimental conditions. Additionally, the copy number of each vector will vary within cells resulting in differential expression in cells that were successfully triple transfected. However, in this design, the ratio of mRuby2 to eGFP expressing cells appear similar between experimental and positive controls suggesting transfection optimization is needed for CLiCK to become more robust. This is addressed, as described herein, by moving from a two plasmid approach of CLiCK into a single plasmid of dual-independent promoters driving $CLiCK_{TF}$ and $CLiCK_{Act}$. (2) In addition to a lower co-transfection probability of CLiCK, the amount of mRNA transcribed following such brief exposures to light may be too little to build up enough expression of mRuby2 to be readily visible. Adding an epitope tag to the protein could help, in some embodiments, to isolate and detect it. Additionally, the frequency of photostimulation can be increased to create more mRNA while preserving the temporal precision of the stimulus.

Figures 10A, 10B, 10C, 10D:
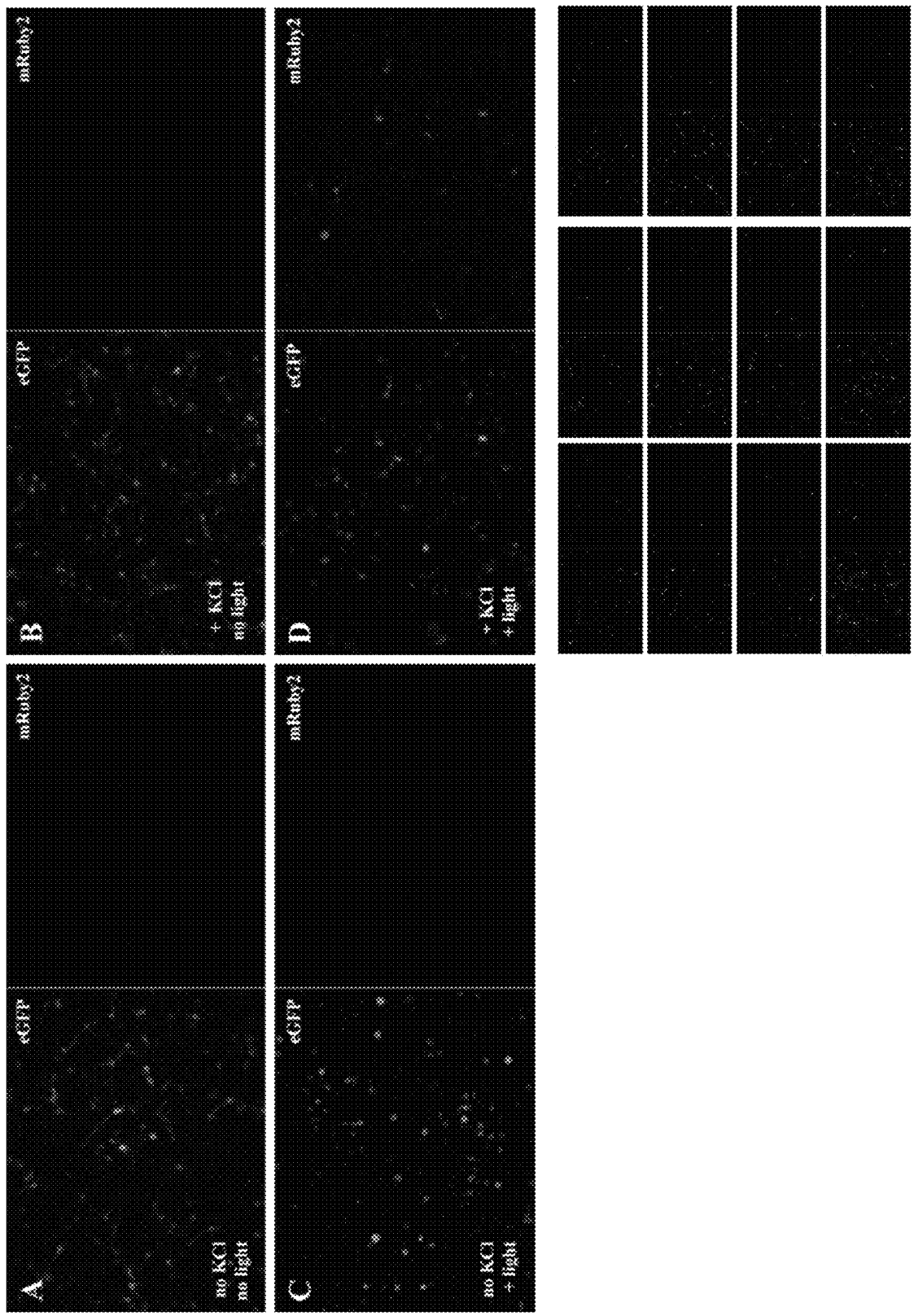
FIGS. 10A-10D show creation of temporal windows for activity-dependent gene expression at seconds resolution in rat cortical neuron culture. Expression of mRbuy2 does not occur in the absence of light and neural activity (10A, right). mRuby2 expression is not singularly driven by light (10C, right) or KCl induced spiking (10B, right) alone. Only simultaneous KCl induced spiking and exposure to blue light drives expression of mRuby2 (10D, right). Spiking was induced in neurons by brief application of 40 mM KCl (10B and 10D). A 5 second exposure to blue light (410-470 nm [442 nm peak], 14 mW) was used to uncage the transcription factor (10C and 10D). To prevent spontaneous spiking in no KCl conditions (10A and 10C) 1 μM of TTX was applied to the media 1 hour prior assaying. Neurons were triple transduced with AAV$_{2/9}$-CLiCK$_{TF}$, AAV$_{2/9}$-CLiCK$_{Act}$-mRbuy2, AAV$_{2/9}$-eGFP.
Figure 11:
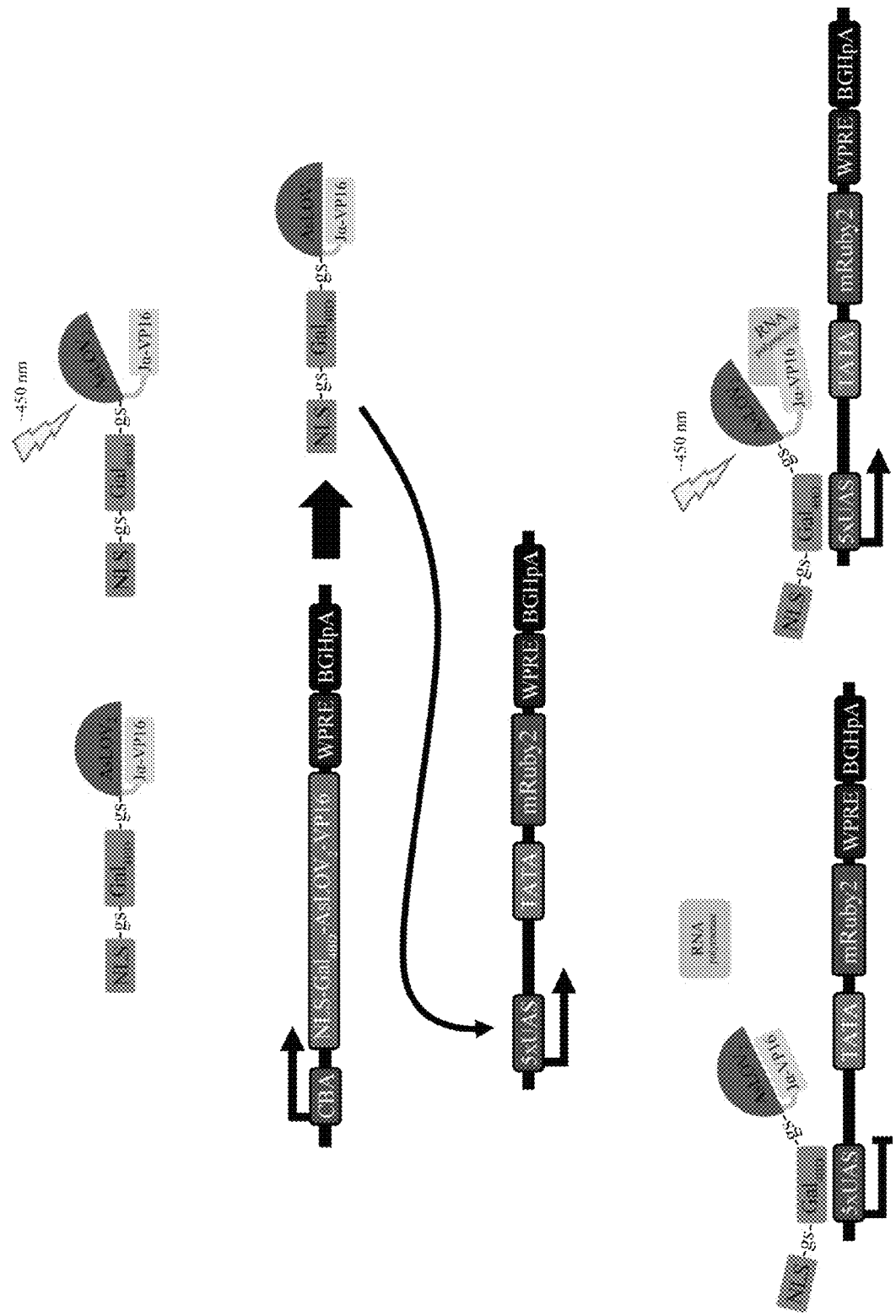
FIG. 11 depicts a schematic of an embodiment of a CLiCK optogenetic system described herein.
Figure 12:
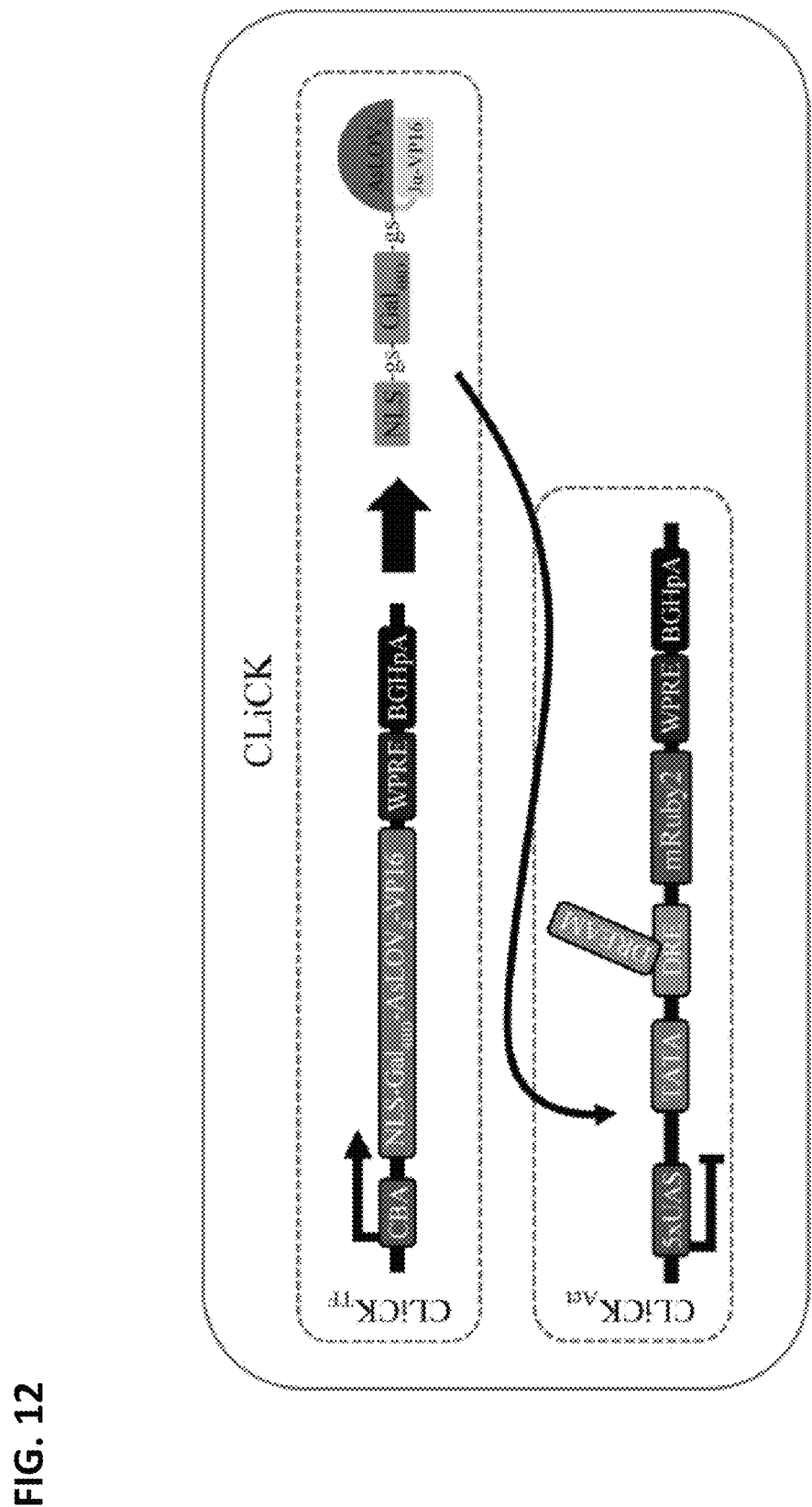
FIG. 12 depicts a schematic of an embodiment of a CLiCK optogenetic system described herein. CLiCK$_{TF}$: Light-driven transcription factor; CLiCK$_{Act}$: Downstream activity-dependent target.
Figures 13A, 13B, 13C, 13D:
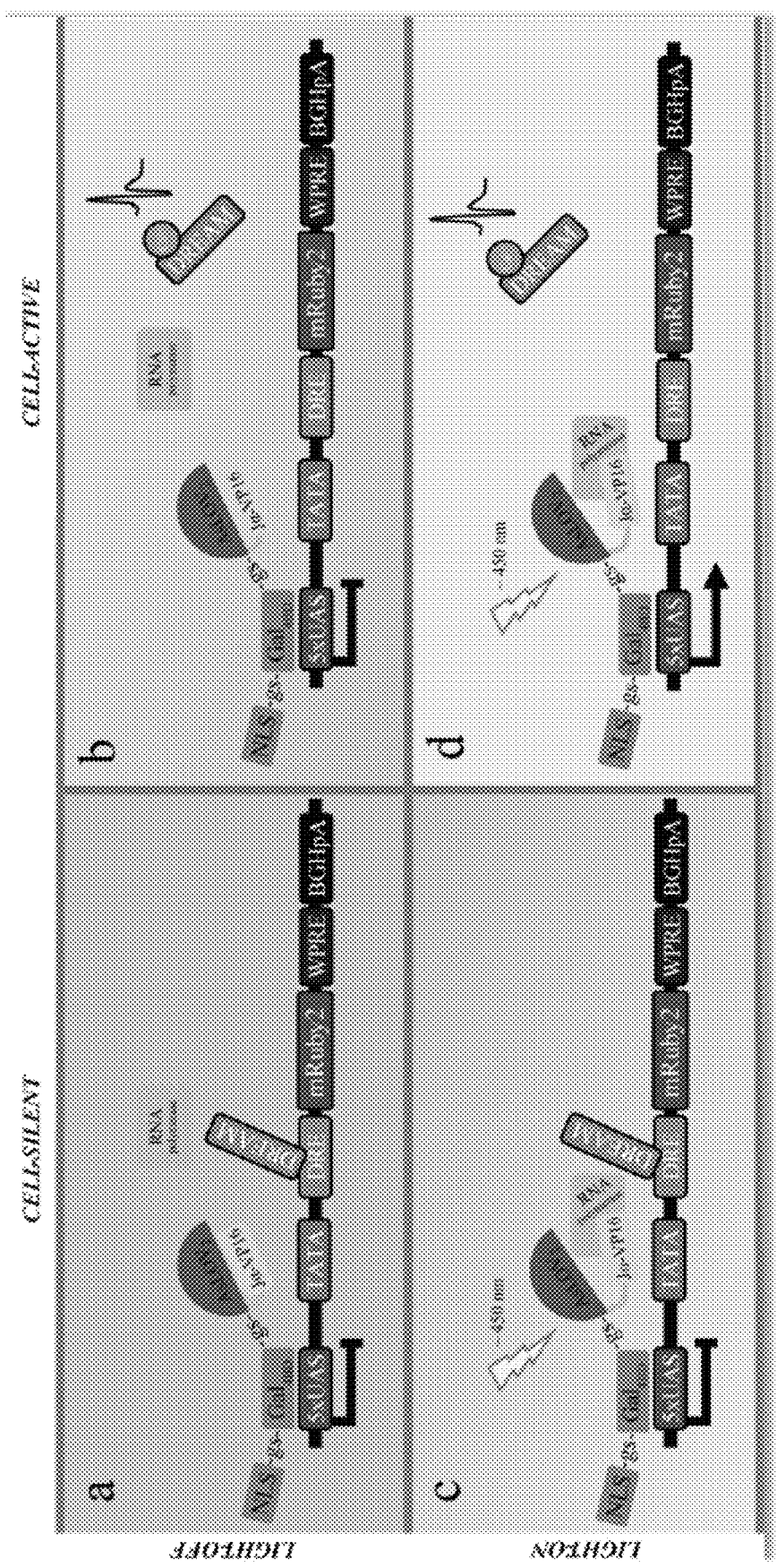
FIGS. 13A-13D depict a schematic of an embodiment of a CLiCK optogenetic system described herein. System. CLiCK$_{TF}$: 13A and 13C. Dark state configuration provides steric block of VP16. Exposure to blue light leads to unwinding of Jα-VP16 segment for transcriptional complex formation with RNA polymerase. 13B and 13D. CLiCK$_{Act}$: Downstream activity-dependent target. Represses gene in absence of neural activity. Nuclear Ca2+ transients leads to derepression of gene
Figure 14:
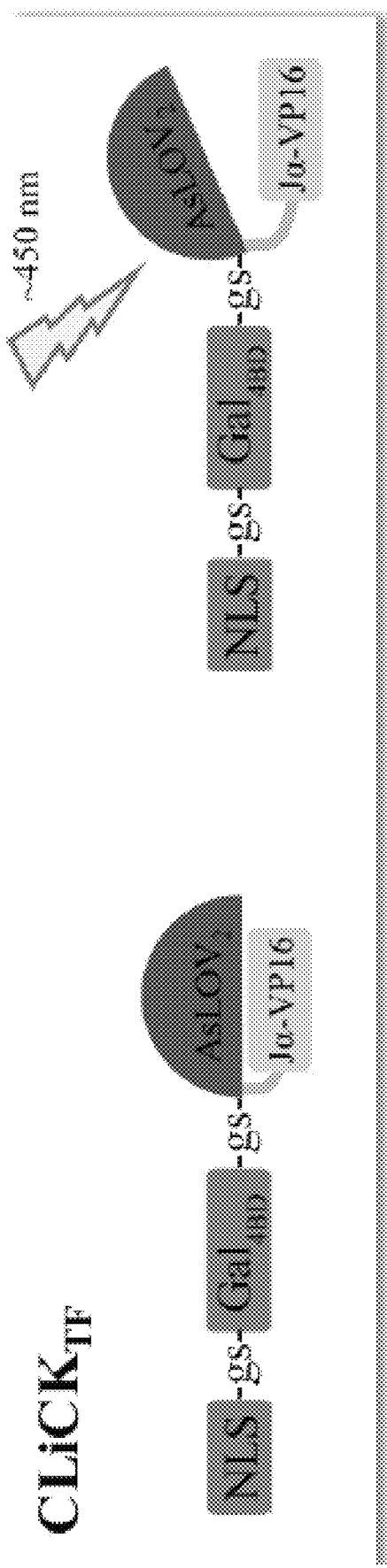
FIG. 14 depicts a schematic of an embodiment of a CLiCK optogenetic system described herein, having the following component parts. Phototropin AsLOV2: Phototropin from *Avena Sativa* (oat). Jα-segment dissociates and unwinds from β-sheet of AsLOV2 following exposure to blue light (450 nm peak absorbance) (Salomon, Biochemistry 2000 39(31); Swartz, J Bio Chem 2001 276(39)). Photoproduct formation <250 ms, dark state recovery <1 sec. Transcriptional activation domain VP16: Strong transcriptional activation domain. Small minimal activation motif DALDDFDLDML (SEQ ID NO: 2) with similar net charge of Jα-segment. Can activate transcription from remote as well as proximal positions [Seipel, EMBO J 1992 11(13)]. Binding domain NLS-gs-Gal4BD-gs-: NLS. Flexible gslinkers [Chen, Adv Drug Deliv Rev 2013 65(10)]. Jα-VP16 fusion sequences: Amino acid alignment preserving: VP16 critical F442 [Cress & Triezenberg, Sci1991 251(4989)]; AsLOV2-Jα critical 1539, A542, and A543 [Lungu, Chem & Bio 2012 19(4)]; Minimized charge/polarity changes; Distal portion of Jα-segment [Lungu, Chem & Bio 2012 19(4)]. Constitutive promoter (CBA). Downstream target: 5×UAS; mRuby2.
Figure 15A:
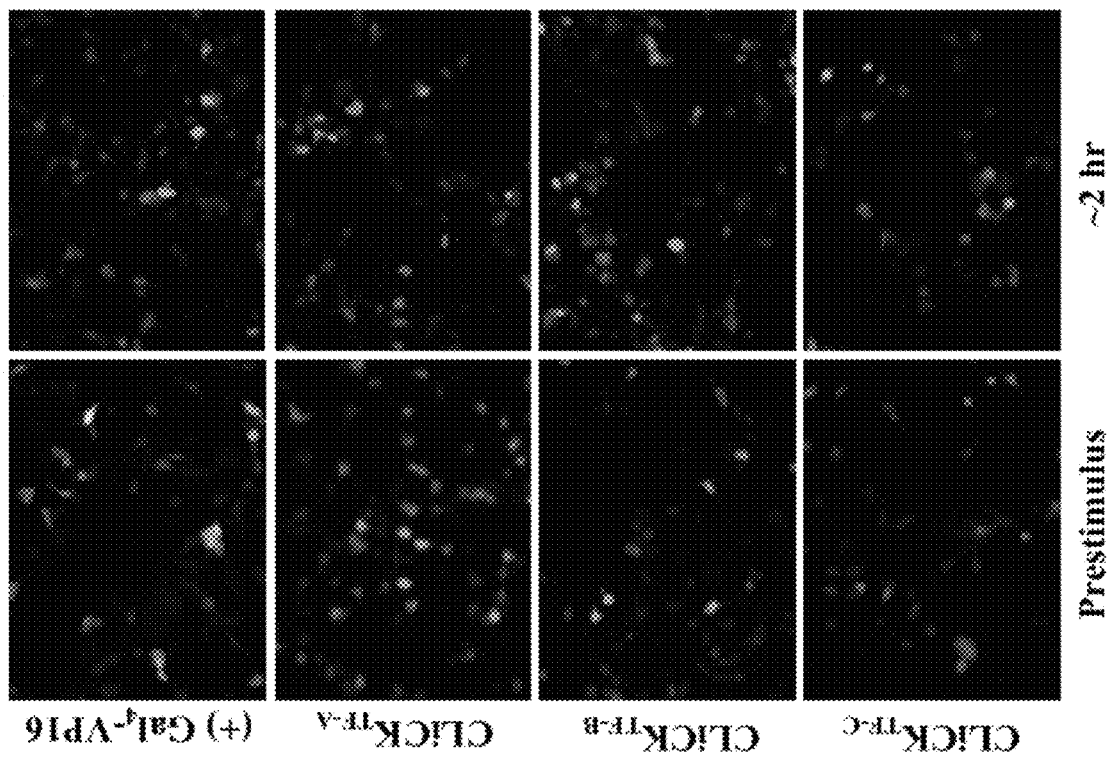
FIGS. 15A-15B depict results of the assays using the embodiment of the CLiCK optogenetic system described in FIG. 14. 15A. HEK Assay: (Magneto) transfection at 70% confluency with DNA complex of pCBA-CLiCK$_{TF}$-A/B/C (1 of 3 CLiCKTFversions); pUAS-mRuby2 (downstream target); and pmaxGFP (transfection marker). Cells were kept in light-tight containers immediately following transfection and handled under red light and incubated at 37 C for two days. 2×1 second exposures to blue LED array (450 nm peak, ~14 mW). Imaging was performed using a Nikon inverted microscope and acquisition settings were calibrated to control condition and kept constant across all conditions.
Figure 15B:
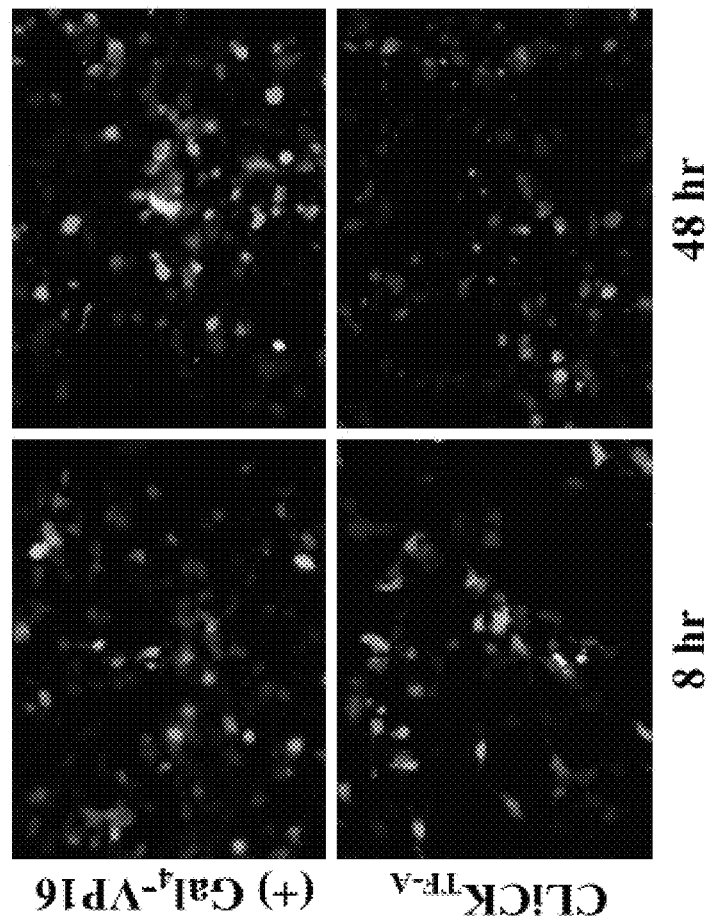
Figure 16:
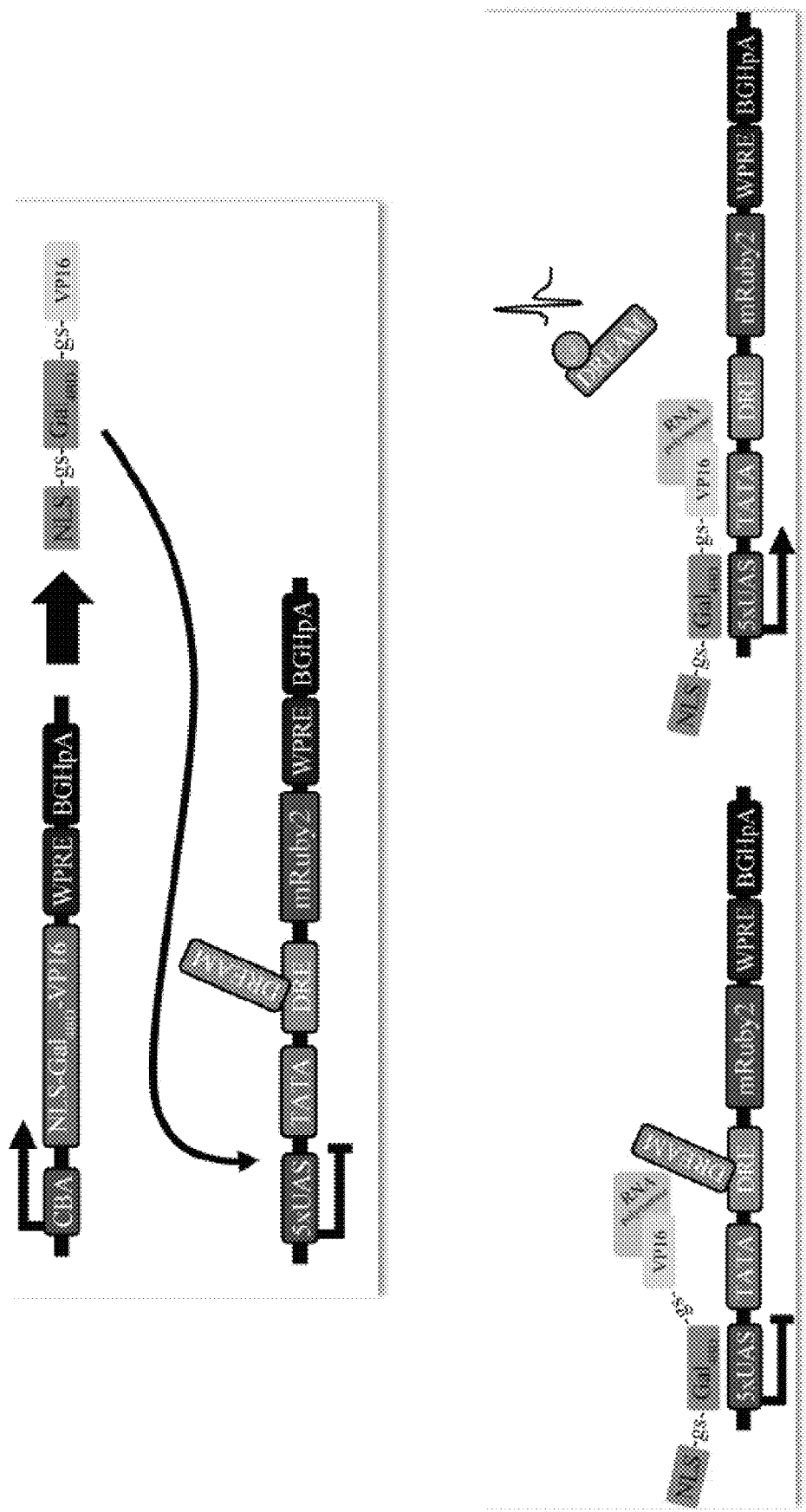
FIG. 16 depicts a schematic of an embodiment of a CLiCK optogenetic system described herein, having the following component parts. DREAM/DRE (Downstream Responsive Element Antagonist Modulator): Direct Ca2+ transcriptional response element (10 s ms) [Carrión, Nat 398(6722)]; Ca2+ causes dimerization and release from DNA binding site [Lusin, Biochem 2008 47(8)]; Endogenously expressed throughout the brain [Carrión, Nat 398 (6722); Mellström, Physiol Rev 2008 88; An, Nat 2000 403(6769); Link, J Neuro 2004 24(23); Ruiz-Gomez, J Biol Chem 2007 282(2)]. DRE sequences: ICER highest affinity with DREAM [Ledo, Biochimet Biophysic2000 1498]; Consensus [Carrión, Mol Cell Bio 1998 18(12)]; Inserted into 5×UAS-mRuby2 expression vector (~40 bpfrom TATA box [Carrión, Mol Cell Bio 1998 18(12)]. NLS-Gal4BD-VP16 transcription factor: Constitutive promoter (CBA).
Figure 17:
FIG. 17 depicts verification against transcriptional interference by DRE sequence using the embodiment of the CLiCK optogenetic system described in FIG. 16. HEK Assay: (Magneto) transfection at 70% confluency with DNA complex of pUAS-DREicer/con-mRuby2 (1 of 2 CLiCK-Actversions) or pUAS-mRuby2 (+ control); pCBA-Gal4BD-VP16; and pmaxGFP (transfection marker), and incubated at 37 C for two days. Imaging was performed using a Nikon inverted microscope Acquisition settings calibrated to control condition and kept constant across all conditions.
Figure 18:
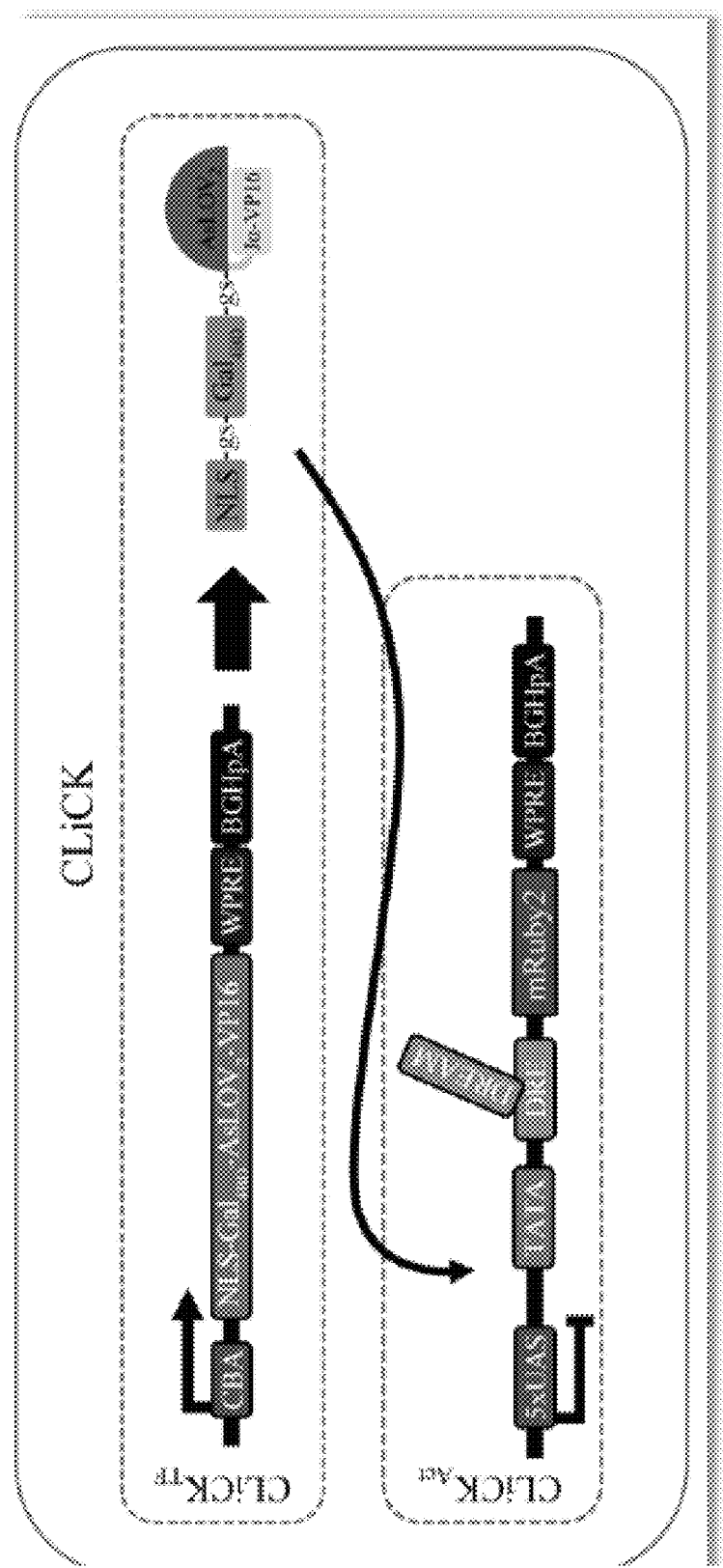
FIG. 18 depicts a schematic of an embodiment of a CLiCK optogenetic system described herein used for performing an in vitro neuron assay. 0 DIV dissociated primary cortical neurons from E15 mice. 3 DIV neurons triple transduce AAV2/9-CBA-CLiCKTF, AAV2/9-CLiCKAct, and AAV2/9-CAG-eGFP. Cells were kept in light-tight containers immediately following transfection and handled under red light. 7 DIV neurons assayed.
Figures 19A, 19B, 19C, 19D:
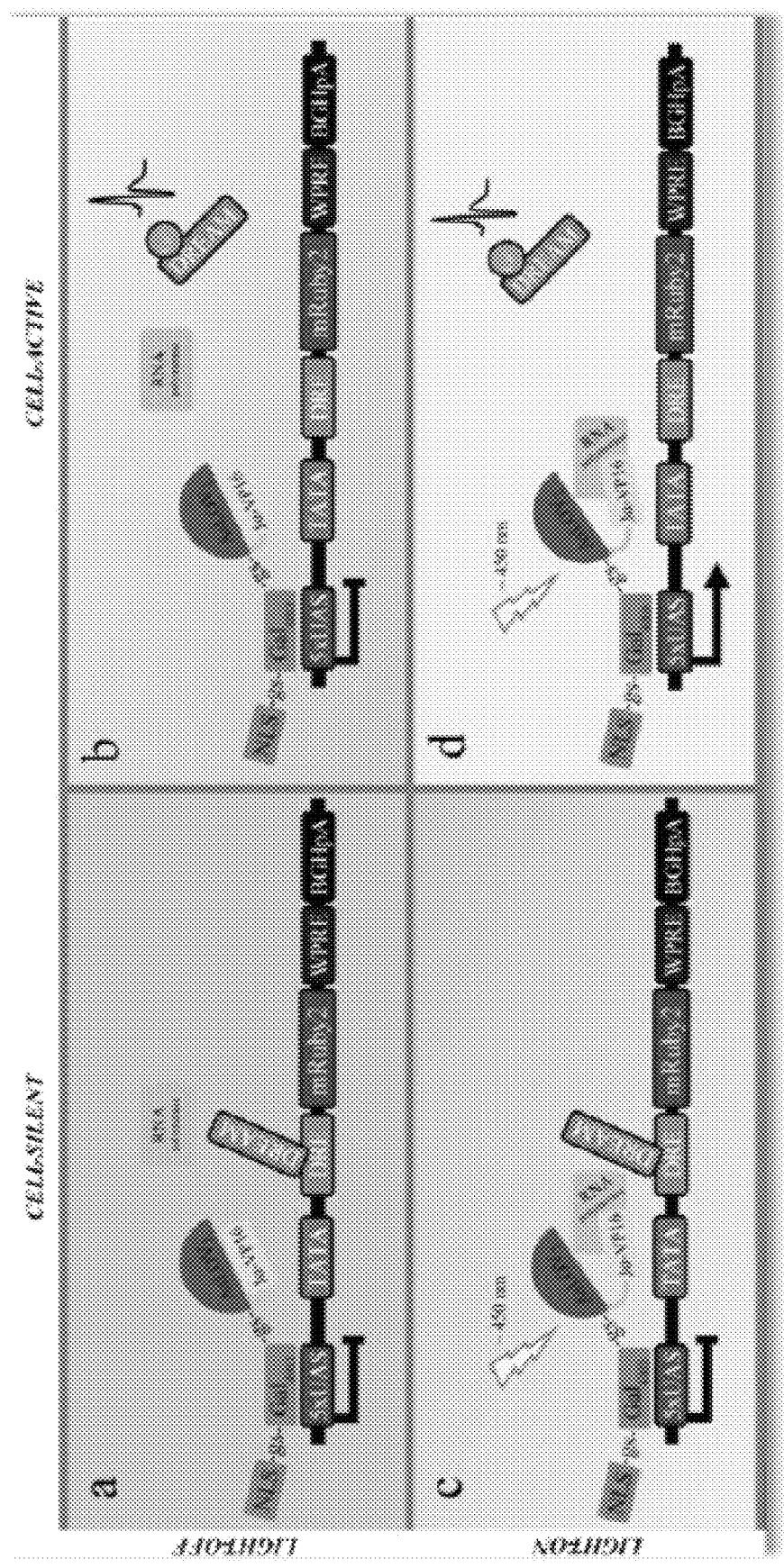
Figures 20A, 20B:
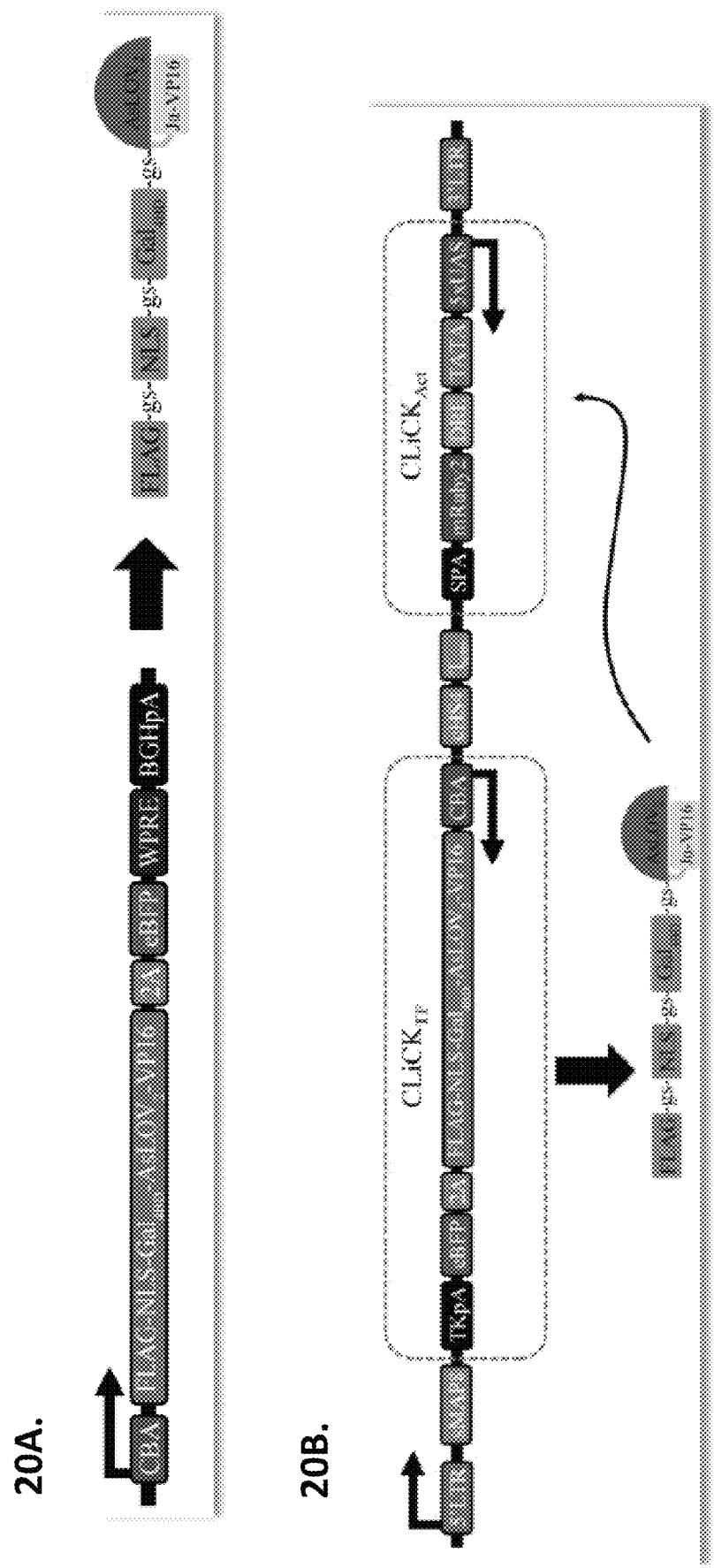
FIGS. 20A-20D show results from in vitro and in vivo assays using an embodiment of the CLiCK optogenetic system. 20A-20B. Schematics of an embodiment of the CLiCK optogenetic system having the following component parts. CLiCK$_{TF}$-Epitope tag: FLAG-NLSmyc-Gal4BD-; NLSmyc [Tian, Gene Therapy 2009 16(7)]; Reporter: IRES/2A-eBFP. Other modifications to: CLiCK$_{TF}$ include, but are not limited to, new Jα-VP16/AD fusion alignments and/or Jα mutation for accelerated photocycle [Diensthuber, ACS Syn Bio 2014 9]; CLiCK$_{Act}$ include, but are not limited to, DRE repeats; CLiCK system include, but are not limited to, a dual independent promoter, gateway cloning, and/or lentivirus usage. 20C. In vitro assay modifications include, but are not limited to, using a GECI (Genetically Encoded Calcium Indicator) and/or a voltage-sensitive dye. 20D. In vivo assay modifications include, but are not limited to, measuring activity only using, for example, a Thy1-COP3/EFYP (JAX) mouse having vChR1 [Ex~535 nm] and expressed in cortical and hippocampal (CA1/3) neurons; measuring light only using, for example, mac rhodopsin [Ex~470 nm]; and measuring activity and light, using, for example, a Thy1-COP4/EYFP (JAX/Ritt) mouse having ChR2 [Ex~470 nm] and expressed in cortical and hippocampal (CA1/3) neurons.
Figure 20C:
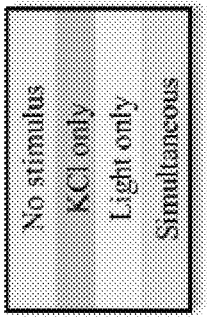
Figure 20D:
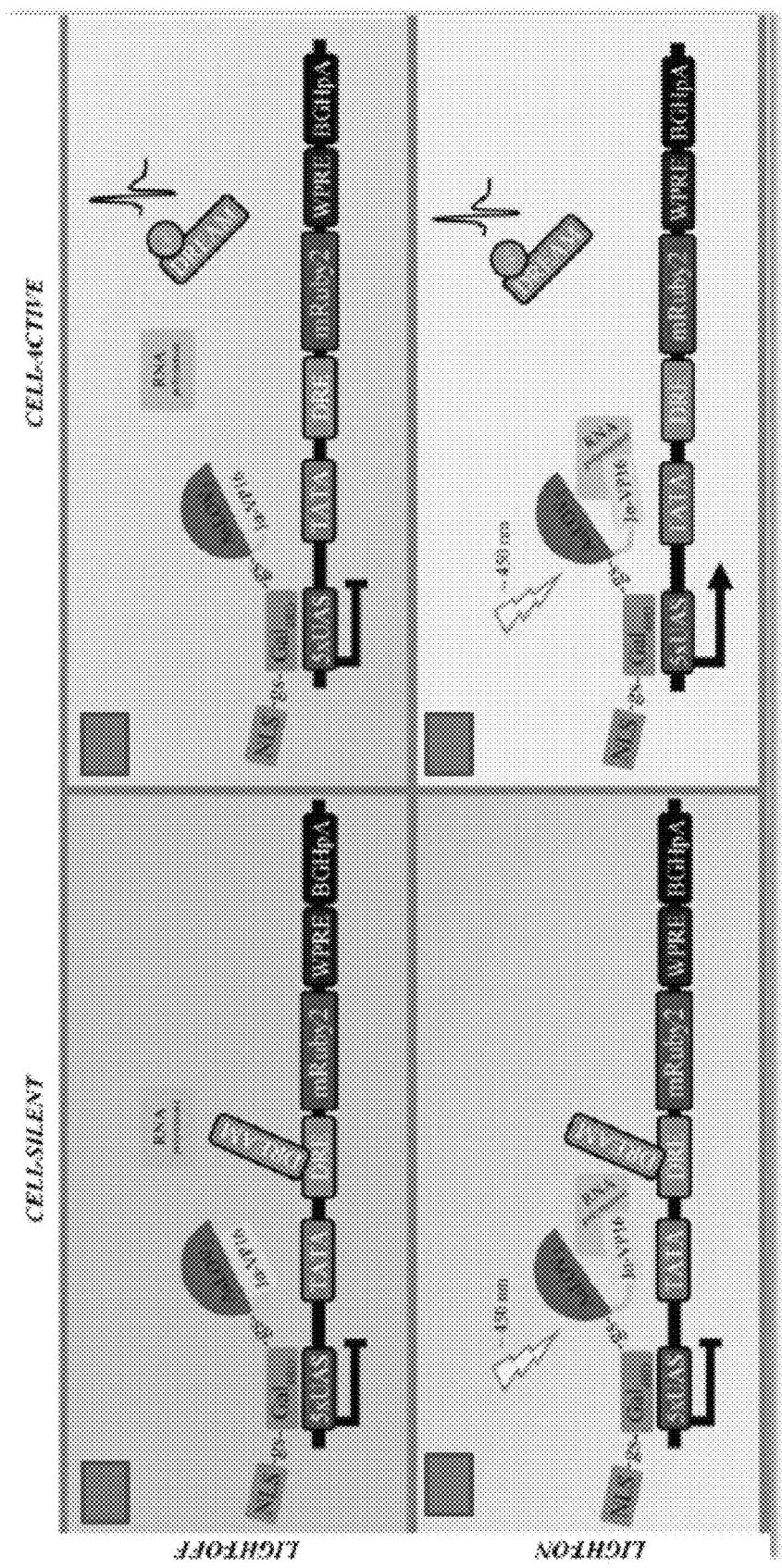
Figure 21:
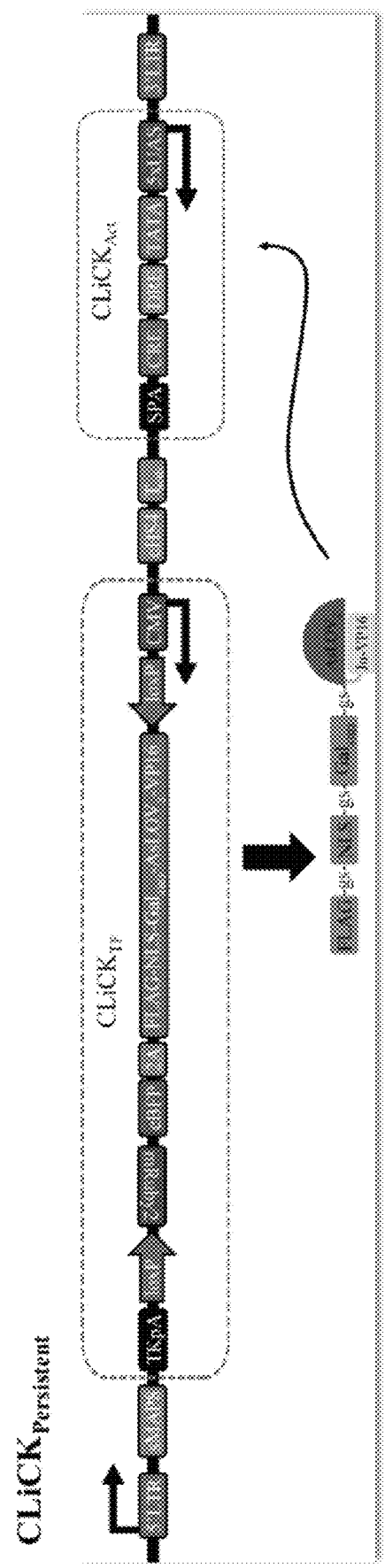
FIG. 21 depicts a schematic of an embodiment of a CLiCK optogenetic system described herein having, for example, indefinite gene expression ("CLiCK$_{Persistent}$") or having gene expression persist until pharmacologically reset ("CLiCK$_{Persistent-Pharm}$").
Figure 22:
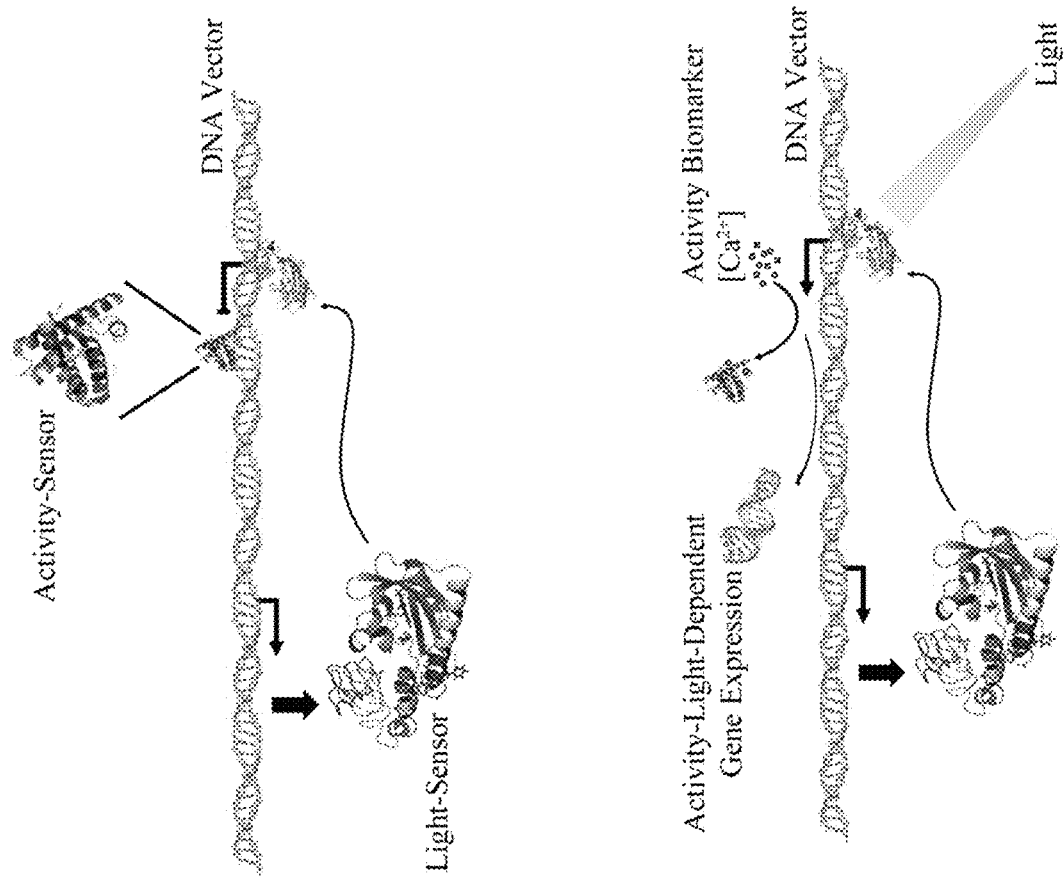
FIG. 22 depicts a schematic representation of CLiCK [Ca$^{2+}$ Light Coincidence Knock-in/out] comprising two gating components: (i) an activity-sensor that functions to inhibit gene expression in the absence of neural activity and (ii) a light-sensor that inhibits gene expression in the absence of light giving researchers the ability to control exactly when an activity neuron should express the encoded gene of interest.
Figure 24A:
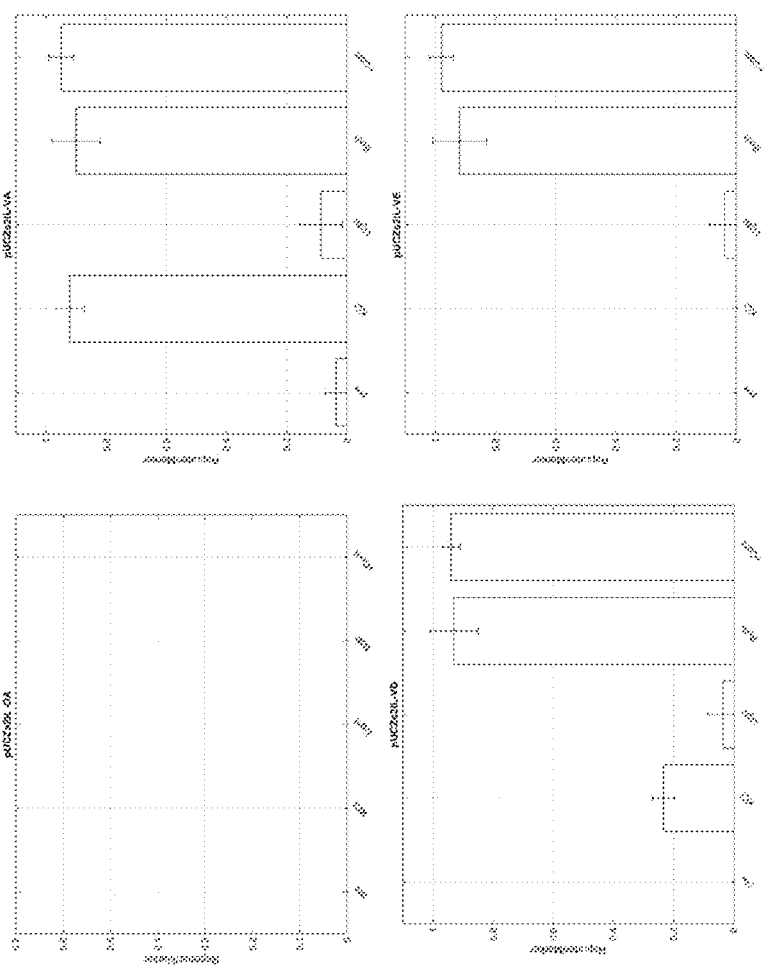
FIGS. 24A-24E show an embodiment of a CLiCK system.
Figure 24B:
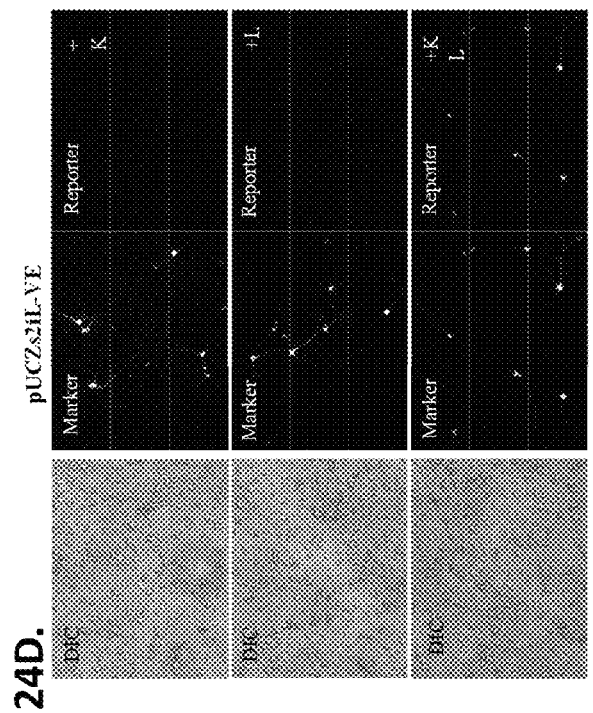
Figure 24C:
Figure 24D:
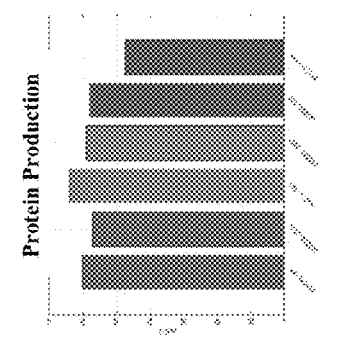
Figure 24E:
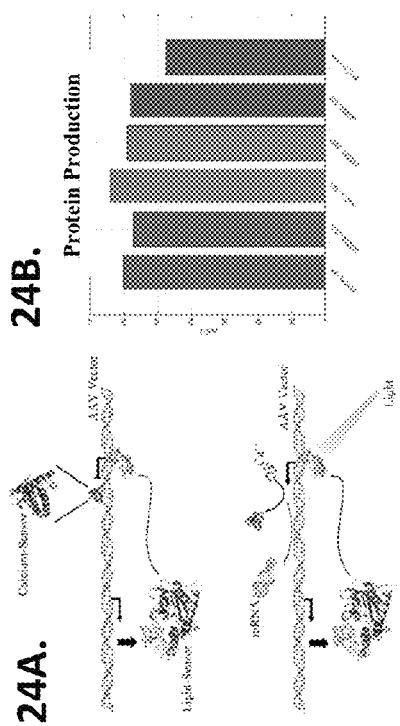
Figure 25:
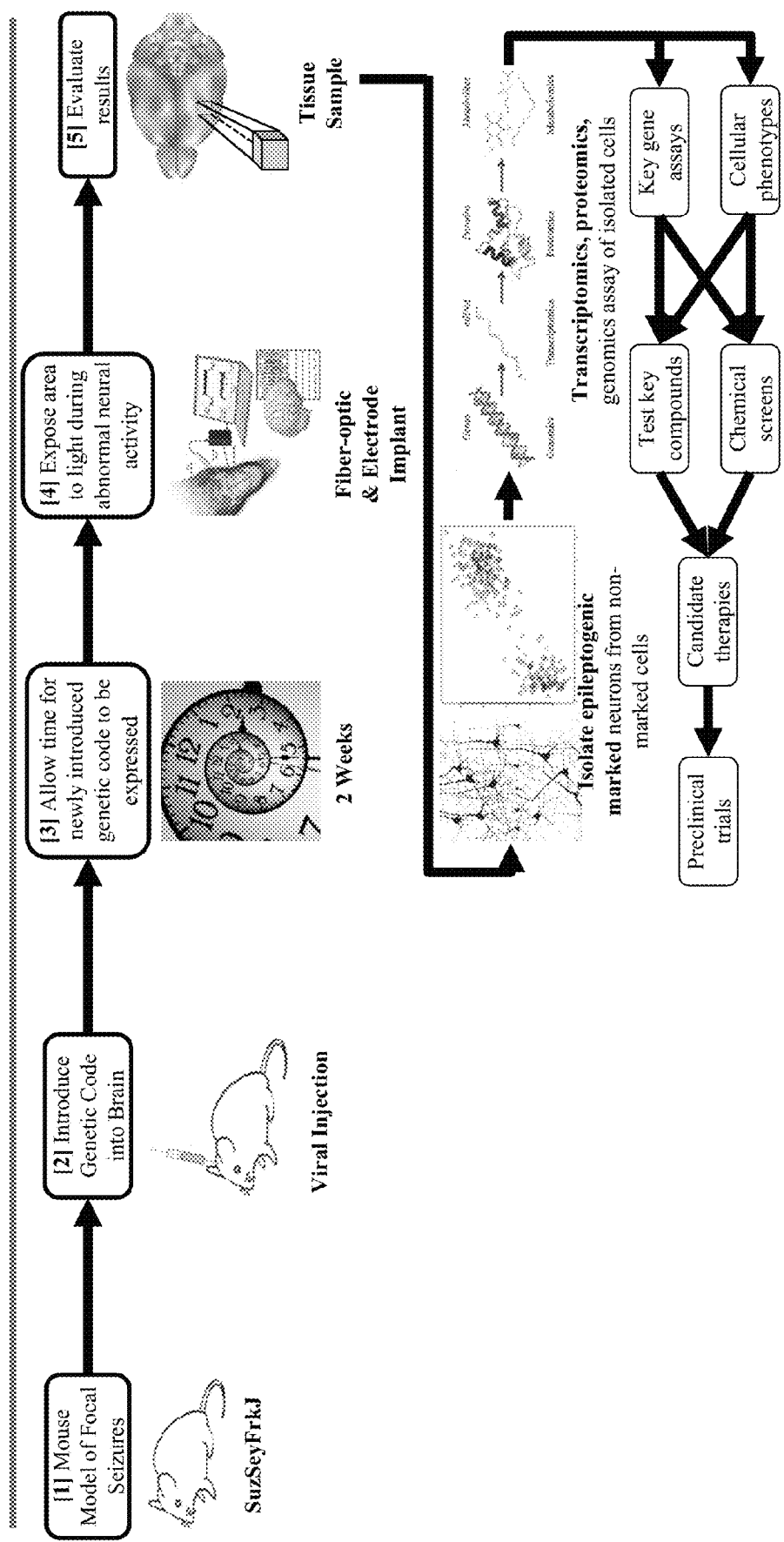
FIG. 25 depicts an exemplary model for implementing this technology into drug discovery begins by choosing, for example, a neurological disease model. In this example, the Suzsey mouse model is used which is a model of temporal lobe focal point seizures. Next, the genetic code of a CLiCK system is introduced into the brain via, for example, viral injection followed by a period of incubation allowing the new genetic material to be taken up by the neurons. To pair light to epileptic neural activity, a dual implant containing a fiber optic for the passage of light and an electrode for monitoring neural activity is used. This allows for triggering of a light pulse by epileptic events, thereby marking the neurons actively driving the epileptic event and allowing us to isolate them from within the cellular matrix. With the neurons marked, tissue samples are collected and the phenotype tagged neurons isolated. These neurons, which contain abnormal activity-dependent gene expression, can be studied at the genomic, transcriptomic, and proteomic level, where prior to the systems and data described herein, would be too subtle to detect in larger heterogeneous tissue samples. These data can then be used in drug discovery to develop key gene assays and identify cellular phenotypes from which chemical screens and key compounds can be developed and tested as candidate therapies for preclinical trails. This technology can be used to mark and isolate abnormally active neurons in an array of neurological disorders such as schizophrenia, dementia, Parkinson's disease, depression, ADHD all exhibit periods of abnormal neural activity patterns.

After verifying the light-dependency of CLiCK in HEK cells, co-dependency of CLiCK was tested in EIS rat primary cortical neuron culture. Unlike HEK cells, DREAM is endogenously expressed in neurons making expression of mRuby2 both light- and activity-dependent as illustrated in FIG. 7Ba-7Bd. Spiking was induced in neurons by brief application of 40 mM KCl to the media. Spontaneous spiking in negative controls (FIGS. 10A and 10C) was guarded against by applying 1 μM of TTX to the media 45 mins prior to assaying. Cells were triple transduced with AAV2/9-CLiCKT F, AAV2/9-CLiCKActmRbuy2, AAV2/9-eGFP. FIGS. 10A-10D demonstrate co-dependency of mRuby2 expression on simultaneous exposure to light and neural activity. These data are the first to demonstrate activity-dependent regulation of a gene within experimentally defined windows of time as small as a few seconds. The striking absence of mRuby2 outside of simultaneous photo-KCl stimulation suggest tight regulation of the GOI in the absence of either one, or both, of the conditional stimuli (FIGS. 10A-10C).

Successful designs of CLiCK can be packaged into lentivirus and transduced into mouse CA1 hippocampal neurons. CLiCK can be used to drive the expression of mRuby2 in an activity- and light-dependent manner. ChR-eGFP mouse lines are purchased from, for example, The Jackson Laboratory. CLiCK is packaged into lentivirus (L-CLiCK). L-CLiCK is injected bilaterally into mouse CA1 region of the hippocampus at 100 nL/min for a total volume of 600 nL. Following viral injection, a light fiber is implanted unilaterally above the CA1 neural layer. An incubation period of two weeks is given for viral transduction. At the end of the incubation period, mice undergo photostimulation using either 473 or 630 nm wavelength laser appropriate to the particular ChR expressed in CA1 neurons. Photostimulation is carried out in a laser-safe room at 12 mW at 10 Hz for 500 ms and repeated 5 times with 10 second inter-stimulus intervals. After stimulation, mice return to their cage for a period of 24 hrs at which point they are euthanized and perfused with saline and then 10% paraformaldehyde. After perfusion, brains are extracted and flash frozen in dry ice chilled 2-methyl-butane to stabilize fluorescence, sectioned on a cryostat, and mounted on slides for review under fluorescent microscopy.

Cell counts of mRuby2 and eGFP expressing CA1 neurons are made bilaterally using standard fluorescent microscopy. mRuby2 expression counts between experimental groups (received light, no light) while controlling for eGFP expression counts are analyzed using ANOVA. Expression counts between mRuby2 and eGFP within experimental groups (received light, no light) are measured using paired sample t-test. Photostimulated mice expressing CLiCK and rsChR or CLiCK and ClChR do not express mRuby2. mRuby2 is only expressed in photostimulated mice co-expressing CLiCK and ChR2 as a coincidence detector of light and neural activity.

Given the short window of time in which mRNA can be transcribed from the mRuby2 gene, expression levels of mRuby2 may be difficult to visualize. Extending the duration of single photostimulation trials (e.g. 500 ms exposure to 5 second exposure) would limit the temporal resolution at which CLiCK can be evaluated at. Alternatively, increasing the number of applications of the photostimulation would increase the overall mRNA transcribed while keeping the time window for transcription constant. For example, instead of 5 applications of 500 ms photostimulation 20 applications can be used. Additionally, immunolabeling of primary RFP-antibody and secondary antibody tag can be used to increase fluorescence. In some embodiments, the same animal is used for experiment and control. By applying light in only one hemisphere, the contralateral hemisphere can be used as a dark control. Though this approach will halve the number of animals needed, light could leak into the control "dark" hemisphere causing unintended photostimulation and thus confounding controls and should be considered based on the location of interest in the brain. That is, regions near sagittal midline will likely have light leak across hemispheres. In other embodiments, separate animals are used for experimental and control groups.

Component Parts for Use with the Modules and Systems

Promoters and promoter sequences are required for use of the various modules and components of the CLiCK systems described herein. The term "promoter," as used herein, refers to any nucleic acid sequence that regulates the expression of another nucleic acid sequence by driving transcription of the nucleic acid sequence, which can be a heterologous target gene encoding a protein or an RNA. Promoters can be constitutive, inducible, repressible, tissue-specific, or any combination thereof. A promoter is a control region of a nucleic acid sequence at which initiation and rate of transcription of the remainder of a nucleic acid sequence are controlled. A promoter can also contain genetic elements at which regulatory proteins and molecules, such as RNA polymerase and other transcription factors, can bind.

A promoter can be said to drive expression or drive transcription of the nucleic acid sequence that it regulates. The phrases "operably linked," "operatively positioned," "operatively linked," "under control," and "under transcriptional control" indicate that a promoter is in a correct functional location and/or orientation in relation to a nucleic acid sequence it regulates to control transcriptional initiation and/or expression of that sequence. In addition, in various embodiments of the invention, a promoter can be used in conjunction with an "enhancer," which refers to a cis-acting regulatory sequence involved in the transcriptional activation of a nucleic acid sequence downstream of the promoter. The enhancer can be located at any functional location before or after the promoter, and/or the encoded nucleic acid.

A promoter can be one naturally associated with a gene or sequence, as can be obtained by isolating the 5' non-coding sequences located upstream of the coding segment and/or exon of a given gene or sequence. Such a promoter can be referred to as "endogenous." Similarly, in some embodiments, an enhancer can be one naturally associated with a nucleic acid sequence, located either downstream or upstream of that sequence.

Alternatively, certain advantages are gained by positioning a coding nucleic acid segment under the control of a "recombinant promoter" or "heterologous promoter," which refer to a promoter that is not normally associated with the encoded nucleic acid sequence it is operably linked to in its natural environment. A recombinant or heterologous enhancer refers to an enhancer not normally associated with a given nucleic acid sequence in its natural environment. Such promoters or enhancers can include promoters or enhancers of other genes; promoters or enhancers isolated from any other prokaryotic, viral, or eukaryotic cell; and synthetic promoters or enhancers that are not "naturally occurring," i.e., comprise different elements of different transcriptional regulatory regions, and/or mutations that alter expression through methods of genetic engineering that are known in the art. In addition to producing nucleic acid sequences of promoters and enhancers synthetically, promoter sequences can be produced using recombinant cloning and/or nucleic acid amplification technology, including PCR, in connection with the systems and modules disclosed herein (see, e.g., U.S. Pat. Nos. 4,683,202, 5,928,906, each incorporated herein by reference). Furthermore, it is contemplated that control sequences that direct transcription and/or expression of sequences within non-nuclear organelles such as mitochondria, chloroplasts, and the like, can be employed as well.

If a promoter is an "inducible promoter", as defined herein, then the rate of transcription is modified in response to an inducing agent or inducer. In contrast, the rate of transcription is not regulated by an inducer if the promoter is a constitutive promoter. The term "constitutive" when made in reference to a promoter means that the promoter is capable of directing transcription of an operably linked nucleic acid sequence in the absence of a stimulus (e.g., heat shock, chemicals, agents, light, etc.). Typically, constitutive promoters are capable of directing expression of a nucleic acid sequence in substantially any cell and any tissue. In contrast, the term "regulateable" or "inducible" promoter referred to herein is one which is capable of directing a level of transcription of an operably linked nucleic acid sequence in the presence of a stimulus (e.g., heat shock, chemicals, light, agent etc.) which is different from the level of transcription of the operably linked nucleic acid sequence in the absence of the stimulus.

A promoter may be regulated in a tissue-specific or tissue preferred manner such that it is only active in transcribing the associated coding region in a specific tissue type(s). The term "tissue specific" as it applies to a promoter refers to a promoter that is capable of directing selective expression of a nucleotide sequence of interest to a specific type of tissue (e.g., liver) in the relative absence of expression of the same nucleotide sequence of interest in a different type of tissue (e.g., kidney). Tissue specificity of a promoter may be evaluated by, for example, operably linking a reporter gene to the promoter sequence to generate a reporter construct, introducing the reporter construct into the genome of an organism, e.g. an animal model such that the reporter construct is integrated into every tissue of the resulting transgenic animal, and detecting the expression of the reporter gene (e.g., detecting mRNA, protein, or the activity of a protein encoded by the reporter gene) in different tissues of the transgenic animal. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter, which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. The term "minimal promoter" as used herein refers to the minimal nucleic acid sequence comprising a promoter element while also maintaining a functional promoter. A minimal promoter can comprise an inducible, constitutive or tissue-specific promoter.

As described herein, an "inducible promoter" is one that is characterized by initiating or enhancing transcriptional activity when in the presence of, influenced by, or contacted by an inducer or inducing agent. An "inducer" or "inducing agent," as defined herein, can be endogenous, or a normally exogenous compound or protein that is administered in such a way as to be active in inducing transcriptional activity from the inducible promoter. In some embodiments, the inducer or inducing agent, i.e., a chemical, a compound or a protein, can itself be the result of transcription or expression of a nucleic acid sequence (i.e., an inducer can be a transcriptional repressor protein expressed by another component or module), which itself can be under the control or an inducible promoter. In some embodiments, an inducible promoter is induced in the absence of certain agents, such as a repressor. Examples of inducible promoters include, but are not limited to, those regulated by tetracycline, metallothionine, ecdysone, hormones, and other steroid-responsive promoters, rapamycin responsive promoters and the like.

Inducible promoters useful in the systems, compositions, and methods described herein can be capable of functioning in both prokaryotic and eukaryotic host organisms. In some embodiments of the different aspects described herein, mammalian inducible promoters are included, although inducible promoters from other organisms, as well as synthetic promoters designed to function in a prokaryotic or eukaryotic host can be used. Exemplary environmental inducers include exposure to heat (i.e., thermal pulses or constant heat exposure), various steroidal compounds, divalent cations (including $Cu^{2+}$ and $Zn^{2+}$), galactose, tetracycline, IPTG (isopropyl-β-D thiogalactoside), as well as other naturally occurring and synthetic inducing agents and gratuitous inducers.

In some embodiments, the systems and their component modules comprise suitable inducible promoters that can be dependent upon transcriptional activators that, in turn, are reliant upon an environmental or exogenous inducer. In other embodiments, the inducible promoters can be repressed by a transcriptional repressor, which itself is rendered inactive by an environmental inducer, such as the product of a sequence driven by another promoter. Thus, unless specified otherwise, an inducible promoter can be one that is induced by an inducing agent that positively activates a transcriptional activator, or one which is derepressed by an inducing agent that negatively regulates a transcriptional repressor. In such embodiments of the various aspects described herein where it is required to distinguish between an activating and a repressing inducing agent, explicit distinction will be made.

Inducible promoters useful in the methods and systems described herein also include those that are repressed by "transcriptional repressors," which are subject to inactivation by the action of environmental, intracellular or external agents, or the product of another gene. Such inducible promoters may also be termed "repressible promoters" where it is required to distinguish between other types of promoters in a given module or component of the systems described herein. Examples include prokaryotic repressor molecules that can transcriptionally repress eukaryotic promoters that have been engineered to incorporate appropriate repressor-binding operator sequences. Preferred repressors for use in the modules and methods described herein are sensitive to inactivation by a physiologically benign agent. Thus, for example, where a lac repressor protein is used to control the expression of a promoter sequence that has been engineered to contain a lacO operator sequence, treatment of the host cell with IPTG will cause the dissociation of the lac repressor from the engineered promoter containing a lacO operator sequence and allow transcription to occur. Similarly, where a tet repressor is used to control the expression of a promoter sequence that has been engineered to contain a tetO operator sequence, treatment of the host cell with tetracycline will cause dissociation of the tet repressor from the engineered promoter and allow transcription of the sequence downstream of the engineered promoter to occur. Other physiologically responsive repressors known to those of skill in the art are contemplated for conferring physiologically-sensitive expression upon a system, analogous to the effect of Ca2+ on the DRE/DREAM element regulatory pair.

An inducible promoter useful in the methods and systems as described herein can be induced by one or more physiological conditions, such as changes in pH, temperature, radiation, osmotic pressure, saline gradients, cell surface binding, and the concentration of one or more extrinsic or intrinsic inducing agents. The extrinsic inducer or inducing agent can comprise amino acids and amino acid analogs, saccharides and polysaccharides, nucleic acids, protein transcriptional activators and repressors, cytokines, toxins, petroleum-based compounds, metal containing compounds, salts, ions, enzyme substrate analogs, hormones, and combinations thereof. In specific embodiments, the inducible promoter is activated or repressed in response to a change of an environmental condition, such as the change in concentration of a chemical, metal, temperature, radiation, nutrient or change in pH. Thus, an inducible promoter useful in the methods and systems as described herein can be a phage inducible promoter, nutrient inducible promoter, temperature inducible promoter, radiation inducible promoter, metal inducible promoter, hormone inducible promoter, steroid inducible promoter, and/or hybrids and combinations thereof.

The administration or removal of an inducer or repressor as described herein, under the proper permissive or co-stimulated condition, results in a switch between the "on" or "off" states of the transcription of the operably linked heterologous target gene. Thus, as defined herein, the "on" state of a promoter operably linked to a nucleic acid sequence, refers to the state when the promoter is actively driving transcription of the operably linked nucleic acid sequence, i.e., the linked nucleic acid sequence is expressed.

In some embodiments of the systems described herein, ribosome binding sites (RBSs) can be added to one or more modules. RBSs are sequences that promote efficient and accurate translation of mRNAs for protein synthesis, and are also provided for use in the modules and engineered systems described herein to permit modulation of the efficiency and rates of synthesis of the proteins encoded by the system. An RBS affects the translation rate of an open reading frame in two main ways—i) the rate at which ribosomes are recruited to the mRNA and initiate translation is dependent on the sequence of the RBS, and ii) the RBS can also affect the stability of the mRNA, thereby affecting the number of proteins made over the lifetime of the mRNA. Accordingly, one or more ribosome binding site (RBS) can be added to the modules and engineered systems described herein to control expression of proteins.

Terminators are sequences that usually occur at the end of a gene or operon and cause transcription to stop, and are also provided for use in the modules and engineered systems described herein to regulate transcription and prevent transcription from occurring in an unregulated fashion, i.e., a terminator sequence prevents activation of downstream modules by upstream promoters. A "terminator" or "termination signal", as described herein, is comprised of the DNA sequences involved in specific termination of an RNA transcript by an RNA polymerase. Thus, in certain embodiments a terminator that ends the production of an RNA transcript is contemplated. A terminator can be necessary in vivo to achieve desirable message levels.

The most commonly used type of terminator is a forward terminator. When placed downstream of a nucleic acid sequence that is usually transcribed, a forward transcriptional terminator will cause transcription to abort. In some embodiments, bidirectional transcriptional terminators are provided. Such terminators will usually cause transcription to terminate on both the forward and reverse strand. Finally, in some embodiments, reverse transcriptional terminators are provided that terminate transcription on the reverse strand only.

In eukaryotic systems, the terminator region can also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to be more stable and are translated more efficiently. Thus, in those embodiments involving eukaryotes, it is preferred that a terminator comprises a signal for the cleavage of the RNA, and it is more preferred that the terminator signal promotes polyadenylation of the message. The terminator and/or polyadenylation site elements can serve to enhance message levels and/or to minimize read through between modules of the systems described herein. As disclosed herein, terminators contemplated for use in the modules, systems, and methods of use thereof can include any known terminator of transcription described herein or known to one of ordinary skill in the art. Such terminators include, but are not limited to, the termination sequences of genes, such as for example, the bovine growth hormone terminator, or viral termination sequences, such as for example, the SV40 terminator. In certain embodiments, the termination signal encompasses a lack of transcribable or translatable sequence, such as due to a sequence truncation. The terminator used can be unidirectional or bidirectional.

In some embodiments of the aspects described herein, a nucleic sequence encoding a protein degradation tag can be added to the modules and engineered systems described herein to enhance protein degradation of a protein. As defined herein, a "degradation tag" is a genetic addition to the end of a nucleic acid sequence that modifies the protein that is expressed from that sequence, such that the protein undergoes faster degradation by cellular degradation mechanisms. Thus, such protein degradation tags 'mark' a protein for degradation, thus decreasing a protein's half-life.

One of the useful aspects of degradation tags is the ability to detect and regulate gene activity in a time-sensitive manner. Such protein degradation tags can operate through the use of protein-degrading enzymes, such as proteases, within the cell. In some embodiments, the tags encode a sequence of about eleven amino acids at the C-terminus of a protein, wherein said sequence is normally generated in *E. coli* when a ribosome gets stuck on a broken ("truncated") mRNA. Without a normal termination codon, the ribosome can't detach from the defective mRNA. A type of RNA known as ssrA ("small stable RNA A") or tmRNA ("transfer-messenger RNA") rescues the ribosome by adding the degradation tag followed by a stop codon. This allows the ribosome to break free and continue functioning. The tagged, incomplete protein can get degraded by the proteases ClpXP or ClpAP. Although the initial discovery of the number of amino acids encoding for an ssRA/tmRNA tag was eleven, the efficacy of mutating the last three amino acids of that system has been tested. Thus, the tags AAV, ASV, LVA, and LAA are classified by only three amino acids.

In some embodiments, the protein degradation tag is an ssrA tag. In some embodiments, the protein degradation tag is an LAA variant. In some embodiments, the protein degradation tag is an AAV variant. In some embodiments, the protein degradation tag is an ASV variant.

The terms "nucleic acids" and "nucleotides" refer to naturally occurring or synthetic or artificial nucleic acid or nucleotides and any combinations thereof. The terms "nucleic acids" and "nucleotides" comprise deoxyribonucleotides or ribonucleotides or any nucleotide analogue and polymers or hybrids thereof in either single- or doublestranded, sense or antisense form. As will also be appreciated by those in the art, many variants of a nucleic acid can be used for the same purpose as a given nucleic acid. Thus, a nucleic acid also encompasses substantially identical nucleic acids and complements thereof. Nucleotide analogues include nucleotides having modifications in the chemical structure of the base, sugar and/or phosphate, including, but not limited to, 5-position pyrimidine modifications, 8-position purine modifications, modifications at cytosine exocyclic amines, substitution of 5-bromo-uracil, and the like; and 2'-position sugar modifications, including but not limited to, sugar-modified ribonucleotides in which the 2'-OH is replaced by a group selected from H, OR, R, halo, SH, SR, NH2, NHR, NR2, or CN. shRNAs also can comprise non-natural elements such as non-natural bases, e.g., ionosin and xanthine, nonnatural sugars, e.g., 2'-methoxy ribose, or non-natural phosphodiester linkages, e.g., methylphosphonates, phosphorothioates and peptides.

The term "nucleic acid sequence" or "oligonucleotide" or "polynucleotide" are used interchangeably herein and refers to at least two nucleotides covalently linked together. The term "nucleic acid sequence" is also used inter-changeably herein with "gene", "cDNA", and "mRNA". As will be appreciated by those in the art, the depiction of a single nucleic acid sequence also defines the sequence of the complementary nucleic acid sequence. Thus, a nucleic acid sequence also encompasses the complementary strand of a depicted single strand. Unless otherwise indicated, a particular nucleic acid sequence also implicitly encompasses conservatively modified variants thereof (e.g., degenerate codon substitutions) and complementary sequences, as well as the sequence explicitly indicated. As will also be appreciated by those in the art, a single nucleic acid sequence provides a probe that can hybridize to the target sequence under stringent hybridization conditions. Thus, a nucleic acid sequence also encompasses a probe that hybridizes under stringent hybridization conditions. The term "nucleic acid sequence" refers to a single or double-stranded polymer of deoxyribonucleotide or ribonucleotide bases read from the 5'- to the 3'-end. It includes chromosomal DNA, self-replicating plasmids, infectious polymers of DNA or RNA and DNA or RNA that performs a primarily structural role. "Nucleic acid sequence" also refers to a consecutive list of abbreviations, letters, characters or words, which represent nucleotides. Nucleic acid sequences can be single stranded or double stranded, or can contain portions of both double stranded and single stranded sequence. The nucleic acid sequence can be DNA, both genomic and cDNA, RNA, or a hybrid, where the nucleic acid sequence can contain combinations of deoxyribo- and ribo-nucleotides, and combinations of bases including uracil, adenine, thymine, cytosine, guanine, inosine, xanthine hypoxanthine, isocytosine and isoguanine. Nucleic acid sequences can be obtained by chemical synthesis methods or by recombinant methods. A nucleic acid sequence will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages in the nucleic acid sequence. Other analog nucleic acids include those with positive backbones; non-ionic backbones, and non-ribose backbones, including those described in U.S. Pat. Nos. 5,235,033 and 5,034,506, which are incorporated by reference. Nucleic acid sequences containing one or more non-naturally occurring or modified nucleotides are also included within one definition of nucleic acid sequences. The modified nucleotide analog can be located for example at the 5'-end and/or the 3'-end of the nucleic acid sequence. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g. 5-(2-amino) propyl uridine, 5-bromo uridine; adenosines and guanosines modified at the 8-position, e.g. 8-bromo guanosine; deaza nucleotides, e.g. 7 deaza-adenosine; O- and N-alkylated nucleotides, e.g. N6-methyl adenosine are suitable. The 2' OH— group can be replaced by a group selected from H. OR, R. halo, SH, SR, NH2, NHR, NR2 or CN, wherein R is C-C6 alkyl, alkenyl or alkynyl and halo is F. Cl, Br or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be used; alternatively, mixtures of different nucleic acid analogs, and mixtures of naturally occurring nucleic acids and analogs can be used. Nucleic acid sequences include but are not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc.

The term "oligonucleotide" as used herein refers to an oligomer or polymer of ribonucleic acid (RNA) or deoxyribonucleic acid (DNA) or mimetics thereof, as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. An oligonucleotide preferably includes two or more nucleomonomers covalently coupled to each other by linkages (e.g., phosphodiesters) or substitute linkages.

The term "expression" as used herein refers to the biosynthesis of a gene or nucleic acid sequence, preferably to the transcription and/or translation of a nucleotide sequence, for example an endogenous gene or a heterologous gene, in a cell. For example, in the case of a heterologous nucleic acid sequence, expression involves transcription of the heterologous nucleic acid sequence into an RNA sequence, such as an mRNA or gRNA, and, optionally, the subsequent translation of mRNA into one or more polypeptides. Expression also refers to biosynthesis of an RNA molecule, but does not require translation to polypeptide sequences. The term "expression construct" and "nucleic acid construct" as used herein are synonyms and refer to a nucleic acid sequence capable of directing the expression of a particular nucleotide sequence, such as the heterologous target gene sequence in an appropriate host cell (e.g., a prokaryotic cell, eukaryotic cell, or mammalian cell). If translation of the desired heterologous target gene is required, it also typically comprises sequences required for proper translation of the nucleotide sequence. The coding region may code for a protein of interest but may also code for a functional RNA of interest. The nucleic acid construct as disclosed herein can be chimeric, meaning that at least one of its components is heterologous with respect to at least one of its other components.

The term "enhancer" refers to a cis-acting regulatory sequence involved in the transcriptional activation of a nucleic acid sequence. An enhancer can function in either orientation and can be upstream or downstream of the promoter. As used herein, the term "gene product(s)" is used to refer to include RNA transcribed from a gene, or a polypeptide encoded by a gene or translated from RNA. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof.

The term "nucleic acid construct" as used herein refers to a nucleic acid at least partly created by recombinant methods. The term "DNA construct" refers to a polynucleotide construct consisting of deoxyribonucleotides. The construct can be single or double stranded. The construct can be circular or linear. A person of ordinary skill in the art is familiar with a variety of ways to obtain and generate a DNA construct. Constructs can be prepared by means of customary recombination and cloning techniques as are known to those of ordinary skill in the art.

The terms "polypeptide", "peptide", "oligopeptide", "polypeptide", "gene product", "expression product" and "protein" are used interchangeably herein to refer to a polymer or oligomer of consecutive amino acid residues.

Methods and Uses of Optogenetically Regulated Systems

The systems described herein are useful for engineering complex genome modifications in cellular systems, such as prokaryotic, eukaryotic, or synthetic cells, or in non-cellular systems, including test tubes, viruses and phages. The novel systems described herein harness the power of nucleic acid-based engineering methods to regulate genetic expression in transiently active cells, such as neurons, within behaviorally relevant windows of time. The systems described herein can be used for a variety of applications and in many different types of methods, including, but not limited to, monitoring and/or modulating gene expression and biomedical therapeutics.

The methods and uses of the engineered systems described herein can involve in vivo, ex vivo, or in vitro systems. The term "in vivo" refers to assays or processes that occur in or within an organism, such as a multicellular animal. The term "ex vivo" refers to methods and uses that are performed using a living cell with an intact membrane that is outside of the body of a multicellular animal or plant, e.g., explants, cultured cells, including primary cells and cell lines, transformed cell lines, and extracted tissue or cells, including blood cells, among others. The term "in vitro" refers to assays and methods that do not require the presence of a cell with an intact membrane, such as cellular extracts, and can refer to the introducing any of the systems described herein into a non-cellular system, such as a media not comprising cells or cellular systems, such as cellular extracts.

Cells of use in the various aspects described herein upon transformation or transfection with the engineered systems described herein include any cell that is capable of supporting the activation and expression of the engineered systems and component modules. In some embodiments of the aspects described herein, a cell can be from any organism or multi-cell organism. Examples of eukaryotic cells that can be useful in aspects described herein include eukaryotic cells selected from, e.g., mammalian, insect, yeast, or plant cells. The engineered systems described herein can be introduced into a variety of cells including, e.g., fungal, plant, or animal (nematode, insect, plant, bird, reptile, or mammal (e.g., a mouse, rat, rabbit, hamster, gerbil, dog, cat, goat, pig, cow, horse, whale, monkey, or human)). The cells can be primary cells, immortalized cells, stem cells, or transformed cells. In some embodiments, the cells comprise stem cells. Expression vectors for the components of the engineered systems will generally have a promoter and/or an enhancer suitable for expression in a particular host cell of interest. In alternative embodiments, the cells can be any cell, for example mammalian cells, plant cells and chimeric cells. In some embodiments, the cells can be from any organism or multi-cell organism. Examples of eukaryotic cells that can be useful in aspects described herein include eukaryotic cells selected from, e.g., mammalian, insect, yeast, or plant cells. In some embodiments, the eukaryotic cells are from a vertebrate animal. The present invention contemplates the use of any such vertebrate cells for the engineered systems described herein, including, but not limited to, reproductive cells including sperm, ova and embryonic cells, and non-reproductive cells, such as kidney, lung, spleen, lymphoid, cardiac, gastric, intestinal, pancreatic, muscle, bone, neural, brain, and epithelial cells. Also contemplated for use with the engineered systems described herein are stem cells, including human embryonic stem cells, pluripotent stem cells, multipotent stem cells, and induced pluripotent stem cells (iPSCs), as those terms are understood by one of skill in the art.

In some embodiments of the aspects described herein, engineered systems are introduced into a cellular or non-cellular system using a vector or plasmid. As used herein, the term "vector" is used interchangeably with "plasmid" to refer to a nucleic acid molecule capable of transporting another nucleic acid to which it has been linked. Vectors capable of directing the expression of genes and/or nucleic acid sequence to which they are operatively linked are referred to herein as "expression vectors." In general, expression vectors of utility in the methods and engineered systems described herein are often in the form of "plasmids," which refer to circular double stranded DNA loops which, in their vector form are not bound to the chromosome.

For example, in regard to using sequences associated with CRISPR, one of skill in the art can insert a short DNA fragment containing the DNA binding domain target site into a guide RNA expression plasmid. The sgRNA expression plasmid contains the DNA binding domain target site (about 20 nucleotides), a form of the tracrRNA sequence (the scaffold) as well as a suitable promoter and necessary elements for proper processing in eukaryotic cells. Such vectors are commercially available (see, for example, Addgene). Many of the systems rely on custom, complementary oligos that are annealed to form a double stranded DNA and then cloned into the sgRNA expression plasmid. In some embodiments, co-expression of the sgRNA and the appropriate Cas enzyme or domain thereof can be achieved using the same or separate plasmids in transfected cells results.

Other expression vectors can be used in different embodiments, for example, but not limited to, plasmids, episomes, bacteriophages or viral vectors, and such vectors can integrate into the host's genome or replicate autonomously in the particular cellular system used. Other forms of expression vectors known by those skilled in the art which serve the equivalent functions can also be used. Expression vectors comprise expression vectors for stable or transient expression encoding the DNA. A vector can be either a self-replicating extrachromosomal vector or a vector which integrates into a host genome. One type of vector is a genomic integrated vector, or "integrated vector", which can become integrated into the chromosomal DNA or RNA of a host cell, cellular system, or non-cellular system. In some embodiments, the nucleic acid sequence or sequences encoding an engineered system integrates into the chromosomal DNA or RNA of a host cell, cellular system, or non-cellular system along with components of the vector sequence. In other embodiments, the nucleic acid sequence encoding an engineered system directly integrates into chromosomal DNA or RNA of a host cell, cellular system, or non-cellular system, in the absence of any components of the vector by which it was introduced. In such embodiments, the nucleic acid sequence encoding, for example, a control module or a physiologically responsive module, can be integrated using targeted insertions, such as knock-in technologies or homologous recombination techniques, or by non-targeted insertions, such as gene trapping techniques or non-homologous recombination. The number of copies of an engineered system that integrate into the chromosomal DNA or RNA of a cellular or non-cellular system can impact the fidelity of the system, and thus it is preferred, in some embodiments, that only one copy is integrated per cellular system.

Another type of vector is an episomal vector, i.e., a nucleic acid capable of extrachromosomal replication. Such plasmids or vectors can include plasmid sequences from bacteria, viruses or phages. Such vectors include chromosomal, episomal and virus-derived vectors e.g., vectors derived from bacterial plasmids, bacteriophages, yeast episomes, yeast chromosomal elements, and viruses, vectors derived from combinations thereof, such as those derived from plasmid and bacteriophage genetic elements, cosmids and phagemids. A vector can be a plasmid, bacteriophage, bacterial artificial chromosome (BAC) or yeast artificial chromosome (YAC). A vector can be a single or double-stranded DNA, RNA, or phage vector. In some embodiments, the engineered systems are introduced into a cellular system using a BAC vector.

The vectors comprising the engineered systems described herein can be "introduced" into cells as polynucleotides, preferably DNA, by techniques well-known in the art for introducing DNA and RNA into cells. The term "transduction" refers to any method whereby a nucleic acid sequence is introduced into a cell, e.g., by transfection, lipofection, electroporation, biolistics, passive uptake, lipid:nucleic acid complexes, viral vector transduction, injection, contacting with naked DNA, gene gun, and the like. The vectors, in the case of phage and viral vectors can also be introduced into cells as packaged or encapsidated virus by well-known techniques for infection and transduction. Viral vectors can be replication competent or replication defective. In the latter case, viral propagation generally occurs only in complementing host cells. In some embodiments, the module of a system as described herein is introduced into a cell using other mechanisms known to one of skill in the art, such as a liposome, microspheres, fusion proteins, such as a fusion of an antibody moiety with a nucleic acid binding moiety, or other such delivery vehicle.

The engineered systems or the vectors comprising the engineered systems described herein can be introduced into a cell using any method known to one of skill in the art. The term "transformation" as used herein refers to the introduction of genetic material (e.g., a vector comprising one or more modules of an engineered system) comprising one or more modules or engineered systems described herein into a cell, tissue or organism. Transformation of a cell can be stable or transient. The term "transient transformation" or "transiently transformed" refers to the introduction of one or more transgenes into a cell in the absence of integration of the transgene into the host cell's genome. A "transgene" as the term is used herein encompasses both a heterologous or recombinant gene or gene construct introduced into, carried by and/or expressed by a cell. A transgene can be present in every cell of an organism, in a portion of the cells or tissues of an organism (e.g., as in a chimeric organism), or in a particular tissue- or cell type of an organism. A transgene or transgenic animal can include, for example, a knock-in sequence introduced by, for example, a gene editing method, as well as a gene sequence introduced, for example, by homologous recombination. Transient transformation can be detected by, for example, enzyme linked immunosorbent assay (ELISA), which detects the presence of a polypeptide encoded by one or more of the transgenes. Alternatively, transient transformation can be detected by detecting the activity of the protein encoded by the transgene. The term "transient transformant" refers to a cell which has transiently incorporated one or more transgenes.

In contrast, the term "stable transformation" or "stably transformed" refers to the introduction and integration of one or more transgenes into the genome of a cell or cellular system, preferably resulting in chromosomal integration and stable heritability through meiosis. Stable transformation of a cell can be detected by Southern blot hybridization of genomic DNA of the cell with nucleic acid sequences, which are capable of binding to one or more of the transgenes. Alternatively, stable transformation of a cell can also be detected by the polymerase chain reaction of genomic DNA of the cell to amplify transgene sequences. The term "stable transformant" refers to a cell or cellular, which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene. Transformed cells or tissues are understood to encompass not only the end product of a transformation process, but also transgenic progeny thereof.

Some embodiments of the technology described herein can be defined according to any of the following numbered paragraphs:
1. A system comprising:
   a. a control module comprising a nucleic acid sequence encoding a chimeric photosensitive transcription factor operably linked to a promoter, wherein the photosensitive transcription factor comprises:
      i. a transcription activation domain;
      ii. a sequence-specific DNA binding domain; and
      iii. a photo-sensitive actuator domain which is activated by photoirradiation in a defined range of wavelengths; and
   b. a physiologically responsive module comprising a nucleic acid sequence encoding a gene of interest operably linked to an inducible promoter comprising:
      i. a sequence element that binds the sequence-specific DNA binding domain of the photosensitive transcription factor, and
      ii. a physiological response element comprising a binding site for a physiological response factor, the binding of which factor is directly regulated by a physiological agent or condition;

wherein expression of the gene of interest in a cell comprising the system requires the presence of both the physiological agent or condition and photoirradiation within the defined range of wavelengths.

2. The system of paragraph 1, wherein the physiological response element comprises a binding site for an activity-dependent or hormone-dependent physiological transcription factor.

3. The system of paragraph 2, wherein the activity-dependent or hormone-dependent physiological transcription factor comprises a transcriptional repressor.

4. The system of paragraph 1, wherein the control module and the physiologically responsive module are encoded on a single nucleic acid molecule.

5. The system of paragraph 1, wherein the transcription activation domain of the photosensitive transcription factor comprises a transcription activation domain of a transcription factor selected from the group consisting of Herpes Virus VP16, HIV TAT, yeast GAL4, GCN4 or HAP1, glucocorticoid receptor transcription activation domain, B-cell POU homeodomain protein Oct2, and plant Ap2.

6. The system of paragraph 1, wherein the sequence-specific DNA binding domain comprises a DNA binding domain of a transcription factor, restriction endonuclease or an engineered DNA binding domain that binds a desired DNA sequence.

7. The system of paragraph 6, wherein the sequence-specific DNA binding domain comprises one or more zinc finger domains.

8. The system of paragraph 6, wherein the sequence-specific DNA binding domain comprises the DNA-binding domain of a transcription factor selected from the group consisting of GAL4, GCN4, Thy1, Syn1, NSE/RU5', Agrp, Calb2, Camk2a, CcK, Chat, dlx6a and Emx1.

9. The system of paragraph 7, wherein the sequence-specific DNA binding domain is engineered to bind a desired sequence.

10. The system of paragraph 1, wherein the photosensitive actuator domain comprises a photoreceptor domain selected from the group consisting of a Light-Oxygen-Voltage (LOV) photoreceptor domain, an $LOV_2$ photoreceptor domain, a Cryptochrome (CRY) photoreceptor domain, Blue-light-using FAD (BLUF) photoreceptor domain, a Phytochrome (PHY) photoreceptor domain, and a UVR8 photoreceptor domain.

11. The system of paragraph 10, wherein the LOV photoreceptor domain comprises the *Avena sativa* phototropin $LOV_2$ photoreceptor domain.

12. The system of paragraph 1, wherein the physiological response element comprises a binding site for an activity-dependent transcriptional repressor.

13. The system of paragraph 12, wherein the activity-dependent transcriptional repressor comprises the downstream responsive element antagonist modulator (DREAM) repressor and the physiological response element comprises the DREAM response element (DRE).

14. The system of paragraph 13, wherein the physiological agent or condition comprises intranuclear calcium, and wherein intranuclear calcium binds the DREAM repressor and causes dissociation of the repressor from the DRE.

15. The system of paragraph 13, further comprising a nucleic acid construct encoding the DREAM repressor.

16. The system of paragraph 1, which transduces photoirradiation within the defined range of wavelengths with a temporal resolution of less than ten minutes.

17. The system of paragraph 1, which transduces photoirradiation within the defined range of wavelengths with a temporal resolution of less than one minute.

18. The system of paragraph 1, which, in a cell in the presence of the intracellular marker of cellular activity, transduces photoirradiation within the defined range of wavelengths with a temporal resolution of less than one second.

19. The system of paragraph 18, which transduces photoirradiation within the defined range of wavelengths with a temporal resolution of less than 100 ms.

20. The system of paragraph 18, which transduces photoirradiation within the defined range of wavelengths with a temporal resolution of less than 10 ms.

21. The system of paragraph 18, wherein the photosensitive transcription factor is expressed and bound to the inducible promoter of the phys module before photoirradiation within the defined range of wavelengths is provided.

22. The system of paragraph 1, wherein the expression of the control module is constitutive.

23. The system of paragraph 1, wherein the expression of the control module is under the control of a tissue- or cell-type specific promoter.

24. The system of paragraph 1, wherein the expression of the control module is under the control of an inducible promoter.

25. The system of paragraph 1, wherein the gene of interest encodes a reporter polypeptide, a toxin or a therapeutic polypeptide.

26. The system of paragraph 1, wherein the gene of interest encodes an endonuclease or an shRNA.

27. The system of paragraph 26, wherein the endonuclease comprises a sequence-specific endonuclease.

28. The system of paragraph 27, wherein the sequence-specific endonuclease comprises an RNA-guided endonuclease or a TALEN.

29. The system of paragraph 25, wherein the reporter polypeptide comprises an enzyme or a fluorescent polypeptide.

30. The system of paragraph 25, wherein the reporter polypeptide is engineered to comprise an element that destabilizes the reporter polypeptide.

31. The system of paragraph 30, wherein the reporter polypeptide is engineered to comprise a protease cleavage site that destabilizes the reporter polypeptide.

32. A nucleic acid construct comprising a control module and a physiologically responsive module as recited in paragraph 1.

33. The nucleic acid construct of paragraph 32, further comprising nucleic acid sequence encoding a repressor that binds the physiological response element and is directly inhibited by a physiological agent or condition.

34. The nucleic acid construct of paragraph 32, wherein the physiological response element binds a physiological response factor that is directly regulated by a hormone or an activity-dependent agent.

35. The nucleic acid construct of paragraph 34, wherein the physiological response factor binds intranuclear calcium.

36. A vector comprising a nucleic acid construct of any of paragraphs 32-35.

37. The vector of paragraph 36, wherein the vector comprises a plasmid, a cosmid, or a virus.

38. A cell comprising a vector of paragraph 36.

39. The cell of paragraph 38, wherein the cell is a neuron or a stem cell.

40. The cell of paragraph 38, which is in vitro.

41. The cell of paragraph 38, which is in vivo.

42. The system of paragraph 1, further comprising a light source that delivers light within the defined range of wavelengths.

43. A transgenic non-human organism comprising the system of paragraph 1.

44. A nucleic acid molecule comprising:
- a module comprising nucleic acid sequence encoding a chimeric photosensitive transcription factor operably linked to a promoter, wherein the photosensitive transcription factor comprises:
  - a transcription activation domain;
  - a sequence-specific DNA binding domain; and
  - a photo-sensitive actuator domain which is activated by photoirradiation in a defined range of wavelengths; and
- a module comprising nucleic acid sequence encoding a physiologically responsive module comprising a nucleic acid sequence encoding a gene of interest operably linked to an inducible promoter comprising:
  - a sequence element that binds the sequence-specific DNA binding domain of the photosensitive transcription factor, and
  - a physiological response element comprising a binding site for a physiological response factor, the binding of which factor is directly regulated by a physiological agent or condition;
- wherein, when the nucleic acid molecule is introduced to a cell, expression of the gene of interest in the cell requires the presence of both the physiological agent of condition and photoirradiation within the defined range of wavelengths.

45. The nucleic acid molecule of paragraph 44, wherein the physiological response element comprises a binding site for an activity-dependent or hormone-dependent physiological transcription factor.

46. The nucleic acid molecule of paragraph 45, wherein the activity-dependent or hormone-dependent physiological transcription factor comprises a transcriptional repressor and the physiological response element comprises a repressor binding element that binds the repressor.

47. The nucleic acid molecule of paragraph 46, further comprising nucleic acid sequence encoding a repressor protein that binds the repressor binding element in a manner that is directly inhibited by the physiological agent or condition.

48. A nucleic acid molecule comprising
- a nucleic acid sequence encoding a chimeric photosensitive transcription factor operably linked to
- a promoter, wherein the photosensitive transcription factor comprises a Herpes Virus VP-16 transactivation domain, a GAL4 DNA binding domain, and an *A. sativa* LOV photosensitive actuator domain; and
- a nucleic acid sequence encoding a gene of interest operably linked to an inducible promoter comprising at least one copy of a GAL4 UAS sequence and a DRE repressor binding element, wherein expression of the gene of interest in a cell comprising the system requires the presence of both intracellular calcium in the range of about 0.1 µM to about 5 µM and light in the range that activates the *A. sativa* photosensitive actuator domain.

49. The nucleic acid molecule of paragraph 48, wherein the inducible promoter comprises at least two copies of the DRE repressor binding element.

50. A vector comprising a nucleic acid molecule of any one of paragraphs 44-49.

51. The vector of paragraph 50, wherein the vector comprises a plasmid, a cosmid, or a virus.

52. A cell comprising a vector of paragraph 51.

53. The cell of paragraph 52, wherein the cell is a neuron or a stem cell.

54. The cell of paragraph 52, which is in vitro.

55. The cell of paragraph 52, which is in vivo.

56. A method of monitoring or detecting neuronal activity, the method comprising:
- irradiating a neuron comprising a system of paragraph 1 with photoirradiation within the defined range of wavelengths; and detecting expression of the gene of interest, wherein detection of the expression of the gene of interest indicates activity of the neuron.

57. The method of paragraph 56, further comprising the step, before the step of irradiating the neuron, of introducing a system of paragraph 1 to a neuron.

58. The method of paragraph 56, wherein the system is introduced using a viral vector.

59. The method of paragraph 57, wherein the neuron is in culture.

60. The method of paragraph 57, where the neuron is in vivo.

61. The method of paragraph 56, wherein the step of irradiating the neuron comprises irradiation of the neuron via an optical fiber.

62. The method of paragraph 56, wherein the physiological agent or condition comprises intranuclear calcium.

63. The method of paragraph 56, wherein the physiological response element comprises a downstream responsive element (DRE) that binds the downstream responsive element antagonist modulator (DREAM) repressor, and wherein intranuclear calcium binds the DREAM repressor and causes dissociation of the repressor from the DRE.

64. The method of paragraph 56, wherein the gene of interest comprises a fluorescent protein and wherein detecting expression of the gene of interest comprises detecting fluorescence in said neuron.

65. A method of expressing a gene of interest in a neuron in an activation-specific manner, the method comprising:
- introducing a system of paragraph 1 to a neuron, wherein the physiological response element comprises a downstream responsive element (DRE) that binds the downstream responsive element antagonist modulator (DREAM) repressor, and wherein intranuclear calcium binds the DREAM repressor and causes dissociation of the repressor from the DRE; and
- irradiating the neuron with light within the defined range of wavelengths, wherein the gene of interest is expressed in a neuronal activation-specific manner.

66. The method of paragraph 65, wherein the gene of interest encodes a reporter polypeptide, a toxin or a therapeutic polypeptide.

67. The method of paragraph 65, wherein the gene of interest encodes an endonuclease or an shRNA.

68. The method of paragraph 67, wherein the endonuclease comprises a sequence-specific endonuclease.

69. The method of paragraph 68, wherein the sequence-specific endonuclease comprises an RNA-guided endonuclease or a TALEN.

70. A kit comprising a nucleic acid of any one of paragraphs 32-35 or 44-49, or a vector of any one of paragraphs 36, 37, 50 or 51, or a cell of any one of paragraphs 38-41, or 52-55 and packaging materials therefor.

71. The kit of paragraph 70, further comprising a cell.

72. The kit of paragraph 71, wherein the cell is a neuron or a stem cell.

As used herein, the term "comprising" means that other elements can also be present in addition to the defined elements presented. The use of "comprising" indicates inclusion rather than limitation. Accordingly, the terms "comprising" means "including principally, but not necessary solely". Furthermore, variation of the word "comprising", such as "comprise" and "comprises", have correspondingly the same meanings. The term "consisting essentially of" means "including principally, but not necessary solely at least one", and as such, is intended to mean a "selection of one or more, and in any combination". Stated another way, the term "consisting essentially of" means that an element can be added, subtracted or substituted without materially affecting the novel characteristics of the invention. This applies equally to steps within a described method as well as compositions and components therein. In other embodiments, the inventions, compositions, methods, and respective components thereof, described herein are intended to be exclusive of any element not deemed an essential element to the component, composition or method ("consisting of"). For example, a biological converter switch that comprises a sequence encoding a recombinase and a recombinase recognition sequence encompasses both the recombinase and a recombinase recognition sequence of a larger sequence. By way of further example, a composition that comprises elements A and B also encompasses a composition consisting of A, B and C.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

It is understood that the foregoing detailed description and the following examples are illustrative only and are not to be taken as limitations upon the scope of the invention. Various changes and modifications to the disclosed embodiments, which will be apparent to those of skill in the art, may be made without departing from the spirit and scope of the present invention. Further, all patents, patent applications, publications, and websites identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and do not constitute any admission as to the correctness of the dates or contents of these documents.

EXAMPLES

Characterizing how complex neural circuits interact in both time and space is critical to understanding the emergent nature of behavior from the brain. Currently there is a gap between the temporal precision at which complex neural circuits can be capture and manipulated, and the timescale at which the behavior they drive occurs.

Provided herein are systems and methods for creating a genetic regulatory system that is capable of isolating discrete neural circuits underlying complex behaviors for genetic manipulations. Building on preliminary designs using direct Ca2+ regulatory elements (CLiCK$_{Act}$) and novel photo-switchable transcription factors (CLiCK$_{TF}$) to engineer a genetic tool, CLICK (Ca2+ Light Coincidence Knock-in/out), for experimentally precise targeting of activity-dependent gene expression.

In all experimental assays, the gene encoding the fluorophore mRuby2 is used as the gene-of-interest. Most natural behaviors occur at the scale of seconds and are flanked by other states of behavior. Isolating activity-dependent gene expression in complex behaviors require the ability to carve out temporally confined windows of time matching that of the behavior. Engineering a transcription factor that is photo-switchable allows for gating resolutions of hundreds of milliseconds. Subsequently, activity-dependent gating of gene expression should also occur within these small windows of time. To address this temporal demand, a direct Ca2+ gene regulator is used providing a temporal sensitivity limited only to the diffusion rate of activity-induced Ca2+ transients. To maximize the success of engineering a temporally precise light-activity-coincidence detection system for genetic manipulation in neurons, multiple versions of each gating component are engineered and combined pairwise. Collectively assessing multiple gating components mitigates the chances of failure through poor interaction dynamics between two independently strong regulatory components.

Assessing Light-Dependent Gene Expression in HEK Cells Under Brief Periods of Photostimulation.

Since HEK cells do not endogenously express the protein through which CLiCK regulates activity-dependent gene expression, photo-induced gene expression can be evaluated in the context of complete CLiCK designs, providing insight into the functionality of the light-gating component with the unique promoter designs of the activity-dependent component. Appropriate expression of mRuby2 indicates functional designs of a temporally precise photo-switchable transcription factor.

To characterize the activity- and co(light/activity)-dependency of gene expression of CLiCK, mouse primary cortical neuron cultures are transfected and assayed under light-tight environments. Expression of mRuby2 is evaluated under KCl induced spiking, photostimulation, and simultaneous KCl photostimulation conditions. Appropriate expression of mRuby2 across conditions indicates functional designs of CLiCK. Unanticipated expression levels can be used to identify and address specific mechanistic points of failure.

CLiCK$_{TF}$ has peak light absorbency at 450 nm, which can be matched with channelrhodopsin (ChR) with similar or dissimilar excitation spectra for in vivo proof-of-principle. To evaluate CLiCK in vivo, mouse lines expressing relevant ChR in CA1 neurons are transduced with lentivirus containing the dual-independent promoter CLiCK. Taken together, the results of these experiments demonstrate the co-dependency of neural activity and photostimulation to drive gene expression. In each experiment, CLiCK is used to drive the expression of the gene encoding the fluorophore mRuby2.

Mice expressing channelrhodopsin-2, which excites at same wavelength as CLiCK$_{TF}$, in CA1 neurons are used to test the coincidence detection of CLiCK. Photostimulation is used to simultaneously excite CA1 neurons and uncage the activation domain of CLiCK$_{TF}$, driving expression of mRuby2. Presence of mRuby2 in transduced cells indicates the ability of CLiCK to act as a coincidence detector of experimentally applied light and neural activity.

Mice expressing red-shifted channelrhodopsin, which excites outside the absorbency range of CLiCK$_{TF}$, in CA1 neurons are used to test the light-dependency of CLiCK in vivo. Exciting CA1 neurons at a wavelength that does not cause uncaging of CLiCK$_{TF}$ should be inefficient to drive expression of mRuby2. Lack of mRuby2 expression indicates a light-dependency of CLiCK.

Mice expressing chloride-conducting channelrhodopsin, which photo-activate at the same wavelength as CLiCK$_{TF}$, in CA1 neurons are used to silence cells while simultaneously uncaging the CLiCK$_{TF}$. Uncaging CLiCK$_{TF}$ in optogenetically silenced CA1 neurons tests the activity-dependency of CLiCK.

To test in vivo Ca2+-Light dependent gene expression, in some embodiments, viral I injection is used: Mouse (WT, ~15 weeks); Bilateral CA1 injection of AAV complex comprising AAV2/9-CBA-CLiCK$_{TF}$; AAV2/9-CLiCK$_{Act}$; and AAV2/9-Syn-ChR2-eYFP. 600 nL total at 100 nL/min. Incubated 7-16 days. Fiber implant tested using a unilateral CA1 fiber implant with a non-implanted hemisphere serving as (−) control. For in vivo photostimulation, a 473 nm laser is used at ~8 mW. 3×[5×1 sec 10 Hz pulse at 3 sec intervals] at 10 sec intervals. Perfused 24 hrs later. Brains are flash frozen in dry ice chilled 2-methyl-butane, cryosectioned and mounted for imaging.

An ability to identify, isolate, and perturb distinct transient neural circuits in vivo can revolutionize our fundamental understanding of how neural circuits interact to encode information in the brain, bringing the field from observation to causation. For example, the research described in S Ramirez, X Liu, P A Lin, J Suh, and Susumu Tonegawa. Creating a false memory in the hippocampus. Science, 341(July):387-391, 2013, links internal representations of episodic memories to subpopulations of context-driven dentate granule cells in the hippocampus and were able to physiologically generate false memories in mice. Other groups have turned to optical microscopy to visually target active cells for photostimulation [Adam M Packer, Lloyd E Russell, Henry W P Dalgleish, and Michael Hausser. Simultaneous all-optical manipulation and recording of neural circuit activity with cellular resolution in vivo. 12(2), 2014; John Peter Rickgauer, Karl Deisseroth, and David W Tank. Simultaneous cellular-resolution optical perturbation and imaging of place cell firing fields. Nat Publ Gr, 17(12):1816-1824, 2014; Vivien Szabo, Cathie Ventalon, Jonathan Bradley, and Valentina Emiliani. Patterned photo-activation with computer-generated holography and functional fluorescence imaging in freely behaving mice with a fiberscope. Neuron, 84(6):1157-1169, 2014.1. However, this approach is limited to applications of photosensitive proteins instead of driving expression of genes which may or may not be photosensitive, suffers from limited axial range, and requires removal of overlaying brain tissue which may be involved in the circuit dynamics being investigated.

One of the contributions of the technology described herein is providing an ability to genetically capture functionally distinct neural circuits at behaviorally relevant timescales. This technology has the potential to bring forth a new wave of research that exploits all the functionalities and utility of genetics in characterizing the neural architecture and dynamics underlying complex behavior. Precise experimental control of the window of time in which active neurons express a gene of interest addresses one of the largest current barriers in neuroscience, the ability to dial in a truly arbitrary, naturalistic activity pattern. The technology described herein provides a fundamental launching point for a highly tailorable tool that gives researchers the ability to genetically interact with transiently active neurons in finely specified windows of time.

Though innovations like optogenetics have led to fantastic new insights in neural circuitry they are by and large limited to the targeting of whole subpopulations of neurons by cell type/region. Characterizing by manipulating neural circuits through cell type or region is akin to characterizing an electric circuit by turning all its transistors on and off at the same time. The whole electrical network is set to a state of chaos and any hope of elucidating discrete dynamics is greatly confounded. Activity-dependent genetics has the potential to bring functional selectivity to not only optogenetics but the entire collection of genetic tools, for example, CRISPR, TALEN, or shRNAs. These genetic tools can be precisely applied to functionally isolated neural circuits to drive neural excitability, up/down-regulate or knock-in/out genes creating unprecedented opportunities to characterize neural circuits and the behaviors they drive.

Recently, the role of neural ensembles in the hippocampus has been explored using a c-fos tetracycline gene expression system. A c-fos promoter drives the expression of a tetracycline transactivator (tTA) to induce expression of a downstream channelrhodopsin. Experimental control is given to the researchers through dietary intake of doxycycline (Dox), which degrades the tTA. However, the timescale at which the tTA can be controlled through Dox (hours) prevents its application in studies of complex behaviors which cannot be easily, if at all, isolated in hours long windows of time. Successful application of this tool requires behaviors to be isolated by tightly controlled environments hours before and after a behavior. Furthermore, expression of the optogenetic gene that can be experimentally controlled is not at a level that parallels behavior. Instead, experiments need to be rigidly designed to isolate a specific behavior over a time period of hours. Immediate early genes (IEGs), like c-Fos, are not always turned on by neural activity, are sensitive to numerous stimuli, like growth factors, and are activated by several intracellular signaling pathways including CAMP, Ca2+, and MAPK. Advances in optics and Ca2+ indicators have allowed for simultaneously observation and directed targeting of activate cells by photostimulation. However, this approach is limited in its in vivo applications, typically restricted to virtual environments. Photostimulation is restricted to within the field of view, having poor depth of field, while deep brain structures require the removal of overlying brain tissue. Additionally, the cost of the technology that these techniques rely on can be substantially prohibitive for many researchers.

An innovation of the technology described herein is providing a new gene regulatory system that allows researchers to isolate and genetically manipulate active cells, such as neurons, with seconds to milliseconds experimental windows. The technology overcomes the critical limitation of poor experimental temporal specificity of gene expression by uniquely combining the fast gating mechanisms of e.g., a phototropin, to a strong transcriptional activator and localizing it to the target gene. By drastically advancing the temporal resolution at which experimental windows of time can be set, naturalistic behaviors, which are typically part of a larger set of behaviors occurring within a small window of time, can be isolated. With such high experimental resolution IEGs, which can take minutes to hours to be turned on by activity, do not provide the level of temporal sensitivity needed. While optical applications of Ca2+ indicators have benefited from the fast, direct transduction of neural activity by Ca2+ transients, Ca2+ transients have not been capitalized on in driving activity-dependent gene expression.

The technology developed herein introduces the first application of a gene regulatory system that is directly driven by Ca2+ transients. Forgoing all intermediate signaling molecules in IEGs, direct Ca2+ regulation of gene expression, in combination with the high temporal control of experimental windowing, the technology described herein can be used to bring forth a new wave of research in a variety of disciplines, including neuroscience.

The invention claimed is:

1. A system comprising:
   a. a control module comprising a nucleic acid sequence encoding a chimeric photosensitive transcription factor operably linked to a promoter, wherein the photosensitive transcription fact comprises:
      i. a transcription activation domain;
      ii. a sequence-specific DNA binding domain; and
      iii. a photo-sensitive actuator domain which is activated by photoirradiation in a defined range of wavelengths; and
   b. a physiologically responsive module comprising a nucleic acid sequence encoding a gene of interest operably linked to an inducible promoter comprising:
      i. a sequence element that binds the sequence-specific DNA binding domain of the photosensitive transcription factor, and ii. a physiological response element comprising a binding site for a downstream responsive element antagonist modulator (DREAM) repressor, the binding of which is directly regulated by intranuclear calcium; wherein expression of the gene of interest in a cell comprising the system requires the presence of both: (i) intranuclear calcium and (ii) photoirradiation within 400-900 nm.

2. The system of claim 1, wherein the control module and the physiologically responsive module are encoded on a single nucleic acid molecule.

3. The system of claim 1, wherein the transcription activation domain of the photosensitive transcription factor comprises a transcription activation domain of a transcription factor selected from the group consisting of Herpes Virus VP16, HIV TAT, yeast GAL4, GCN4 or HAP1, glucocorticoid receptor transcription activation domain, B-cell POU homeodomain protein Oct2, and plant Ap2.

4. The system of claim 1, wherein the sequence-specific DNA binding domain comprises a DNA binding domain of a transcription factor, restriction endonuclease or an engineered DNA binding domain that binds a desired DNA sequence.

5. The system of claim 4, wherein the sequence-specific DNA binding domain comprises one or more zinc finger domains.

6. The system of claim 4, wherein the sequence-specific DNA binding domain comprises the DNA-binding domain of a transcription factor selected from the group consisting of GALA, GCN4, Thy1, Syn1, NSE/RU5', Agrp, Calb2, Camk2a, CcK, Chat, dlx6a and Emx1.

7. The system of claim 1, wherein the photosensitive actuator domain comprises a photoreceptor domain selected from the group consisting of a Light-Oxygen-Voltage (LOV) photoreceptor domain, an $LOV_2$ photoreceptor domain, a Cryptochrome (CRY) photoreceptor domain, Blue-light-using FAD (BLUF) photoreceptor domain, a Phytochrome (PHY) photoreceptor domain, and a UVR8 photoreceptor domain.

8. The system of claim 7, wherein the LOV photoreceptor domain comprises the *Avena saliva* phototropin $LOV_2$ photoreceptor domain.

9. The system of claim 1, wherein intranuclear calcium binds the DREAM repressor and causes dissociation of the repressor from the DREAM responsive element (DRE).

10. The system of claim 1, further comprising a nucleic acid construct encoding the DREAM repressor.

11. The system of claim 1, wherein the system transduces an optical stimulus to a shift in transcriptional activity in less than ten minutes.

12. The system of claim 11, wherein the photosensitive transcription factor is expressed and bound to the inducible promoter of the physiologically responsive module before photoirradiation within 400-900 nm is provided.

13. The system of claim 1, wherein the gene of interest encodes a reporter polypeptide, a toxin or a therapeutic polypeptide.

14. The system of claim 13, wherein the reporter polypeptide is engineered to comprise a degradation tag.

15. A nucleic acid molecule comprising:
a. a module comprising a nucleic acid sequence encoding a chimeric photosensitive transcription factor operably linked to a promoter, wherein the photosensitive transcription factor comprises:
i. a transcription activation domain;
ii. a sequence-specific DNA binding domain; and
iii. a photo-sensitive actuator domain which is activated by photoirradiation in a defined range of wavelengths; and
b. a module comprising a nucleic acid sequence encoding a physiologically responsive module comprising a nucleic acid sequence encoding a gene of interest operably linked to an inducible promoter comprising:
i. a sequence element that binds the sequence-specific DNA binding domain of the photosensitive transcription factor, and
ii. a physiological response element comprising a binding site for a downstream responsive element antagonist modulator (DREAM) repressor, the binding of which is directly regulated by intranuclear calcium;
wherein, when the nucleic acid molecule is introduced to a cell, expression of the gene of interest in the cell requires the presence of both: (i) intranuclear calcium and (ii) photoirradiation within 400-900 nm.

16. A nucleic acid molecule comprising:
a. a nucleic acid sequence encoding a chimeric photosensitive transcription factor operably linked to a promoter, wherein the photosensitive transcription factor comprises a Herpes Virus VP-16 transactivation domain, a GAL4 DNA binding domain, and an *A. sativa* LOV photosensitive actuator domain; and
b. a nucleic acid sequence encoding a gene of interest operably linked to an inducible promoter comprising at least one copy of a GAL4 UAS sequence and a DRE repressor binding element, wherein expression of the gene of interest in a cell comprising the system requires the presence of both intracellular calcium in the range of about 0.1 µM to about 5 µM and light in the range of wavelengths that activate the *A. sativa* photosensitive actuator domain.

17. The nucleic acid molecule of claim 16, wherein the inducible promoter comprises at least two copies of the DRE repressor binding element.

18. A method of monitoring or detecting neuronal activity, the method comprising: irradiating a neuron comprising a system of claim 1 with photoirradiation within the defined range of wavelengths; and detecting expression of the gene of interest, wherein detection of the expression of the gene of interest indicates activity of the neuron.

19. The method of claim 18, wherein the step of irradiating the neuron comprises irradiation of the neuron via an optical fiber.

20. The method of claim 18, wherein the physiological response element comprises a downstream responsive element (DRE) that binds the downstream responsive element antagonist modulator (DREAM) repressor, and wherein intranuclear calcium binds the DREAM repressor and causes dissociation of the repressor from the DRE.

21. A method of expressing a gene of interest in a neuron in an activation-specific manner, the method comprising:
introducing a system of claim 1 to a neuron, wherein the physiological response element comprises a downstream responsive element (DRE) that binds the downstream responsive element antagonist modulator (DREAM) repressor, and wherein intranuclear calcium binds the DREAM repressor and causes dissociation of the repressor from the DRE; and
irradiating the neuron with light within the defined range of wavelengths, wherein the gene of interest is expressed in a neuronal activation-specific manner.

22. The method of claim 21 wherein the gene of interest encodes a reporter polypeptide, an endonuclease, an shRNA, a toxin, or a therapeutic polypeptide.

23. The method of claim 22, wherein the endonuclease comprises a sequence-specific endonuclease.

\* \* \* \* \*